United States Patent
Ivanoff et al.

(10) Patent No.: US 11,420,047 B2
(45) Date of Patent: Aug. 23, 2022

(54) WIRELESS PATCH SYSTEM FOR TRANSDERMAL, TRANSMUCOSAL AND DENTAL ELECTRICAL DRUG DELIVERY

(71) Applicant: Athena E. Ivanoff, Westlake, OH (US)

(72) Inventors: Chris S. Ivanoff, North Olmstead, OH (US); Jie Wu, Knoxville, TN (US); Timothy L. Hottel, Piperton, TN (US)

(73) Assignee: Athena E. Ivanoff, Westlake, OH (US)

( * ) Notice: Subject to any disclaimer, the term of this patent is extended or adjusted under 35 U.S.C. 154(b) by 0 days.

(21) Appl. No.: 15/565,534

(22) PCT Filed: May 6, 2016

(86) PCT No.: PCT/US2016/031230
§ 371 (c)(1),
(2) Date: Oct. 10, 2017

(87) PCT Pub. No.: WO2016/182919
PCT Pub. Date: Nov. 17, 2016

(65) Prior Publication Data
US 2018/0110975 A1    Apr. 26, 2018

Related U.S. Application Data

(60) Provisional application No. 62/158,923, filed on May 8, 2015.

(51) Int. Cl.
*A61N 1/32* (2006.01)
*A61C 19/06* (2006.01)
*A61M 37/00* (2006.01)

(52) U.S. Cl.
CPC .............. *A61N 1/325* (2013.01); *A61C 19/06* (2013.01); *A61C 19/063* (2013.01);
(Continued)

(58) Field of Classification Search
CPC .... A61N 1/325; A61N 1/0428; A61N 1/0432; A61N 1/0448; A61N 1/00; A61N 1/0472;
(Continued)

(56) References Cited

U.S. PATENT DOCUMENTS

| | | |
|---|---|---|
| 3,207,161 A | 9/1965 | Dietz |
| 4,629,424 A | 12/1986 | Lauks et al. |

(Continued)

OTHER PUBLICATIONS

Notification Concerning Availability of the Publication of the International Application corresponding to International application No. PCT/US2016/031230 dated Nov. 17, 2016.
(Continued)

*Primary Examiner* — Nilay J Shah
(74) *Attorney, Agent, or Firm* — Jenkins, Wilson, Taylor & Hunt, P.A.

(57) ABSTRACT

Methods and systems for delivering drug particles to a target site are disclosed. An example method for implementing the subject matter described herein includes applying a drug delivery patch to a target site. The drug delivery patch can include a substrate, an electrode integrated with the substrate, and a fluid in the substrate having drug particles suspended in the fluid. The method further includes transmitting a signal to the drug delivery patch to power the drug delivery patch by inductive coupling. Powering the drug delivery patch causes the electrode in the drug delivery patch to motivate the drug particles towards a target site of the drug delivery patch.

8 Claims, 42 Drawing Sheets

(52) U.S. Cl.
CPC ........ *A61C 2204/005* (2013.01); *A61M 37/00* (2013.01); *A61M 2037/0007* (2013.01); *A61M 2205/3592* (2013.01); *A61M 2205/8243* (2013.01)

(58) Field of Classification Search
CPC ... A61N 1/0476; A61N 1/0492; A61M 37/00; A61M 2037/0007; A61M 2205/3592; A61M 2205/8243; A61C 19/06; A61C 19/063; A61C 19/066; A61C 19/08
See application file for complete search history.

(56) References Cited

U.S. PATENT DOCUMENTS

| | | | | |
|---|---|---|---|---|
| 4,977,895 | A | * | 12/1990 | Tannenbaum ..... A61N 1/36014 607/46 |
| 5,306,235 | A | * | 4/1994 | Haynes ..... A61N 1/30 604/20 |
| 5,551,953 | A | * | 9/1996 | Lattin ..... A61B 5/14514 604/20 |
| 6,382,979 | B2 | | 5/2002 | Lindquist |
| 6,749,427 | B1 | | 6/2004 | Bretscher et al. |
| 8,956,157 | B2 | | 2/2015 | Rutberg et al. |
| 9,358,380 | B2 | | 6/2016 | Ivanoff et al. |
| 2001/0038998 | A1 | | 11/2001 | Lindquist |
| 2005/0273046 | A1 | | 12/2005 | Kwiatkowski |
| 2007/0104023 | A1 | * | 5/2007 | Hood ..... A61M 5/14276 366/127 |
| 2007/0106271 | A1 | * | 5/2007 | Hood ..... A61K 9/0009 604/890.1 |
| 2007/0106277 | A1 | * | 5/2007 | Hood ..... A61M 5/145 604/891.1 |
| 2008/0114282 | A1 | * | 5/2008 | Carter ..... A61N 1/044 604/20 |
| 2008/0146986 | A1 | * | 6/2008 | Riga ..... A61N 1/0436 604/20 |
| 2008/0280260 | A1 | | 11/2008 | Belikov et al. |
| 2009/0005727 | A1 | * | 1/2009 | Hood ..... A61M 37/0092 604/65 |
| 2009/0117513 | A1 | | 5/2009 | Nemeh et al. |
| 2010/0030185 | A1 | * | 2/2010 | Hood ..... A61M 5/14276 604/500 |
| 2010/0137780 | A1 | | 6/2010 | Singh et al. |
| 2012/0156648 | A1 | | 6/2012 | Kaufman et al. |
| 2012/0295218 | A1 | | 11/2012 | Moll |
| 2012/0315596 | A1 | | 12/2012 | Gan et al. |
| 2013/0215979 | A1 | | 8/2013 | Yakovlev et al. |
| 2014/0093836 | A1 | | 4/2014 | Wolpo |
| 2014/0162206 | A1 | | 6/2014 | Ivanoff et al. |
| 2015/0072300 | A1 | | 3/2015 | Wolpo |

OTHER PUBLICATIONS

Notification of Transmittal of the International Search Report and the Written Opinion of the International Searching Authority, or the Declaration corresponding to International application No. PCT/US2016/031230 dated Aug. 8, 2016.
International Preliminary Report on Patentability corresponding to International Application No. PCT/US2016/031230 dated Nov. 14, 2017.
Notification Concerning Transmittal of International Preliminary Report on Patentability corresponding to International Application No. PCT/US2016/031230 dated Nov. 23, 2017.
Castellanos et al., "Electrohydrodynamics and dielectrophoresis in microsystems: Scaling laws," J. Phys. D: Appl. Phys. vol. 36, No. 20 pp. 2584-2597(2003).
Chaurey et al.,"Floating-electrode enhanced constriction dielectrophoresis for biomolecular trapping in physiological media of high conductivity," Biomicrofluidics. vol. 6, No. 1 p. 012806 (2012).
Chaurey et al., "Scaling down constriction-based (electrodeless) dielectrophoresis devicesfor trapping nanoscale bioparticles in physiological media of high-conductivity," Electrophoresis vol. 34, No. 7 pp. 1097-1104 (2013).
Erickson et al., "Analysis of alternating current electroosmotic flows in a rectangular microchannel," Langmuir vol. 19 pp. 5421-5430 (2003).
Gascoyne et al., "Particle Separation by Dielectrophoresis," Electrophoresis vol. 23 pp. 1973-1983 (2002).
Green, N.G., and Morgan, H., "Dielectrophoretic separation of nano-particles," J. Phys. D: Appl. Phys. vol. 30, No. 11 pp. L41-L44 (1997).
Green, N.G., and Morgan, H., "Separation of submicrometre particles using a combination of dielectrophoretic and electrohydrodynamic forces," J. Phys. D: Appl. Phys. vol. 31 pp. L25-L30 (1998).
Green et al., "Fluid flow induced by nonuniform ac electric fields in electrolytes on microelectrodes. I. Experimental measurements," Phys. Rev. E. vol. 61, No. 4 pp. 4011-4018 (2000).
Gonzalez et al., "Fluid flow induced by non-uniform ac electric fields in electrolytes on microelectrodes. II. A linear double-layer analysis." Phys. Rev. E. vol. 61, No. 4, pp. 4019-4028 (2000).
Green et al., "Fluid flow induced by nonuniform ac electric fields in electrolytes on microelectrodes. III. Observation of streamlines and numerical simulation." Phys. Rev. E vol. 66, No. 2:026305 (2002).
Hasan, R.S.M., and Khurma, A., "Ac dielectrophoresis using elliptic electrode geometry," Journal of Sensors. Article ID 204767 (8 pages) (2011).
Holmes et al., "Cell positioning and sorting using dielectrophoresis," European Cells and Materials vol. 4, No. 2 pp. 120-122 (2002).
Hughes et al., "Dielectrophoretic trapping of single sub-micrometre scale bioparticles," J. Phys. D, vol. 31 pp. 2205-2210 (1998).
Islam et al., "Enhancing microcantilever capability with integrated AC electroosmosis trapping," Microfluid. Nanofluid. vol. 3, No. 3 pp. 269-375 (2007).
Ivanoff et al. 19th International Symposium, Exhibit & Workshops on Electro- and Liquid, Phase-separation Technique, ITP 2012 Book of Abstracts.
Ivanoff et al., "Breaking the fluoride diffusion barrier with combined dielectrophoresis and AC electroosmosis," American Journal of Dentistry. vol. 26, No. 4, pp. 228-236 (2013).
Ivanoff, "Dielectrophoretic Transport Increases Depth of Penetration of Fluoride into Enamel," In Effectvie Community Preventitive Programs: American Public Health Association 140th Annual Meeting & Expo, San Francisco, California, Oct. 27-Oct. 31, 2012; abstract 259087.
Ivanoff et al., "Dielectrophoresis: A model to transport drugs directly into teeth," Electrophoresis. vol. 33, No. 8 pp. 1311-1321 (2012).
Ivanoff et al., "Dielectrophoresis enhances the whitening effect of carbamide peroxide on enamel," Am. J. Dent. vol. 24 pp. 259-263 (2011).
Ivanoff et al., "Dielectrophoretic transport of fluoride into enamel," Am. J. Dent. vol. 24, No. 6 pp. 341-345 (2011).
Ivanoff et al. "Enhanced penetration of fluoride particles into bovine enamel by combining dielectrophoresis with AC electroosmosis" Electrophoresis, vol. 34 (20-21 pp. 2945-2955 (2013); DOI:10.1002/elps.201300206.
Ivanoff et al., "Fluoride uptake by human tooth enamel: Topical application versus combined dielectrophoresis and AC electroosmosis," Am. J. Dent. vol. 26(3), 166-172 (13 pages) (2013).
Ivanoff et al., "Microhardness recovery of demineralized enamel after treatment with fluoride gel or CPP-ACP paste applied topically or with dielectrophoresis," Am. J. Dent. vol. 25, No. 2 pp. 109-113 (2012).
Iverson et al., "Recent advances in microscale pumping technologies: a review and evaluation," International Journal of Microfluidics and Nanofluidics vol. 5, Issue 2 pp. 145-174 (2008).
Khoshmanesh et al., "Dielectrophoretic platforms for bio-microfluidic systems," Biosens. Bioelectron. vol. 26, No. 5 pp. 1800-1814 (2011).
Lian, M., and Wu, J., "Ultrafast micropumping by biased alternating current electrokinetics," Appl. Phys. Lett. vol. 94 p. 064101 (2009).

(56) References Cited

OTHER PUBLICATIONS

Liao et al., Nano-constriction device for rapid protein preconcentration in physiological media through a balance of electrokinetic forces Electrophoresis. vol. 33 pp. 1958-1966 (2012).
Liu et al., "Microfluidic Pumping based on Traveling-Wave Dielectrophoresis," Nanoscale and Microscale Thermophysical Engineering. vol 13 pp. 109-133 (2009).
Luo et al., "Nanoelectrode arrays for on-chip manipulation of biomolecules in aqueous solutions," Microelectronic Engineering. vol. 83 pp. 1634-1637 (2006).
Melvin et al., "On-chip collection of particles and cells by AC electroosmotic pumping and dielectrophoresis using asymmetric electrodes," Biomicrofluidics. vol. 5 p. 034113 (2011).
Morgan et al., "Separation of submicron bioparticles by dielectrophoresis," Biophys. J. vol. 77, No. 1 pp. 516-525 (1999).
Notice of Allowance corresponding to U.S. Appl. No. 14/092,269 dated Jan. 26, 2016.
Office Action corresponding to U.S. Appl. No. 14/092,269 dated Nov. 28, 2014.
Office Action corresponding to U.S. Appl. No. 14/092,269 dated Jul. 6, 2015.
Pethig, "Review article-dielectrophoresis: status of the theory, technology, and applications," Biomicrofluidics. vol. 4, No. 2 pp. 1-35 (2010).
Pohl, "The motion and precipitation of suspensoids in divergent electric fields," J. Appl. Phys. vol. 22 pp. 869-871 (1951).
Pohl., "Some effects of nonuniform fields on dielectrics," J. Appl. Phys., vol. 29, No. 8 pp. 1182-1188 (1958).
Ramos et al., "Pumping of liquids with ac voltages applied to asymmetric pairs of microelectrodes," Phys. Rev. E. vol. 67 p. 056302 (2003).
Ramos et al., "AC electric-field-induced fluid flow in microelectrodes," J. Colloid Interface Sci. vol. 217 pp. 420-422 (1999).
Ramos et al., "AC electrokinetics: a review of forces in microelectrode structures," J. Phys. D: Appl. Phys. vol. 31 pp. 2338-2353 (1998).
Ramos et al., "A linear analysis of the effect of Faradaic currents on travelling-wave electroosmosis," J. Colloid Inderface Sci. vol. 309, No. 2 pp. 323-331 (2007).
Suehiro et al., "The dielectrophoretic movement and positioning of a biological cell using three-dimensional grid electrode system," J. Physics D vol. 31 pp. 3298-3305 (1998).
Urbanski et al., "Fast ac electro-osmotic micropumps with nonplanar electrodes," Appl. Phys. Lett. vol. 89, No. 14:143508 (2006).
Wong et al., "Electrokinetic bioprocessor for concentrating cells and molecules," Anal. Chem. vol. 76, No. 23 pp. 6908-6914 (2004).
Wu, J., and Chang, H.C., "Asymmetrically biased AC electrochemical micropump," AIChE Annual Meeting. Austin, Texas (Nov. 7-12, 2004).
Wu et al., "Long-range AC electrokinetic trapping and detection of bioparticles," Industr. Eng. Chem. Research. vol. 44, No. 8 pp. 2815-2822 (2005).
Wu, J., "Biased ac electro-osmosis for on chip bioparticle processing," IEEE Trans. Nanotechnol. vol. 5, No. 2 pp. 84-88 (2006).
Wu, J., "Interaction of electrical fields with fluids: laboratory-on-chip applications," IET Nanobiotechnol. vol. 2, No. 1 pp. 14-27 (2008).
Wu et al., "Transport of particles and microorganisms in microfluidic-channels using rectified ac electro-osmotic flow," Biomicrofluidics, vol. 5:013407 (2011).
Zeng et al., "Fabrication and characterization of electroosmotic micropumps," Sensor and Actuator B vol. 79 pp. 107-114 (2001).
Zhang et al., "Simulation of ion generation and breakdown in atmospheric air," J. Applied Physics vol. 96 pp. 6066-6072 (2004).
Burke, "Nanodielectrophoresis: Electronic nanotweezers," Nalwa, H.S. (Ed.), Encyclopedia of Nanoscience and Nanotechnology. Department of Electrical and Computer Engineering, University of California, Irvine, California, USA, vol. X pp. 1-19 (2003).
Singhal et al., "A Novel Valveless Micropump with Electrohydrodynamic Enhancement for High Heat Flux Cooling," Purdue University, CTRC Research Publications, Paper 18, pp. 1-43 (2005).
Ivanoff et al., Supplemental Document, 7 pages, 2013 [additional supporting information for the online version of the research article "Enhanced penetration of fluoride particles into bovine enamel by combining dielectrophoresis with AC electroosmosiss," Electrophoresis, vol. 34, Iss. 20-21, pp. 2945-2955 (2013)], available online at: https://analyticalsciencejournals.onlinelibrary.wiley.com/action/downloadSupplement?doi=10.1002%2Felps.201300206&file=elps4834-sup-0001-SuppMat.doc; retrieved online Mar. 25, 2021.

\* cited by examiner

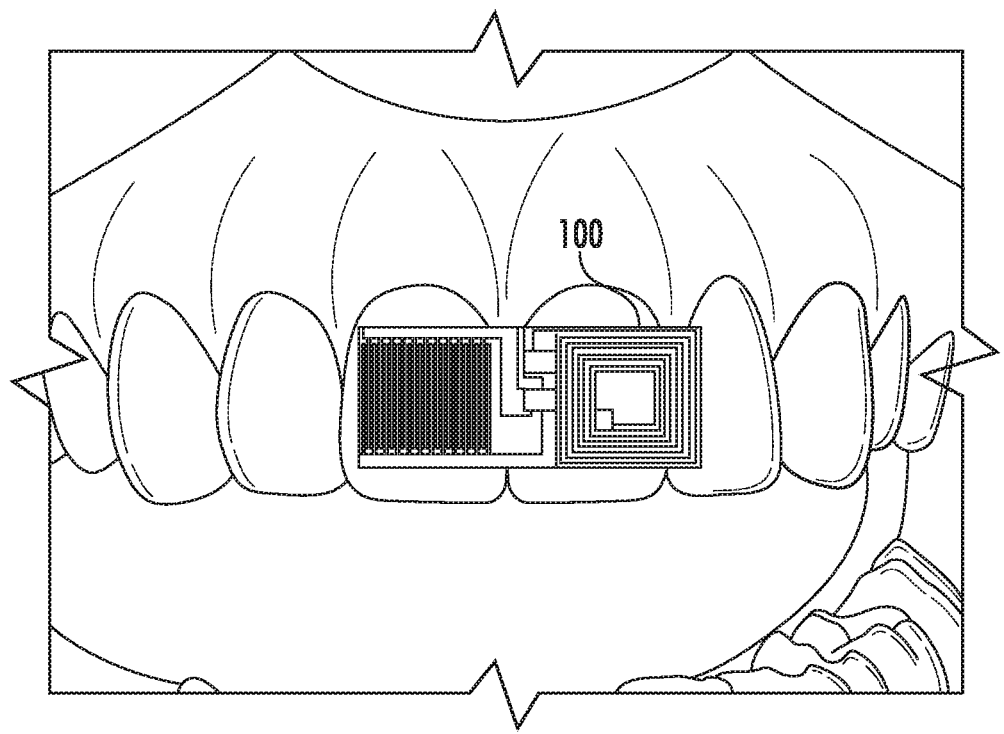
FIG. 1A
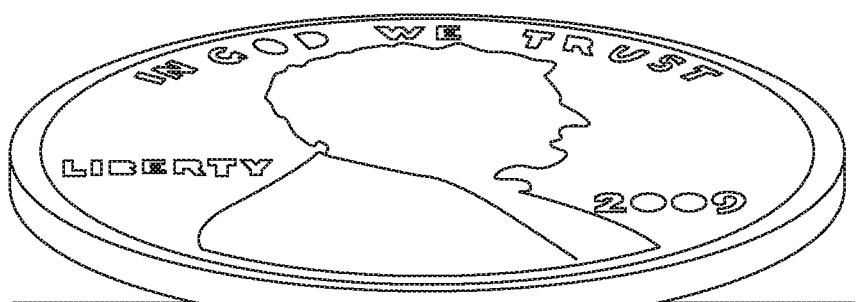
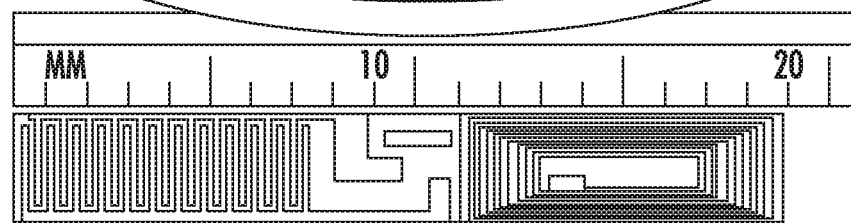
FIG. 1B

| TABLE 1. PRE- AND POST-TREATMENT SCI AND SCE L* VALUES FOR DIFFUSION AND ACEK TREATED TEETH ||||||
|---|---|---|---|---|---|
| SCI AND SCE L* ACEK TREATED TEETH ||||||
| SAMPLE | ACEK SCI BASELINE | ACEK SCI POST-TX | CHANGE IN SCI (L*UNITS) | ACEK SCE BASELINE | ACEK SCE POST-TX | ACEK CHANGE IN SCE(L*UNITS) |
| 1 | 82.63 | 85.82 | 3.19 | 80.88 | 83.82 | 2.94 |
| 2 | 82.81 | 85.83 | 3.02 | 83.37 | 85.80 | 2.42 |
| 3 | 85.01 | 89.22 | 2.83 | 83.53 | 85.74 | 2.21 |
| 4 | 87.54 | 89.22 | 1.68 | 86.49 | 87.88 | 1.39 |
| 5 | 86.75 | 88.87 | 2.12 | 85.51 | 86.81 | 1.3 |
| 6 | 88.54 | 90.00 | 1.46 | 87.45 | 88.49 | 1.04 |
| 7 | 88.99 | 89.78 | 0.79 | 87.32 | 87.83 | 0.51 |
| 8 | 89.28 | 90.63 | 1.35 | 87.81 | 88.84 | 1.03 |
| 9 | 85.62 | 89.33 | 3.71 | 84.28 | 87.55 | 3.27 |
| 10 | 88.98 | 90.68 | 1.7 | 88.65 | 89.74 | 0.78 |
| 11 | 89.53 | 91.20 | 1.67 | 86.64 | 88.85 | 1.09 |
| 12 | 82.49 | 86.44 | 3.95 | 81.46 | 85.04 | 3.58 |
| 13 | 87.82 | 90.48 | 2.66 | 86.64 | 88.85 | 2.21 |
| 14 | 89.93 | 91.53 | 1.6 | 88.57 | 88.86 | 1.29 |
| 15 | 89.5 | 91.48 | 1.53 | 88.59 | 88.78 | 1.19 |
| | | AVG | 2.217 | | AVG | 1.751 |
| | | STDEV | 0.942924 | | STDEV | 0.954497 |
| SCI AND SCE L* DIFFUSION TREATED TEETH ||||||
| SAMPLE | DIF SCI BASELINE | DIF SCI POST-TX | CHANGE IN SCI (L*UNITS) | DIF SCE BASELINE | DIF SCE POST-TX | DIF CHANGE IN SCE(L*UNITS) |
| 1 | 86.93 | 87.4 | 0.47 | 85.29 | 85.8 | 0.51 |
| 2 | 88.1 | 88.36 | 0.26 | 86.45 | 86.54 | 0.09 |
| 3 | 88.02 | 88.08 | 0.06 | 88.1 | 88.18 | 0.08 |
| 4 | 83.8 | 88.81 | 2.01 | 81.95 | 83.60 | 1.65 |
| 5 | 87.67 | 87.73 | 0.06 | 86.16 | 86.22 | 0.06 |
| 6 | 88.54 | 88.8 | 1.72 | 85.74 | 87.41 | 1.67 |
| 7 | 84.32 | 86.23 | 1.91 | 81.94 | 83.37 | 1.42 |
| 8 | 87.03 | 87.39 | .036 | 85.58 | 85.62 | 0.04 |
| 9 | 86.95 | 88.44 | 1.49 | 85.56 | 86.58 | 1.02 |
| 10 | 87.32 | 88.86 | 1.54 | 85.77 | 87.81 | 2.04 |
| 11 | 87.8 | 87.81 | 0.01 | 86.39 | 87.94 | 1.55 |
| 12 | 86.07 | 87.96 | 1.89 | 84.63 | 85.76 | 1.13 |
| 13 | 88.68 | 89.63 | 0.95 | 87.32 | 87.94 | 0.62 |
| 14 | 89.63 | 89.71 | 0.08 | 88.32 | 88.41 | 0.09 |
| 15 | 87.42 | 89.42 | 1.99 | 86.13 | 87.71 | 1.58 |
| | | AVG | 0.987 | | AVG | 0.904 |
| | | STDEV | 0.823847 | | STDEV | 0.724478 |
| DIFFERENCE IN SCE L* ACEK VS DIFFUSION ||||||
| ΔSCI L*ACEK-DIF | | SCI L*INCREASE | | ΔSCE L*ACEK-DIF | | SCE L*INCREASE |
| 1.230 UNITS | | 215.0% | | 0847 UNITS | | 193.7% |

FIG. 8

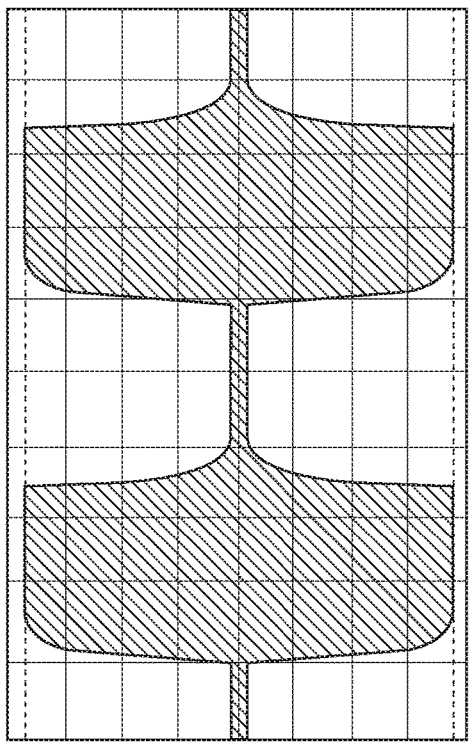
FIG. 18A1
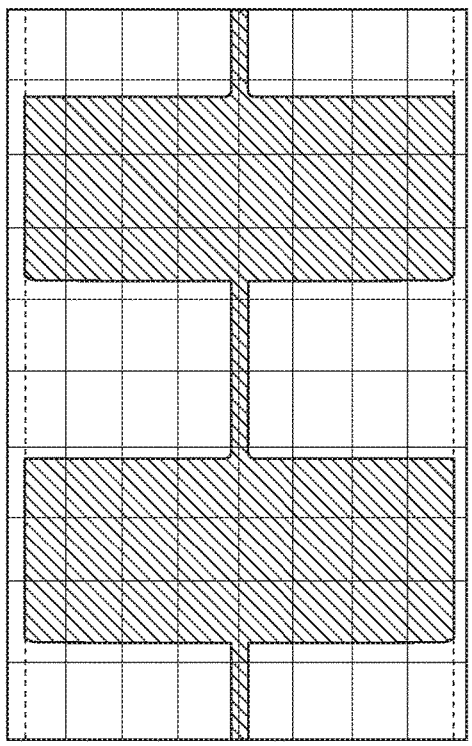
FIG. 18A2
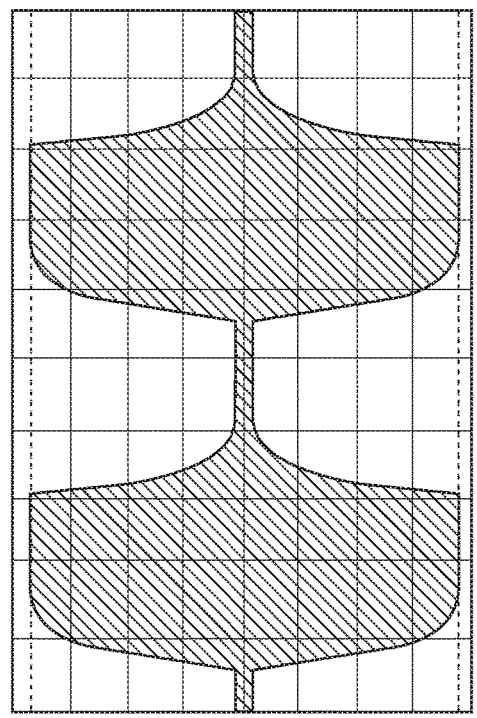
FIG. 18A3

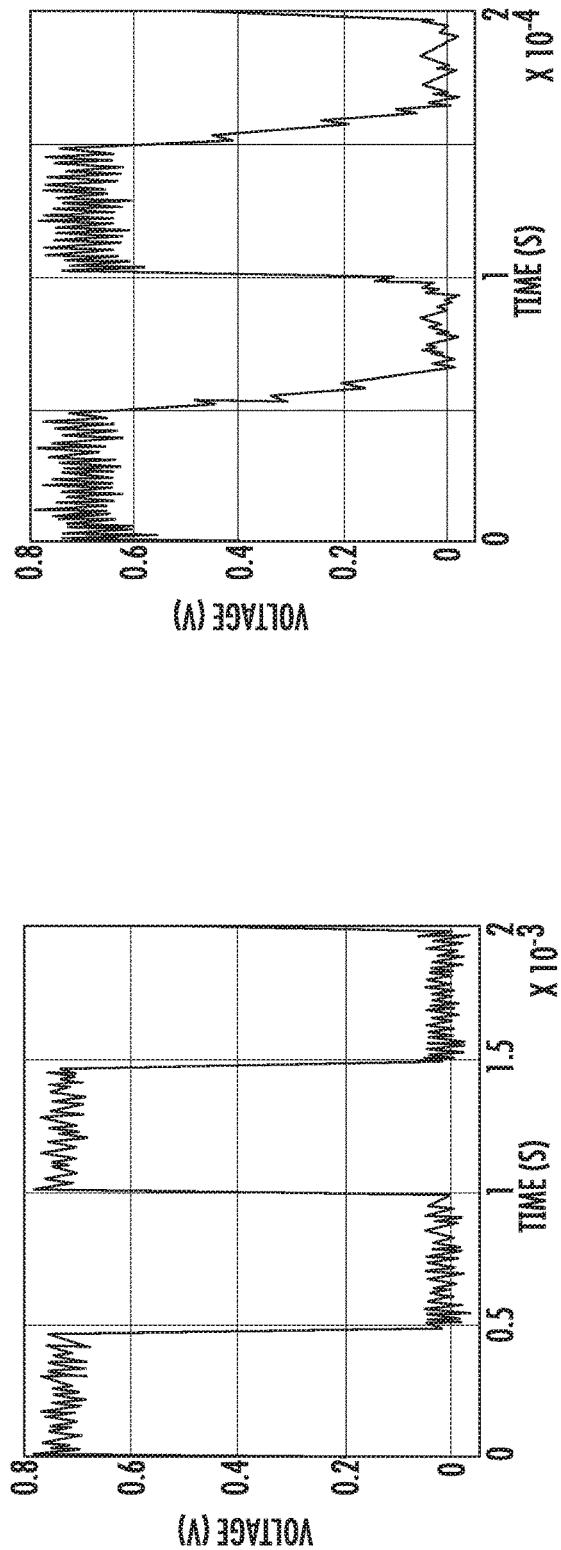
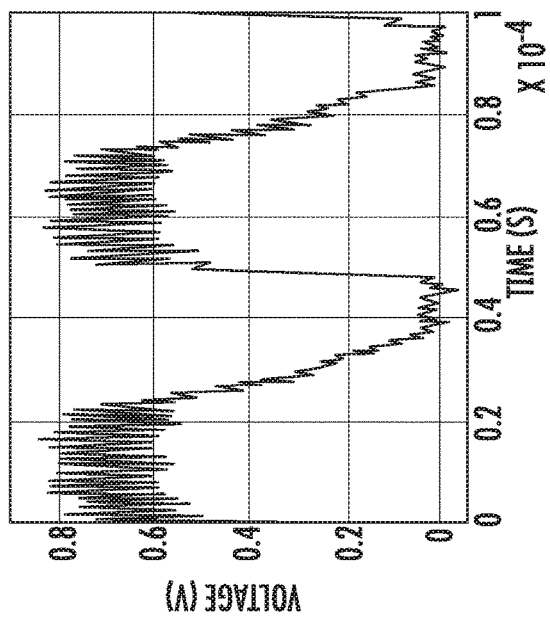
FIG. 18B1
FIG. 18B2
FIG. 18B3

WIRELESS PATCH SYSTEM FOR TRANSDERMAL, TRANSMUCOSAL AND DENTAL ELECTRICAL DRUG DELIVERY

CROSS-REFERENCE TO RELATED APPLICATION

This application claims the benefit of U.S. Provisional Patent Application Ser. No. 62/158,923, filed May 8, 2015, the disclosure of which is incorporated herein by reference in its entirety.

TECHNICAL FIELD

The subject matter described herein relates generally to transdermal, transmucosal, and dental electrical drug delivery. More particularly, the subject matter disclosed herein relates to methods and systems for delivering drug particles to a target site using a wireless patch system.

BACKGROUND

Dielectrophoresis (DEP) is the movement of particles under the influence of a non-uniform electrical field. Unlike electrophoresis (EP), in which dispersed charged particles move in a uniform (direct current) electrical field, DEP does not depend on the polarity of the field or the charge of the particles. In contrast, DEP uses the gradient of the non-uniform field and the inherent dielectric properties of particles to generate electromotive forces. Since the strength of the electromotive force depends on particle and medium properties, as well as on the applied electric field frequencies, particles can be selectively manipulated. As a result, DEP has been used to manipulate, transport, separate, and sort particles in a wide array of applications, including separating cells, stretching DNA molecules, and assembling nanocircuits. AC electrokinetics (ACEK) has been shown to deliver certain drugs into human teeth more effectively than diffusion. However, using electrical wires to power intraoral ACEK devices poses risks to patients.

The concept of a pharmacotherapeutic patch is not new in medicine or dentistry. Applications include DURAGESIC® (fentanyl transdermal system) patches, which contain a high concentration of potent Schedule II opioids to manage persistent, moderate to severe chronic pain. Other examples include estradiol transdermal patches to treat hot flashes and/or vaginal dryness, itching, and burning in menopausal women. Patches are also used to prevent osteoporosis and to whiten teeth. All these patches, however, rely on passive diffusion to reach their targets. The process is often slow and inefficient.

SUMMARY

According to some embodiments, the subject matter described herein can include a method for delivering drug particles to a target site. The method can include applying a drug delivery patch to a target site. The method can further include transmitting a signal to the drug delivery patch to power the drug delivery patch by inductive coupling, thereby motivating drug particles suspended in a fluid in the drug delivery patch towards the target site.

According to some embodiments, the subject matter described herein can include a system including a drug delivery patch and a remote power unit for the drug delivery patch. The drug delivery patch includes a substrate, an electrode integrated with the substrate, and a fluid in the substrate having drug particles suspended in the fluid. The remote power unit includes and an antenna configured to drive the antenna to emit a wireless signal to the drug delivery patch to power the drug delivery patch by inductive coupling. Powering the drug delivery patch causes the electrode in the drug delivery patch to motivate the drug particles towards a target site of the drug delivery patch.

According to some embodiments, the subject matter described herein can overcome limitations of some conventional patches by using DEP and/or alternating current electrokinetic convective vortices to load and transport drugs through skin, mucosa and into teeth. Drug flow is generated directly by inducing electromechanical effects in the fluid using an integrated interdigitated electrode. In some embodiments, the driving mechanism is due to the drug particle-fluid and particle-particle interactions under DEP and AC electrokinetics. The versatile, self-contained transdermal and intraoral drug patch transports drug particles of varying molecular weight directly into biological targets; can be used with or without matrix bands; and can be remote controlled. The integrated RF circuit is embedded in a flexible plastic substrate and is wirelessly powered by inductive coupling. After activating the patch, radio wave signals transmitted by inductive coupling are then converted into output, which provide sufficient power to drive the patch to manipulate drugs via DEP and ACEO.

In some embodiments, the systems and methods described herein can treat infection, inflammation and/or pain in situ, transporting drugs directly and noninvasively through the skin, lips and into teeth and their supporting structures. By delivering antibiotics, anesthetics, and anti-inflammatory drugs directly to specific skin and oral targets, the systems and methods described herein can reduce or even eliminate systemic side-effects and risks commonly associated with oral drug delivery and may advance the science of drug delivery by: extending targeted electro-chemical drug transport to many specific intraoral and external biological targets; improving efficacy of delivery; and negating many of the safety risks associated with some conventional patches.

A certain object of the presently disclosed subject matter having been stated hereinabove, which is addressed in whole or in part by the presently disclosed subject matter, other objects and advantages will become apparent to those of ordinary skill in the art after a study of the following description of the presently disclosed subject matter and in the accompanying non-limiting Figures.

BRIEF DESCRIPTION OF THE DRAWINGS

The subject matter described herein will now be explained with reference to the accompanying drawings, of which:

FIGS. 1A-1D illustrate a system for delivering drug particles to a target site;

FIG. 8 shows a table, Table 1, including data for dental bleaching using ACEK or diffusion;

FIGS. 18A1-18A3 and FIGS. 18B1-18B3 and FIG. 18C show the applied AM signals to the primary coil and their respective demodulated pulse signals over the IDE;

DETAILED DESCRIPTION

Figure 1C:
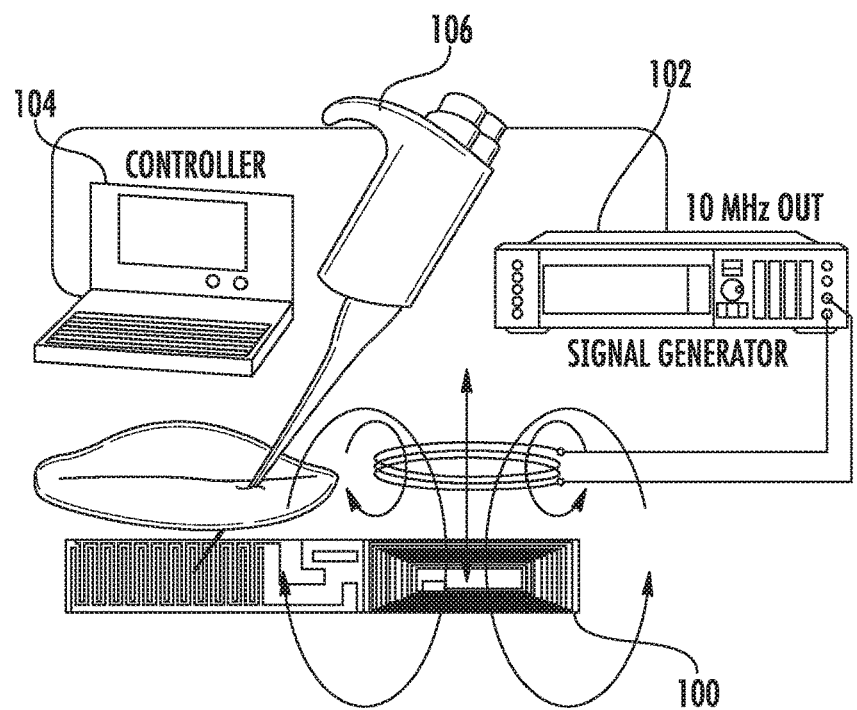

The presently disclosed subject matter will now be described more fully hereinafter with reference to the accompanying examples, in which representative embodiments are shown. The presently disclosed subject matter can, however, be embodied in different forms and should not be construed as limited to the embodiments set forth herein. Rather, these embodiments are provided so that this disclosure will be thorough and complete, and will fully convey the scope of the embodiments to those skilled in the art.

Unless otherwise defined, all technical and scientific terms used herein have the same meaning as commonly understood by one of ordinary skill in the art to which this presently described subject matter belongs. All publications, patent applications, patents, and other references mentioned herein are incorporated by reference in their entirety. Following long-standing patent law convention, the terms "a" and "an" mean "one or more" when used in this application, including the claims. The term "and/or" when used to describe two or more activities, conditions, or outcomes refers to situations wherein both of the listed conditions are included or wherein only one of the two listed conditions are included.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter. Thus, the term "about", as used herein when referring to a value or to an amount of mass, weight, time, temperature, volume, or percentage is meant to encompass variations of ±20% or ±10%, more preferably ±5%, even more preferably ±1%, and still more preferably ±0.1% from the specified amount, as such variations are appropriate to perform the disclosed method.

The term "comprising", which is synonymous with "including," "containing," or "characterized by" is inclusive or open-ended and does not exclude additional, unrecited elements or method steps. "Comprising" is a term of art used in claim language which means that the named elements are essential, but other elements can be added and still form a construct within the scope of the claim. As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole. As used herein, the phrase "consisting essentially of" limits the scope of a claim to the specified materials or steps, plus those that do not materially affect the basic and novel characteristic(s) of the claimed subject matter. With respect to the terms "comprising", "consisting of", and "consisting essentially of", where one of these three terms is used herein, the presently disclosed and claimed subject matter can include the use of either of the other two terms.

Disclosed herein are patch-based methods and systems that combine AC electroosmosis (ACE) with DEP to enhance delivery of active agents into tissues. As used herein, the term "ACEO" is synonymous to "ACE", which both refer to alternating current electroosmosis, the physical phenomenon of using AC potential to move fluids through a porous medium. ACE also has significant potential for administering precisely targeted drugs or other agents through various tissues. Electroosmosis (EO) typically refers to using DC potential to moving fluids through a porous medium. As with EO, ACEO is also based on the ion migration within a nanometer layer of charges/ions at the interfaces of electrolytes and solids (double layer). This layer of charges will migrate under electric fields tangential to the interface, and because of fluid viscosity, the ion movement carries along its surrounding fluids, leading to fluid motion.

In ACEO, the charges in the double layer are induced by AC potentials, and tangential E-fields are also from the same voltage source. Therefore, the changes of polarities in charges and field directions are simultaneous and cancelled out, maintaining steady ion migration and fluid motion. By adjusting the amplitude and frequency of AC signals, a variety of directed surface flows are produced on electrodes to manipulate and transport particles. In symmetric systems (both spatial and temporal) the resulting liquid flow is alternating in direction with a zero offset. To obtain directionality asymmetry is added either in space (by electrode geometry) or in time (by applying asymmetric AC signals).

Introduction—Drug Delivery Using an Interdigitated Electrode

Assembly Powered by Inductive Coupling AC electrokinetics (ACEK) is increasingly becoming a viable method to transport drugs directly into teeth by using an alternating current electric potential. However, a major barrier to clinical use is the reliance of such appliances on electrical wires and connectors. By using inductive coupling to power diffusion cells whose functional element is an interdigitated electrode (IDE), this obstacle can potentially be overcome.

The presently disclosed subject matter demonstrates the feasibility of using a wirelessly powered, passive and miniaturized patch for enhanced drug delivery, which eliminates the need for wire attachments and concerns related to electric leakage. The IDE assembly uses inductive coupling to drive the functional elements, which provides an aspect of the presently disclosed subject matter. After characterizing the electrode and electrical design, the functionality of the patch is validated in a common dental application in which the whitening of human teeth is known to be significantly greater compared to diffusion, when 35% carbamide peroxide is delivered by a similar diffusion cell that is powered by a function generator.

The functionality of the device is validated further by eliciting ACEK behavior of other drugs in non-uniform electrical fields at various frequency ranges wirelessly. After optimizing the frequencies for particle translation under DEP or biased ACEO, the patch comprising a receiving coil, demodulation circuit and an IDE array is used to trap, manipulate, and translate latex, tetracycline, acetaminophen, benzocaine and lidocaine particles. Drug particle movements at various frequencies are captured and analyzed with light microscopy in real time.

Example Methods and Materials

FIGS. 1A-1D illustrate a representative system for delivering drug particles to a target site. The system includes a drug delivery patch 100, a signal generator 102 including an antenna and a circuit for driving the antenna, a control system including one or more processors and memory storing instructions for controlling the signal generator 102, and device 106 for supplying a fluid to the patch having drug particles suspended in the fluid. FIGS. 2A-2D illustrate example dimensions of the patch 200, an example receiving coil 206 and demodulation circuit integrated into a flexible layer 210 with the user of surface mounted devices 202, and a circuit diagram 204 of the demodulation circuit.

The ACEK electrode patch (FIG. 1A, built on a flexible printed circuit board (PCB), has a compact design with a receiving coil and an IDE (208 in FIG. 2B) integrated into an area less than a penny (FIG. 1B) that is wirelessly powered through inductive powering. The receiving coil 206 and demodulation circuit (FIG. 2B) are integrated into the flexible PCB 210 with minimal volume at low cost with the use of surface mounted devices 202. An amplitude modulation (AM) scheme is used for transmission of low frequency AC signals to the wireless assembly. An envelope detector circuit 212 located immediately after the receiving coil 206 removes the high frequency carrier signal and delivers the low frequency modulating signal to the IDE 208, which is expected to motivate drug particles towards target sites. The output signal of the dental patch is externally programmable by adjusting the modulating signal, so that the IDE can operate at optimally tuned low voltage AC signals to induce drug movement into intraoral biological structures (FIG. 1C). The flexible PCB electrode has a geometry and configuration that can be used transdermally as well as for intraoral applications.

Figure 1D:
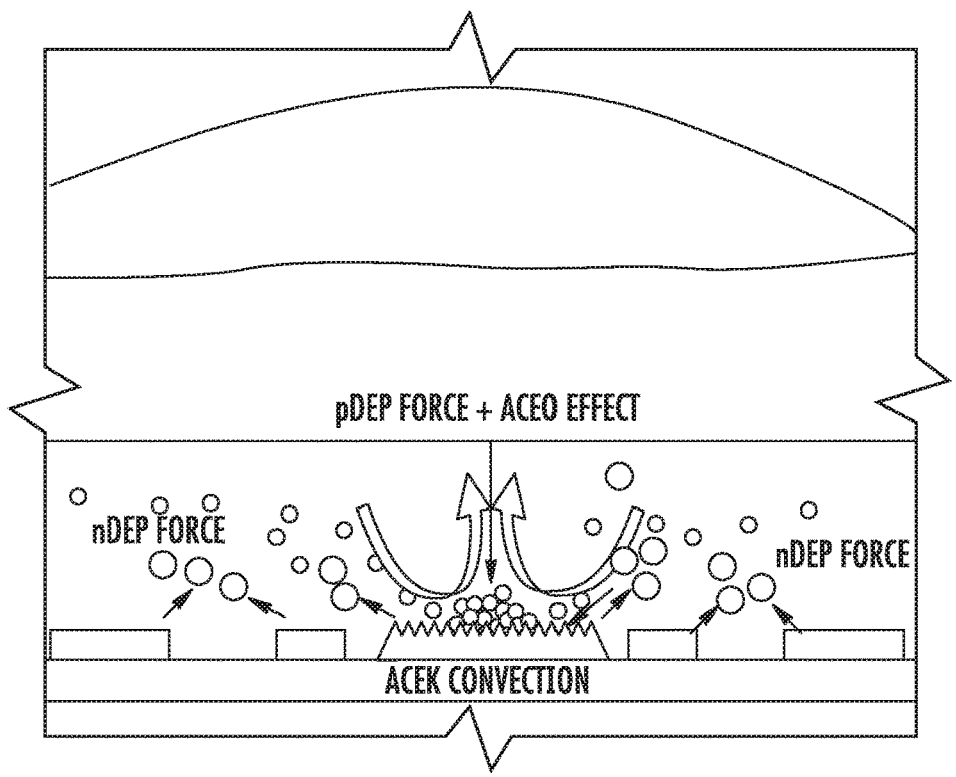

A schematic overview of the operating principle, device structure and the mechanism used by the patch for ACEK drug delivery is shown in FIGS. 1A-1C. The miniaturized patch uses ACEK as an effective method to deliver drugs to specific target sites. ACEK effects can induce directional particle movement and can, therefore, be used to accelerate the transport of medicine to specific target sites (FIG. 1D). Moreover, as the device is passive, its required low frequency AC signal is supplied by transmission of an AM signal through inductive powering. As shown in FIG. 1C, an appropriate AM signal is applied to the transmitter coil (214 in FIG. 2B) that acts like an antenna to wirelessly transmit an AM signal onto the receiving coil on the patch. The received AM signal is then demodulated to yield the desired ACEK signal. The ACEK signal then activates the IDE to induce particle movement towards the tooth surface or other surface.

Figure 2A:
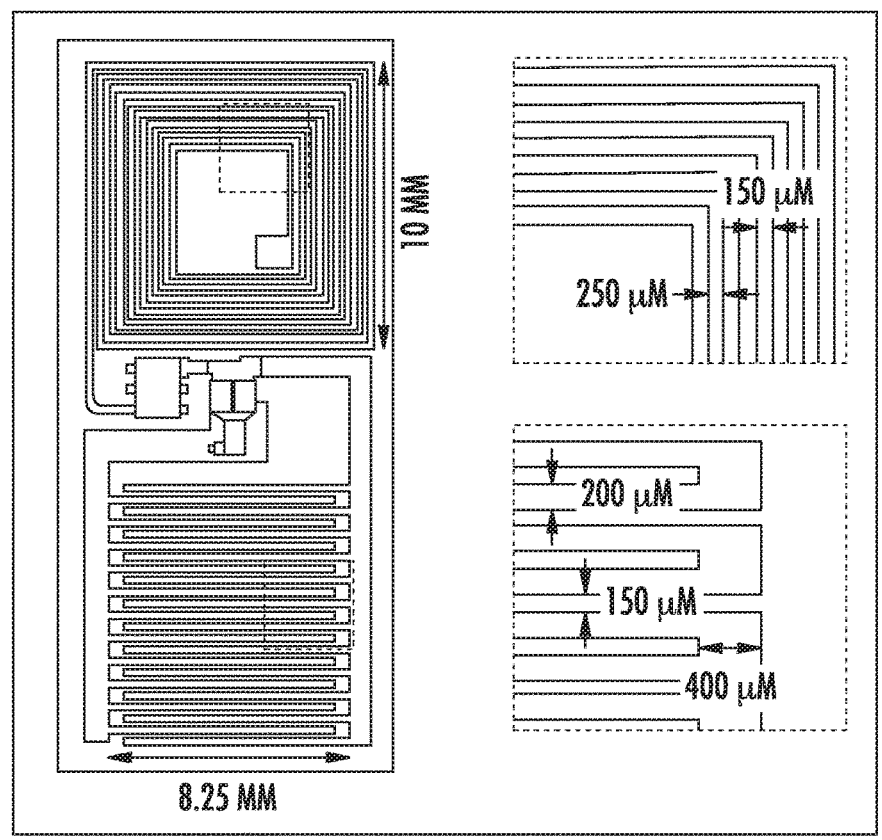
FIGS. 2A-2D illustrate example dimensions of the patch, an example receiving coil and demodulation circuit integrated into a flexible layer with the user of surface mounted devices, and a circuit diagram of the demodulation circuit.
Figure 2B:
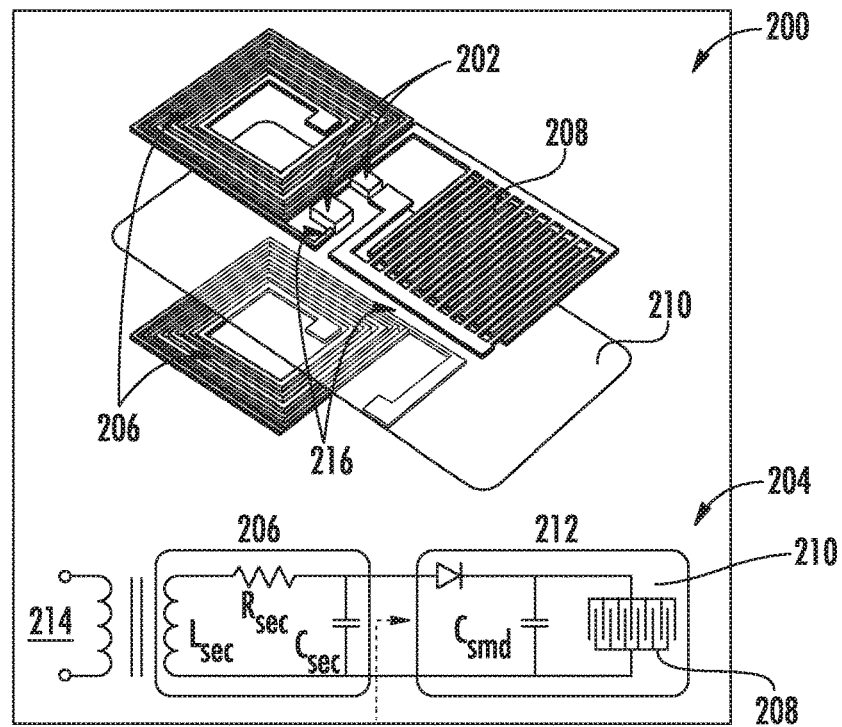
Figure 2C:
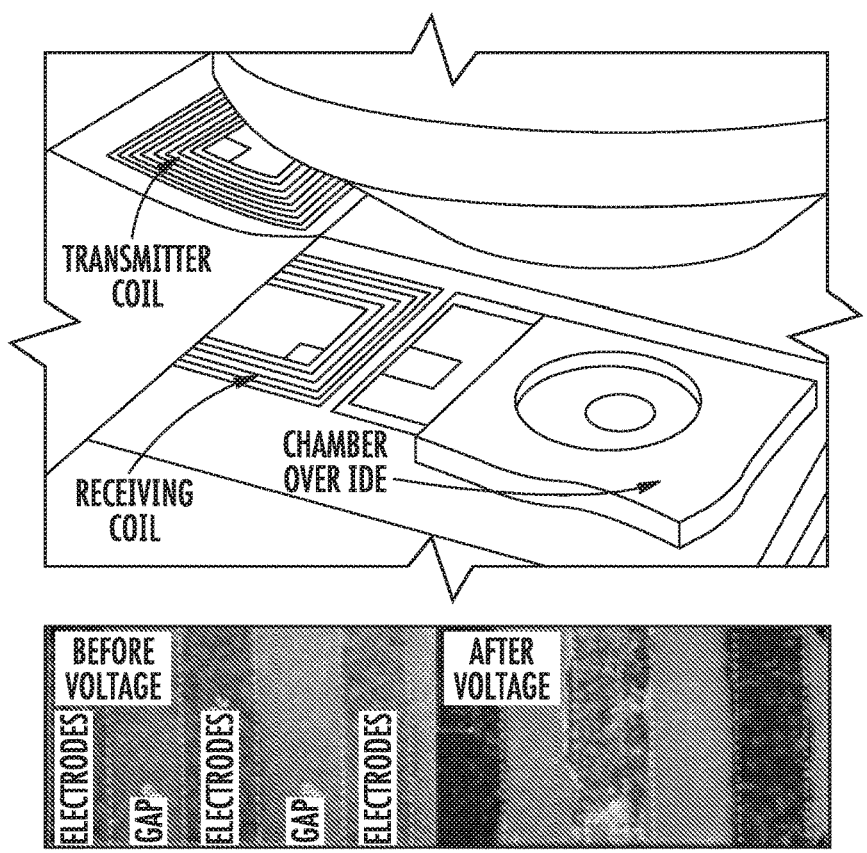
Figure 2D:
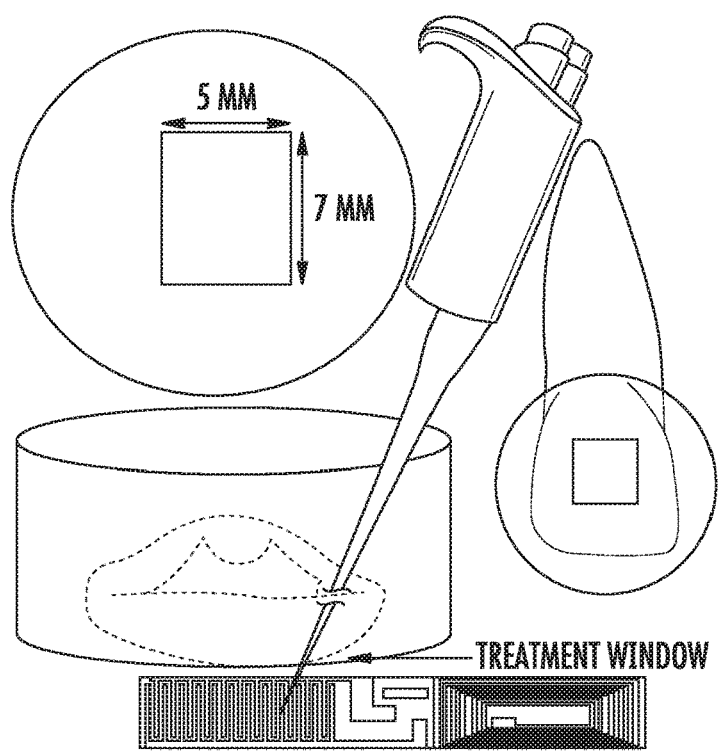

By transmitting the AM signal from a transmitter coil, the receiving coil receives the AM signal through an inductive link. The received AM signal is demodulated by surface mount devices (a schottky diode and a capacitor). The low frequency biased AC signal required for ACEK excitation is then delivered to the IDE. The carrier and modulating signal frequency of the AM signal is determined based on the resonance frequency of the receiving circuit and the frequency range of ACEK, respectively. As shown in FIG. 2C, carboxylate-modified microspheres are levitated by vortices induced by biased ACEO effects. In some embodiments, the front side of the patch will be in contact with the tooth/gum site at which the drug is intended to be delivered (FIG. 1A). The IDE will be loaded with a solution containing drug particles. As a result of ACEK effects, the drug particles will, in turn, be transported to tooth/gum sites (FIG. 1D).

The interdigitated electrode can be of variable dimensions (smaller or bigger than the one fabricated) and vary in number of electrode finger pairs. Similarly, the receiving coil can be configured with variable turns and dimensions. The receiving coil is presented here in a layout showing the coil juxtaposed and attached to the electrode using surface mounted devices, but it can also be configured such that the receiving coil is superimposed over the electrode or in any other appropriate configuration.

Pyralux 8525R (DuPont, Wilmington, Del., United States of America), a double-sided flexible copper cladded polyimide film, is used for the fabrication of the device. The fabrication steps are as follows; 1) the film is taped on a supporting wafer and cleaned with acetone and methanol first and then spin coated with AZ1518 positive photoresist. 2) Photoresist is developed for the desired pattern by exposing it under UV light through a transparency mask for 8 seconds and then developed in developer solution. 3) The exposed copper is then chemically etched in a ferric chloride solution for approximately 25 minutes to yield an alternating pattern and rinsed thoroughly under running de-ionized (DI) water for 5 minutes. 4) Steps 1-3 are repeated to yield the receiving coil on the back side of copper film. 5) Gold electroplating is done in order to coat the IDE surface with a very thin layer of gold. 6) Through holes (216 in FIG. 2B) are drilled and electroplated to make connections between back and front side coils and between back coil and IDE across the polyimide film, as shown in FIG. 2B. 7) The device is ultrasonically cleaned in acetone and DI water for 5 minutes each, respectively. The electrode is cleaned in RIE plasma cleaner to remove any organic residues. 8) External electronic components (e.g. SMD diode and capacitor) are soldered on. A finished patch is shown in FIG. 1B with a penny for size comparison.

The front side of the dental patch can comprise surface mount devices and metalized traces to create the front side coil and IDE (FIG. 2A), and the back side can comprise metalized traces for the creation of a coil (FIG. 2B). The front and back side metallization are connected in series through a hole in the middle of the flexible layer and construct the receiving coil. The outer end of the front coil is connected to the anode of the SMD schottky diode. The cathode of the diode is connected to the SMD capacitor and one end of IDE. The outer end of the back coil is connected to the other end of the IDE and capacitor through a hole in the flexible layer.

IDE and coil impedance data were acquired using a high precision impedance analyzer (Agilent 4294A, Agilent Technologies, Santa Clara, Calif., United States of America) and the data were recorded through its LAN port onto a computer using software Data Transfer V3.0 (SEKONIC, North White Plains, N.Y., United States of America). Electrochemical impedance spectroscopy (EIS) analysis, which is a well-established method for characterizing an electrolytic cell, is used to characterize the IDE. In EIS method, an electrical circuit can be developed to represent an electrochemical cell's behavior over a range of frequencies. In some embodiments, the IDE is composed of 27 fingers each with dimension of 150 µm (width)×7850 µm (length)×18 µm (thickness). In some embodiments, the spacing between fingers is 250 µm (FIG. 2A).

Figure 3A:
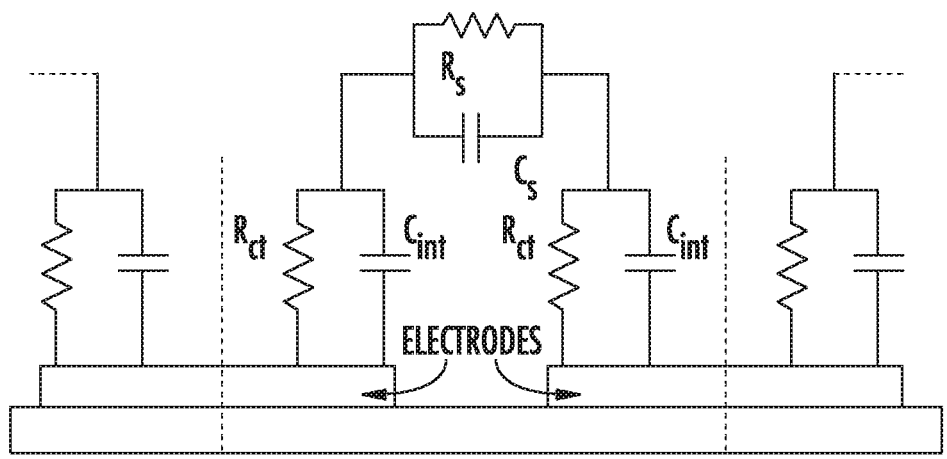
FIGS. 3A-3D illustrate an equivalent circuit model for two nearby fingers when the IDE is immersed in solution, measure and fitted impedance spectra for two nearby fingers, a schematic representation of IDE equivalent circuit model, and an equivalent circuit model of the IDE.
Figure 3B:
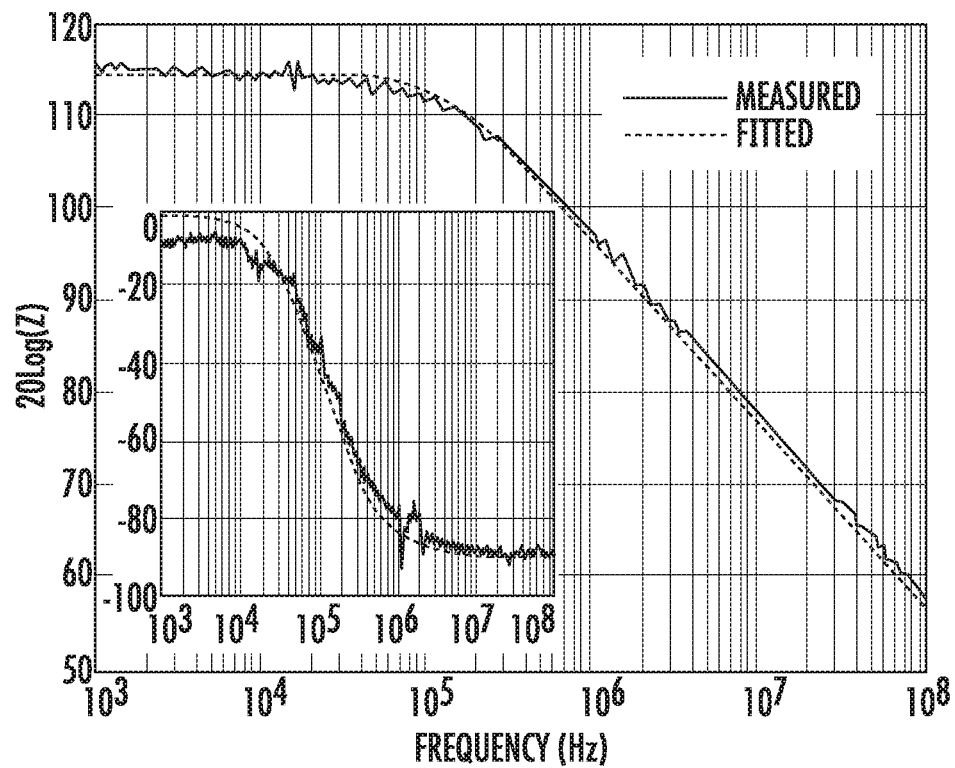
Figure 3C:
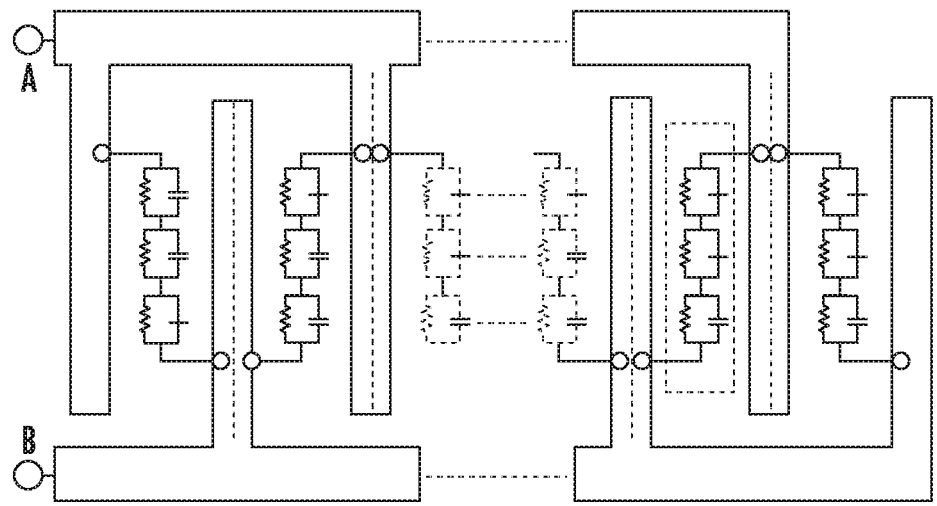
Figure 3D:
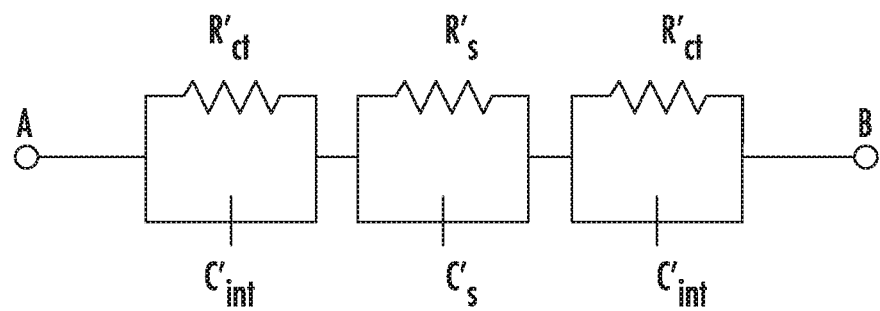
Figure 4A:
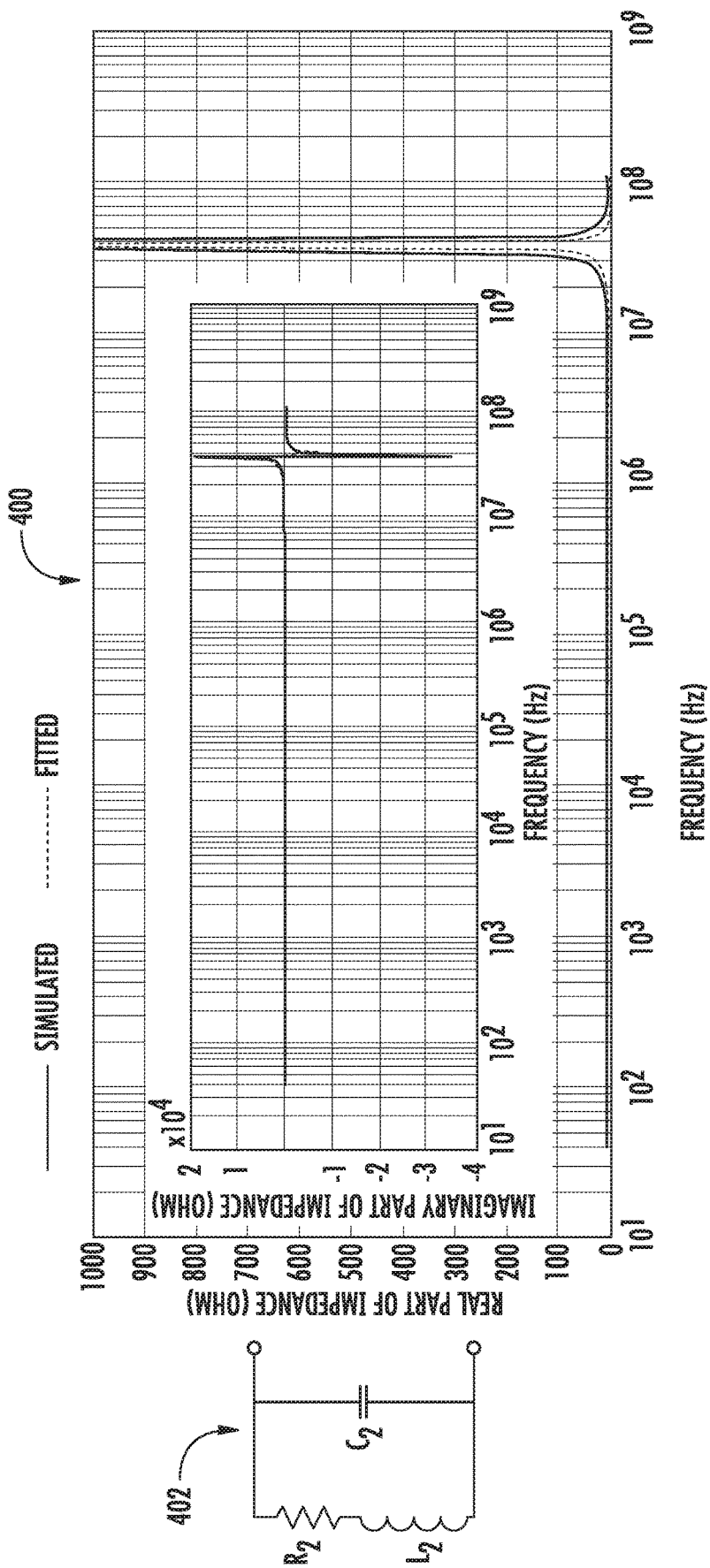
FIGS. 4A-4C illustrate an equivalent circuit for the receiving coil with the measured and fitted impedance data for the receiving coil, the equivalent circuit model of the patch used for AM signal transmission and demodulation shown with measured output levels as a function of frequency, and output voltages levels at modulating signal frequencies.
Figure 4B:
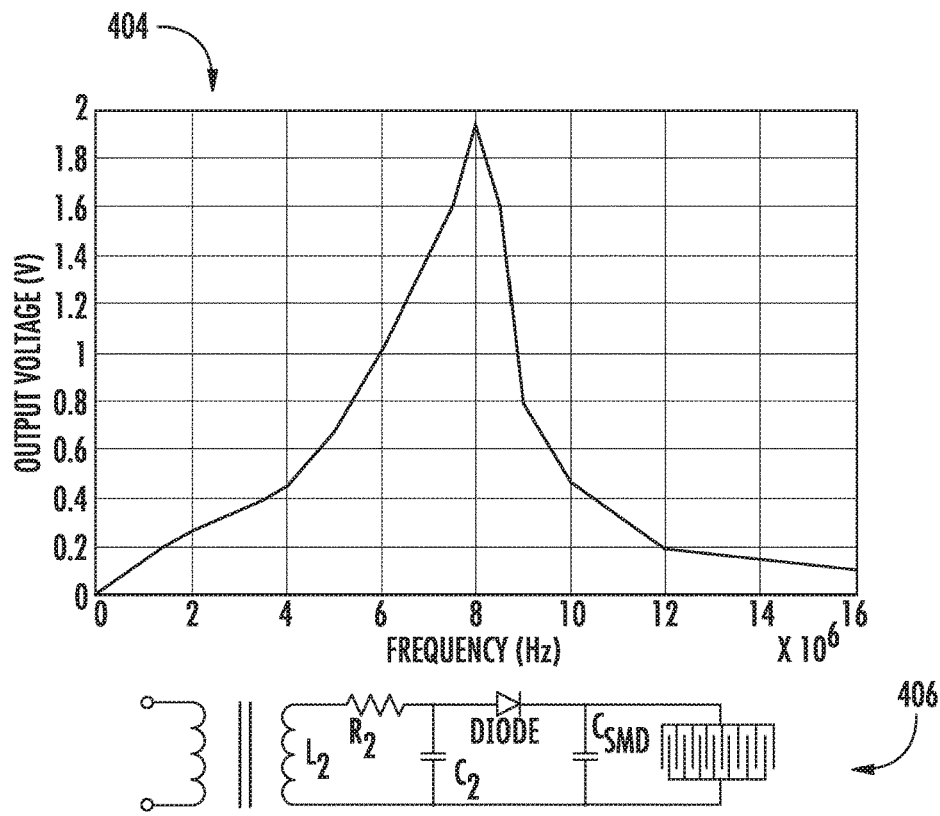
Figure 4C:
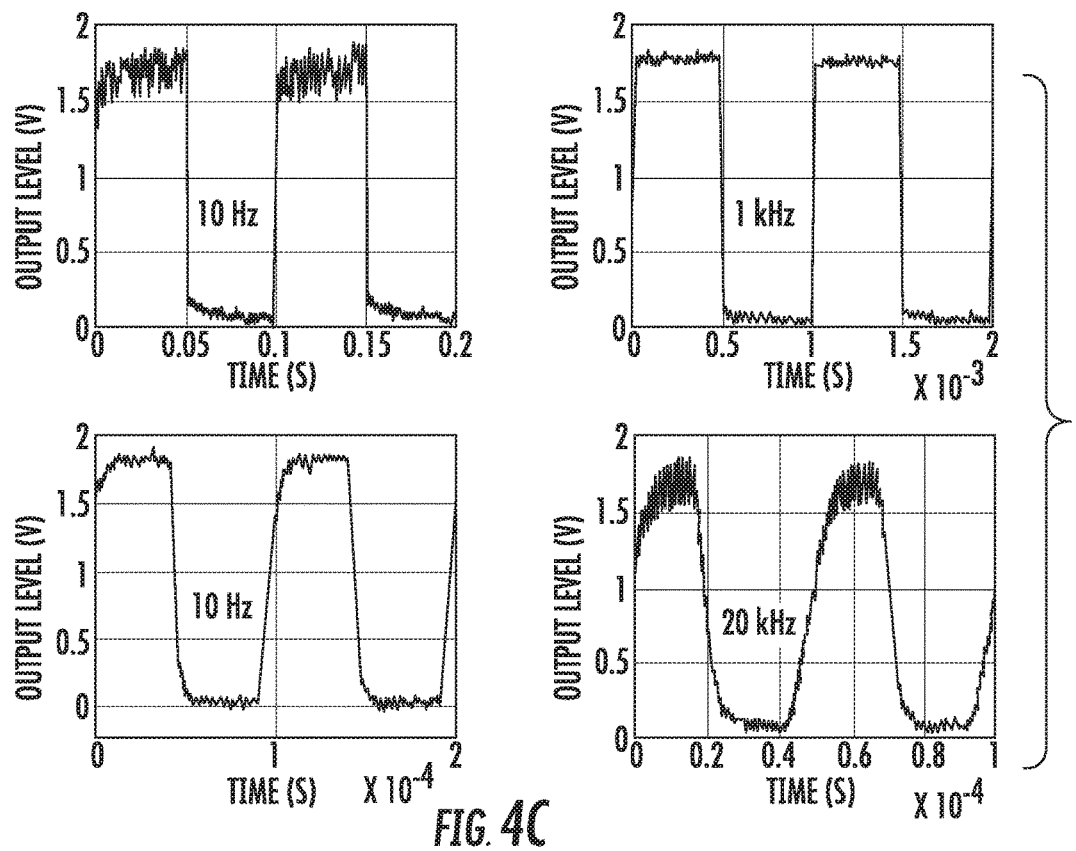

FIGS. 3A-3D illustrate an equivalent circuit model for two nearby fingers when the IDE is immersed in solution, measure and fitted impedance spectra for two nearby fingers, a schematic representation of IDE equivalent circuit model, and an equivalent circuit model of the IDE. FIGS. 4A-4C illustrate an equivalent circuit 402 for the receiving coil with the measured and fitted impedance data 400 for the receiving coil, the equivalent circuit model 406 of the patch used for AM signal transmission and demodulation shown with measured output levels as a function of frequency, and output voltages levels at modulating signal frequencies. The inset in FIG. 4A is the imaginary part of the impedance.

When the IDE is immersed in solution, the impedance between two nearby fingers can be estimated by a network of the interfacial capacitor and charge transfer resistor in the electrode/electrolyte boundary and the electrolyte resistance and capacitance in the bulk solution (FIG. 4A). In FIG. 4A, $C_{int}$ is interfacial capacitance, $R_{ct}$ is charge transfer resistance, $R_s$ is electrolyte resistance, and $C_s$ is electrolyte capacitance. The interfacial capacitor is caused by the electric double layer (EDL). In order to characterize and extract a circuit model for the IDE, the equivalent circuit model for two nearby fingers immersed in solution (FIG. 3A) is extracted by curve fitting of measured impedance data. FIG. 3B shows measured and fitted impedance data for two neighboring fingers. By the use of the impedance network in FIG. 3A, curve fitting is done for two neighboring fingers and the circuit parameters are extracted as follows $C_{int}$=46 nF, $R_{ct}$=260 kΩ, $C_s$=2.3 pF, and $R_s$=535.6 kΩ. As shown in FIG. 3C, the IDE is composed of 25 parallel connections of two neighboring fingers. Hence, by the use of electrical circuit analysis methods the circuit parameters of the final IDE shown in FIG. 4(d) can be calculated as; $C'_{int}$=1.2 µF, $R'_{ct}$=10 kΩ, $C'_s$=60 pF, and $R'_s$=20.6 kΩ.

In some embodiments, the receiving coil comprises a series connection of the front and back side coil. A two-sided configuration considerably increases the inductance of the receiving coil without increasing patch dimension (FIG. 2B). For a leaky inductive link as used here, a higher inductance will allow the system to operate with a lower carrier frequency, which will facilitate the development of a portable system. The two coils are of the same dimensions, with representative outer and inner diameter of 5 mm and 2.25 mm, respectively. In some embodiments, the width of metal traces is 150 µm with a spacing of 250 µm between each turn (FIG. 2A). The equivalent circuit model of the receiving coil is shown in FIG. 4A. An inductor (Lsec) and a resistor (Rsec) in series account for coil self-inductance and DC resistance, and a capacitance (Csec) accounts for interwinding capacitance coupling between the copper lines through the walls, air and flexible layer ($\varepsilon\_air$=1, $\varepsilon\_flex$=3.4). The real and imaginary part of the coil impedance (FIG. 4A) is first measured and then, by the aid of curve fitting, the parameters of equivalent circuit model are extracted. The value of L2, R2, and C2 is extracted as 2.3 µH, 3.4Ω, and 7.67 pF, respectively.

In order to study the functionality of the patch in terms of a demodulation circuit and ACEK effect, a very simple set-up was constructed which is shown in FIG. 2C. The experimental set-up includes the dental patch, an optical microscope, AC waveform generators, a digital oscilloscope and some probe connectors. A microchamber was sealed over the IDE to hold the solution (FIG. 2C). FlouSphere carboxylate-modified microspheres with diameter 1.1 µm (Molecular Probes, ThermoFisher Scientific, Waltham, Mass., United States of America) were mixed with DI water and used in the experiment to demonstrate the biased ACEO effect. The movement of particles was observed by an optical microscope NIKON ECLIPSE LV100 (Nikon Instruments, Inc., Melville, N.Y., United States of America) and the images from the microscope were acquired by a Roper Scientific (Tucson, Ariz., United States of America) digital camera and subsequently transferred to a computer. An AM signal with the amplitude of 10 V was applied to the primary coil. The AM signal applied to the primary coil was generated by two Agilent Arbitrary Waveform Generators (model 33220A). The carrier signal frequency was 8 MHz. The separation between primary and secondary coil is 10 mm. An Agilent Mixed Signal Oscilloscope (model MSO6012A) was used to record the demodulated signal. The demodulated voltage waveforms over the IDE are single polarity pulses as shown in FIG. 4C, which demonstrate successful demodulation of AM signals for a range of modulating signal frequencies. The frequency of the modulating signal was continuously swept in order to find an appropriate frequency at which ACEK effect occurs. The ACEO effect was subsequently observed at frequencies around 10 kHz. Particle distribution resulting from the biased ACEO effect is shown in FIG. 1D.

The ACEK effect on Tetracycline, Acetaminophen, Benzocaine and Lidocaine was studied. The experiment demonstrates the response of tetracycline (antibiotic), acetaminophen (analgesic), benzocaine and lidocaine (anesthetics) particles to induced ACEK effects after applying an AC electric field to the diffusion cell at various frequencies using the set-up in the previous experiment. 250 mg tetracycline and 325 mg acetaminophen powders were dissolved in deionized water (DI water) to form 25 µg/ml and 32.5 µg/ml aqueous solutions respectively, then mixed with a Vortex Mixer (ThermoFisher Scientific, Waltham, Mass., United States of America) and filtered. 1.8 ml 2% lidocaine and 1 ml 5% benzocaine were diluted with DI water to form 36 µg/ml and 50 µg/ml solutions respectively. 5 ml of the top layers of each drug sample was then transferred to five 1 ml vials, containing particles 1-5 μm diameter that were used in the experiment. A 50 μl sample of each drug was placed in the holder on the IDE assembly (FIG. 2C) and the response of each drug to the applied electrical field was then studied under various frequency and voltage conditions. Sweeping through frequency ranges 1 MHz to 20 MHz in 500 kHz intervals, then 1 MHz to 100 Hz, drug particle movements at various frequencies are captured and analyzed with light microscopy.

The use of the system for dental whitening with bleaching gel applied topically or with ACEK was studied. The experiment aims to validate the effectiveness of the diffusion cell powered by inductive coupling in a common dental application that has been shown to be enhanced with a similar diffusion cell powered by a function generator. Thirty unrestored human maxillary central incisors, free of visible cracks and caries, were used for this study. After sectioning off the roots, the anatomic crowns were embedded in acrylic molds, leaving a 5 mm×7 mm treatment window exposed on the facial enamel surface (FIG. 2D), then sanded with 400, 600, and 800 grit silicon carbide paper to achieve a flat surface, and polished with 1.0 and 0.5 μm alumina suspensions. The teeth were then randomly divided into two equal groups. Baseline L* values (a measure of the psychometric lightness from black to white) were determined for each specimen with a spectrophotometer (Konica Minolta, Tokyo, Japan) in both specular component included (SCI) and specular component excluded (SCE) measuring geometries, at visible wavelength spectrum 380-780 nm, at three different spots across the enamel surface in triplicate and then averaged. Half of the samples were then treated with 35% carbamide peroxide bleaching agent (Opalesence, Ultradent, South Jordan, Utah, United States of America) applied to the enamel surface topically (diffusion) for twenty minutes at room temperature, while the remaining samples were placed on the diffusion cell powered by inductive coupling and treated with bleaching gel by ACEK at frequency 1,200 Hz, at 5 Vpp. After twenty minutes, the samples were wiped with a Kimwipe™ tissue to remove residual gel, and SCI and SCE L* values were measured with a spectrophotometer at three different spots across the treated enamel surface in triplicate and then averaged.

Whitening was measured as changes between baseline and post-treatment L* values according to the CIE 1976 L*a*b* color scale relative to the standard illuminant D65 in the transmittance mode. The L* value determines the psychometric lightness from black to white. The L* values were obtained in both specular component (SCI) and specular component excluded (SCE) measuring geometries. The specular component is the reflected light from the tooth surface such that the angle of reflection equals the angle of incidence. In general, the SCE mode relates to diffuse illumination, while SCI measurements represent total illumination which includes diffuse and the specular component.

Results

The circuit model used for receiving and demodulating the AM signal is shown in FIG. 4B, in which the receiving coil on the patch is represented by its equivalent circuit including parasitic elements of resistance and capacitance. The input signal for the primary coil is an AM signal. The modulating signal is a pulse waveform whose frequency is determined by the frequency range at which ACEK can occur and the carrier is a sinusoidal signal. The secondary coil intercepts the AM modulated signal transmitted by the primary coil. A passive envelop detector composed of a diode, a capacitor, and the IDE demodulates the AM signal. The circuit shown in FIG. 4B has a resonance response arising from the receiving coil inductance and the SMD capacitance. At the resonance, the output voltage over the IDE will be at maximum. Hence, for dental patch applications, it is more efficient to set the carrier signal's frequency to the resonance peak of the link. Based on the circuit parameters extracted for the receiving coil and the IDE, the resonance peak for the patch circuit is calculated to be 8 MHz, which, in turn, will be the frequency of the carrier signal.

FIG. 4B shows the output levels of the system for different frequencies of the carrier signal. The IDE is loaded with drug solution and the dental patch is located 10 mm away from the transmitter coil. As FIG. 4B suggests, in order to have maximum output, the frequency of carrier signal needs to be set at 8 MHz. As previously mentioned, the frequency of the modulating signal determines the frequency of the ACEK signal. Since the ACEK effect occurs at a frequency range and not at a single frequency, the system tolerance on the variation of modulating signal's frequency was also studied and the measured demodulated outputs are shown in FIG. 4C. An Agilent Mixed Signal Oscilloscope (model MSO6012A) was used to record the demodulated signal. The demodulated voltage waveforms over the IDE were single polarity pulses as shown in FIG. 4C, which demonstrate successful demodulation of AM signals for a range of modulating signal frequencies.

The applied voltage to the primary coil alongside the demodulated voltage waveform over the IDE, is shown in FIG. 4C. FIG. 2C shows particle distribution inside of the solution before and after applying the AM signal. Before applying the AM signal, particles are randomly distributed inside the solution. After applying the AM signal, particles are lined-up between the electrodes and levitated. In the attached film, the counter-rotating vortices induced by fluid movement and the biased ACEO effect continually transport the particles away from the electrode and demonstrate in principle, how the long range motion of drug particles can be directed towards a tooth surface or other intended target. In other studies where fluoride was applied to teeth with an IDE setup powered by a function generator, this same ACEK mechanism was shown to effectively promote the deposition of fluoride particles into tooth enamel and ultimately enhance its uptake. The results of the current experiment suggest that ACEK effects can also be induced by IDE devices that are powered by inductive coupling.

DEP and ACEO behavior of tetracycline and acetaminophen particles was observed throughout the entire experiment, both of which is frequency dependent. An AC electrothermal (ACET) effect with low velocity was also observed for both drugs at frequency range 100 kHz to 1 MH, which eventually tapered off to zero at 5 MH. No DEP effect was observed with either drug at this frequency range or from 50 kHz to 100 kHz. Upon decreasing the applied frequency below 50 kHz, the particles started gathering along the electrode edges indicating positive DEP (pDEP). Although the velocity of flow increased as well, the trapping effect became more obvious in the frequency range 500 Hz-10 kHz. Strong ACEO was also observed at frequencies between 500 Hz to 10 kHz.

FIGS. 5A-5D show example detection areas for tetracycline particles and acetaminophen particles. FIGS. 6A-6D show measured frequency responses of the conductivity of tetracycline and acetaminophen.

Figure 5A:
FIGS. 5A-5D show example detection areas for tetracycline particles and acetaminophen particles.
Figure 5B:
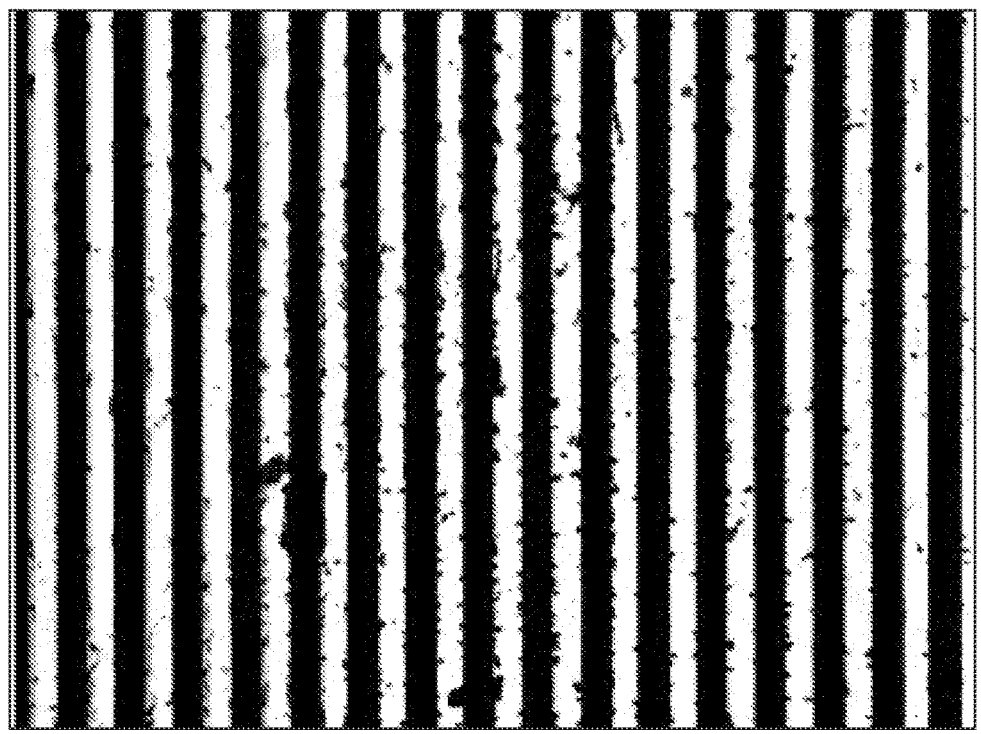
Figure 5C:
Figure 5D:
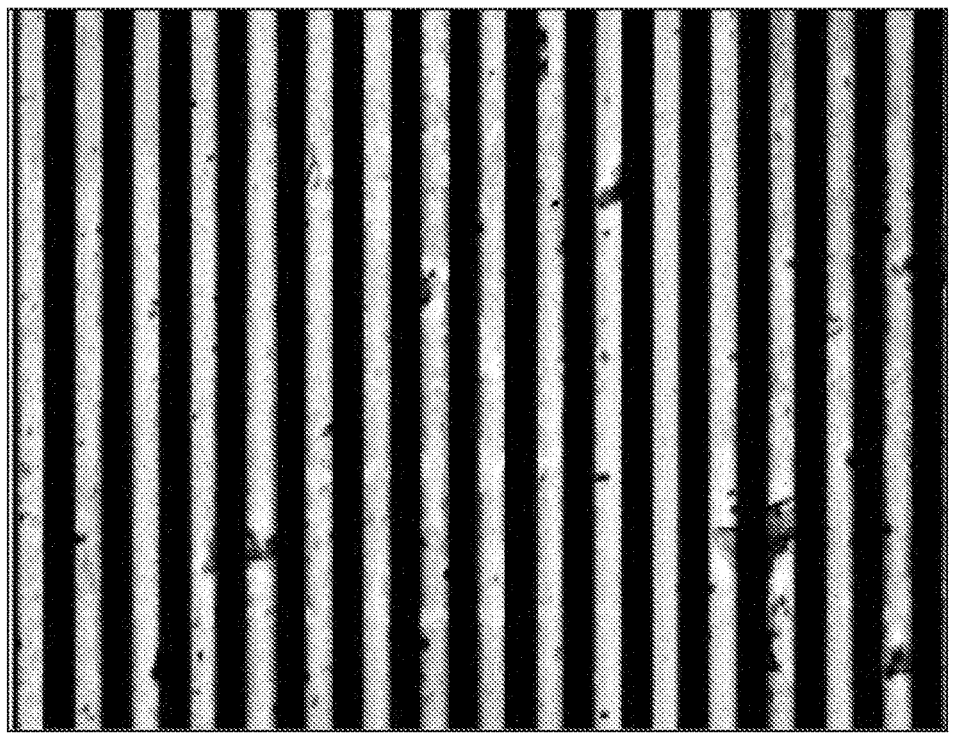

FIGS. 5A and 5B show tetracycline particles before and after pDEP trapping after 60 seconds at frequency 5 kHz, 5 Vpp. FIGS. 5C and 5D show the acetaminophen particles before and after pDEP trapping at frequency 5 kHz, 5 Vpp. Conductivity data, collected for tetracycline and acetaminophen after measuring the frequency response of the conductivity of tetracycline and acetaminophen particles with an Agilent impedance analyzer (FIGS. 6A-6D), correlate with the fact that pDEP was observed with both drugs at frequencies between 500 Hz to 10 kHz. No negative DEP (nDEP) was detected at any frequency range for either drug. As it is generally rare to observe nDEP in DI water, the lack of a nDEP effect reflects the higher conductivity of the drug particles with respect to the conductivity of DI water at every frequency.

Figure 7A:
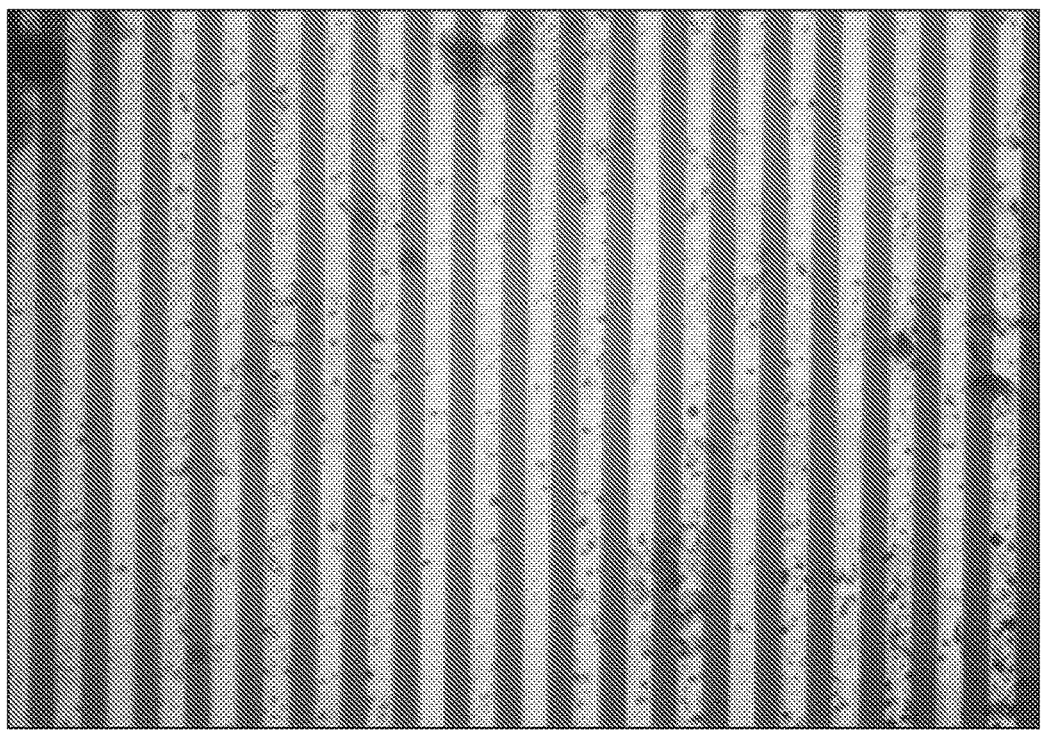
FIGS. 7A-7D show example detection areas for benzocaine and lidocaine particles.
Figure 7B:
Figure 7C:
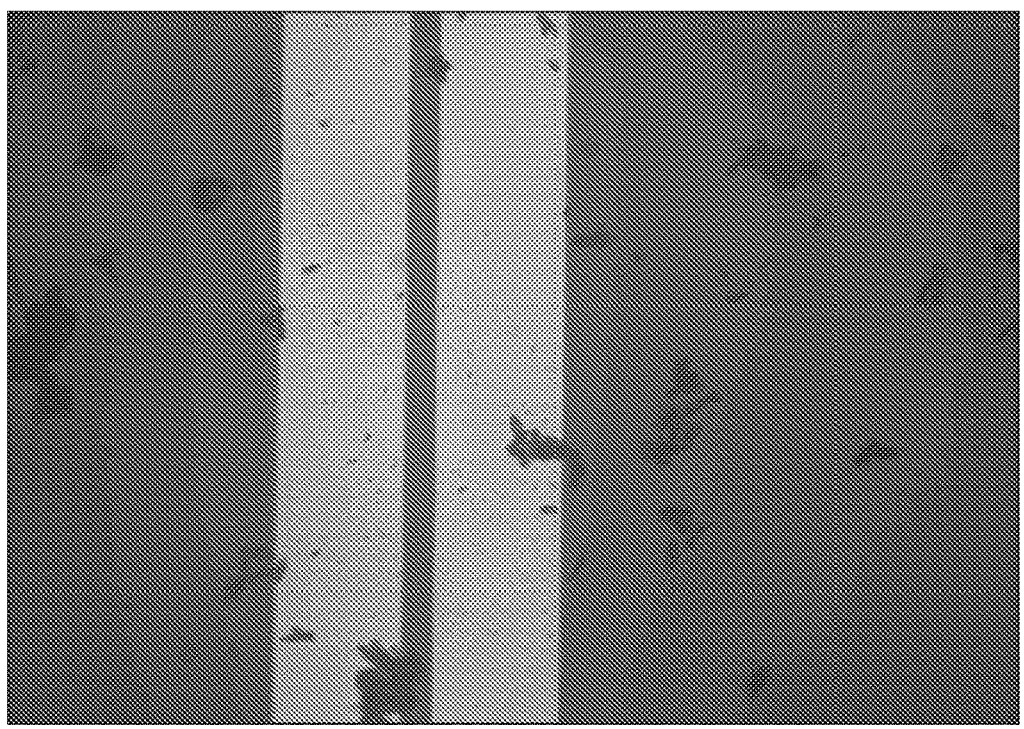
Figure 7D:
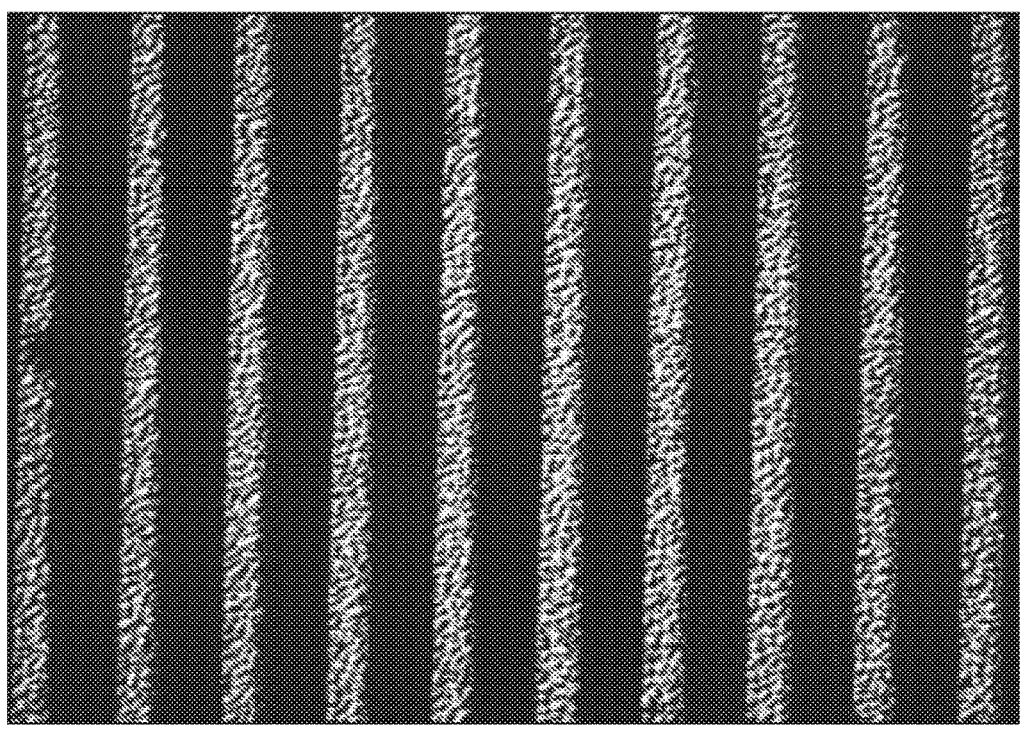

FIGS. 7A-7D show example detection areas for benzocaine and lidocaine particles. FIG. 7A shows pDEP trapping and FIG. 7B shows ACEO conditions for benzocaine. Final pDEP trapping and ACEO conditions for lidocaine are shown in FIGS. 7C-7D.

In comparison to tetracycline and acetaminophen, the visualization of benzocaine and lidocaine particles was much more tedious and rendered the observation of ACEK effects more difficult. Nonetheless, pDEP and ACEO were observed at the 500 Hz to 10 kHz frequency range, although at higher electric fields. FIGS. 7A-7D shows the final pDEP trapping and ACEO condition for benzocaine and lidocaine at frequency 1 kHz, 15 Vpp and frequency 500 Hz, 10 Vpp respectively. The brightness and contrast of FIG. 7D have been modified relative to the other images in order to render the lidocaine particles more visible to the reader. No nDEP or ACET effects were detected with either anesthetic at any frequency range during the experiment.

FIG. 8 shows a table, Table 1, including data for dental bleaching using ACEK or diffusion. The average change in whitening after bleaching with ACEK or diffusion as measured by spectrophotometer is shown in Table 1. SCI and SCE L* readings in the diffusion group were significantly higher than baseline readings. The average increase in SCI and SCE L* in the diffusion group was 0.987 (±0.213) units and 0.904 (±0.187) units respectively. SCI and SCE L* readings in ACEK treated teeth were significantly higher than the diffusion group (ANOVA/Student-Newman-Kouls post hoc, P<0.01). The average increase in SCI and SCE L* values of teeth treated with ACEK was 2.217 (±0.244) units and 1.751 (±0.246) units respectively. Significantly increased whitening was found with ACEK compared to passive diffusion (paired t-test, P<0.01).

Figure 9A:
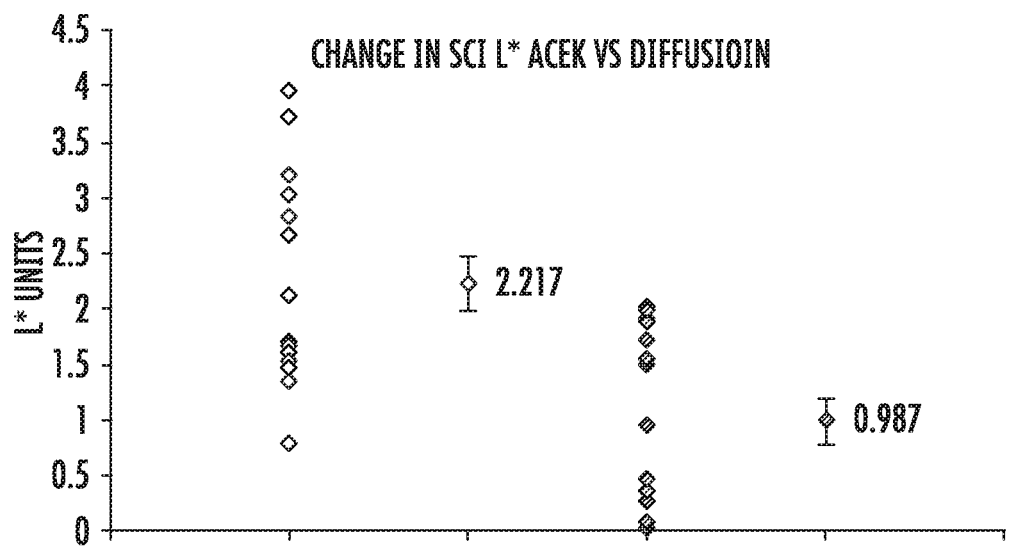
FIGS. 9A-9B show scatter plots showing the change in SCI and SCE L* values of teeth treated with ACEK vs. diffusion.
Figure 9B:
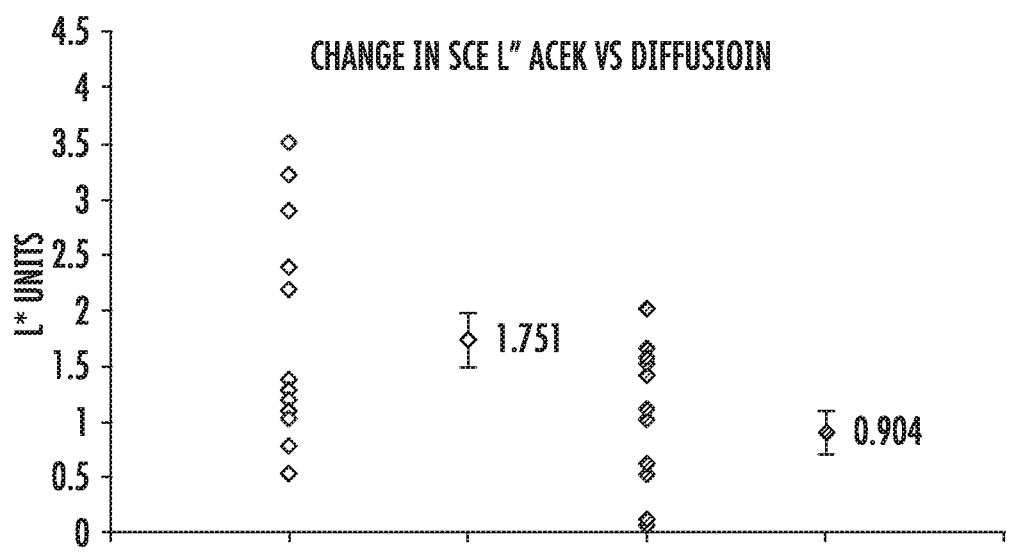

FIGS. 9A-9B show scatter plots showing the change in SCI and SCE L* values of teeth treated with ACEK vs. diffusion. Compared to diffusion, ACEK increased SCI and SCE whitening by 215% and 194% respectively, increasing SCI and SCE L* values on average by 1.230 and 0.847 units respectively. On average, the ACEK group demonstrated two times more whitening than the diffusion group after the allotted treatment time.

Discussion

The teeth in the current study were not artificially stained and whitening was measured relative to each tooth sample's natural state of intrinsic and/or extrinsic staining. Both intrinsic and extrinsic staining due to chromatogenic material incorporated into dentin and enamel affect the light-transmitting properties of teeth, resulting in a gradual darkening. Since tooth discoloration varies in etiology, appearance, localization, severity, and adherence to tooth structure, measuring whitening changes between baseline and post-treatment L* values as a function of each individual treatment area, ensures that variability in discoloration and porosity between samples is not a factor.

Carbamide peroxide whitens tooth enamel by penetrating the porosities in the rod-like crystal structure of enamel to break down stain deposits in the dentin. Since tooth whitening is a dynamic process that is dependent on diffusion of the whitening material to interact with stain molecules, better whitening by definition implies enhancement of the diffusion process. The effectiveness of the wireless device in enhancing this diffusion process is, therefore, validated by the results, which showed that whitening was increased by two-fold when the peroxide oxidizing agent was applied by ACEK in comparison to diffusion.

The functionality of the device is validated further by using the IDE patch to elicit ACEK behavior of other drugs. By imaging pDEP behavior of acetaminophen, tetracycline, benzocaine and lidocaine particles in AC electric fields induced with an IDE assembly that is powered by inductive coupling, the study confirms that DEP can be exploited wirelessly to manipulate an assortment of drug particles at appropriate frequencies ranging from 100 Hz to 10 kHz. Additionally, the study suggests that ACEO may also be exploited wirelessly. At appropriate frequencies, drug particles could be sorted by pDEP forces and dragged to the enamel surface by additional AC electromotive forces to concentrate the particles at the enamel pores. With increased opportunity for drug particles to interact with the microporous enamel surface, this may potentially promote the uptake of an assortment of drugs in a variety of other applications.

Figure 6A:
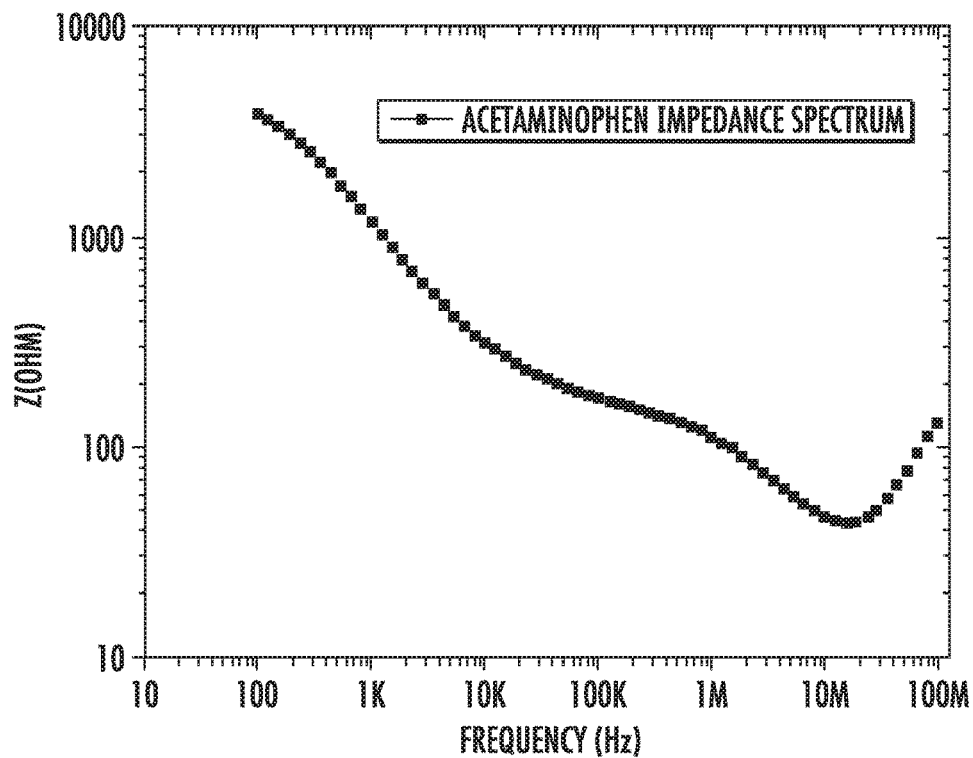
FIGS. 6A-6D show measured frequency responses of the conductivity of tetracycline and acetaminophen.
Figure 6B:
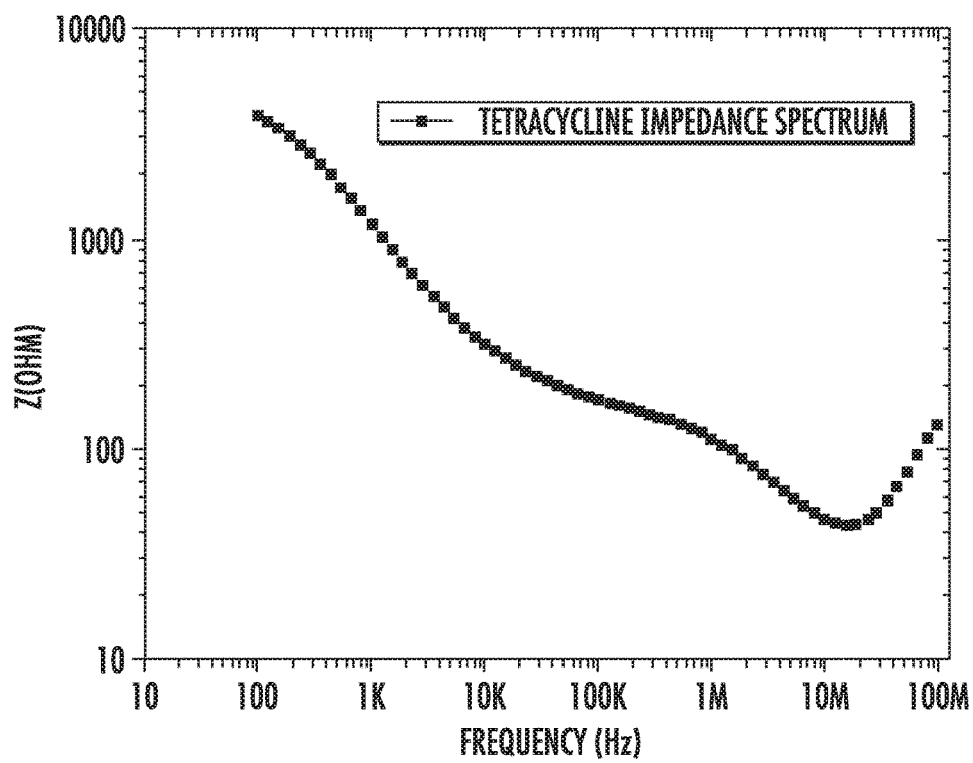
Figure 6C:
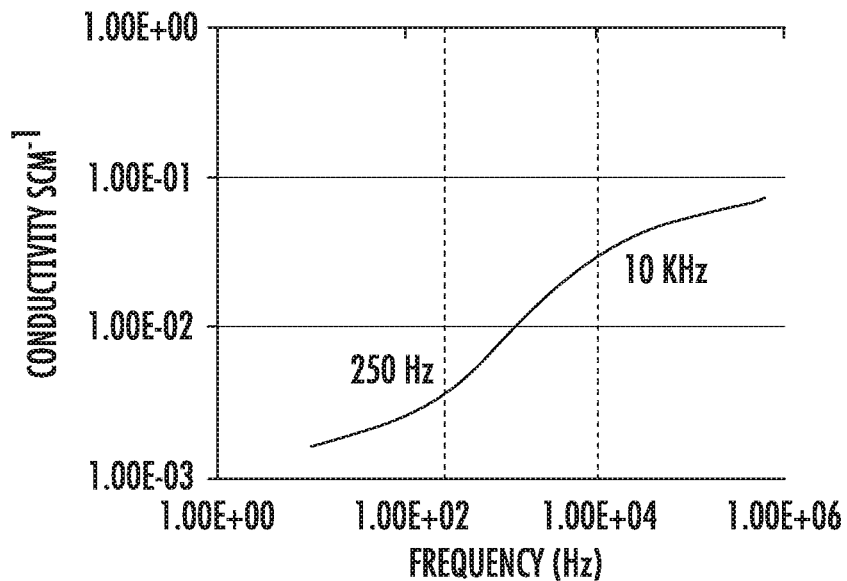
Figure 6D:
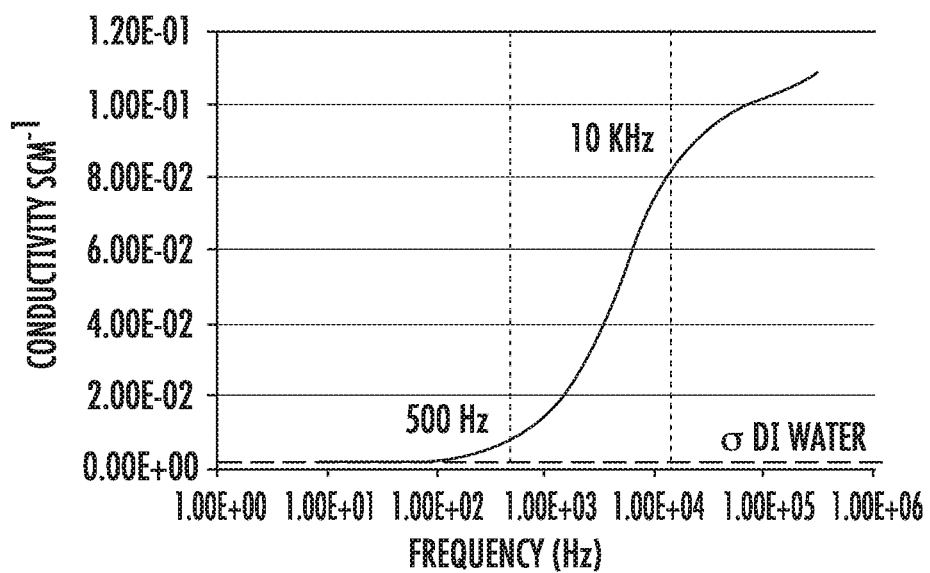

To illustrate further how appropriate frequencies for DEP behavior can be determined for a drug by its impedance spectrum, the frequency response of the conductivity of tetracycline and acetaminophen particles (FIGS. 6A-6D) was measured by dielectric analysis. As indicated by the graphs in FIGS. 6A-6D, the particle conductivity ($\sigma_p$) for both tetracycline and acetaminophen rises steadily from 100 Hz onwards and begins to plateau beyond 10 kHz. Taking a media conductivity ($\sigma_m$) for the aqueous media at about $10^{-4}$ S/cm, nDEP behavior ($\sigma_p < \sigma_m$) is not expected at any frequency for either drug, as per the conductivity analysis which predicted that ($\sigma_p > \sigma_m$) at all frequencies. Conversely, strong pDEP behavior ($\sigma_p > \sigma_m$) is expected at frequencies at about 10 kHz. In fact, results from imaging the tetracycline and acetaminophen particles at 10 kHz showed strong pDEP at that frequency (FIGS. 6B, 6D). The baseline for particles prior to the field is shown in FIGS. 6A, 6C. Upon applying fields of 5 $V_{pp}$/mm at 1000 Hz, the particles are collected at the electrode edges, as per FIGS. 6B, 6D thereby confirming pDEP behavior as predicted.

On the other hand, DEP forces are highly localized and there is a need for longer-range translation forces that can drive the particles away from the IDE array towards the intended biologic target. Since ACEO generates vortices within the fluid that act to drag pDEP trapped particles away from the electrode edges, it is likely to generate more long range particle translation. As shown in FIGS. 7A-7D, fields of 15 Vpp/mm at 1 kHz and 10 Vpp/mm at 500 Hz, respectively, cause the translation of benzocaine and lidocaine particles vertically away from the edges of the electrode in this fashion.

The translation of latex particles above the plane of the electrode under a field of 10 Vpp/mm at 8 kHz was attributed to ACEO. Although it is known that ACEO is stronger as the frequency is further decreased, no effect of ACEO was observed at frequencies below 8 kHz. This is likely due to a critical frequency at which ACEO dominates. Hence, while velocity due to ACEO increases as the frequency is lowered from the point of discernible pDEP, this velocity reaches a maximum and then reduces with a further decrease in frequency. In the experiments, the maximum ACEO vortices for benzocaine and lidocaine were apparent at 1 kHz and 500 Hz, respectively. Based on applying these fields in a similar manner to all the tested drugs, it is inferred that this mechanism can be exploited to motivate other drugs of varying molecular weight and structure.

Unlike iontophoresis and electroporation (DC) electrochemical drug delivery technologies (used in a variety of settings from physical therapy to post-operative pain management), ACEK can motivate any chemical compound, including those that are difficult to polarize because of the absence of free charges, random distribution of charge or large molecular size. Moreover, these drug delivery techniques use high current intensity or long treatment times that can lead to pain and significant soft tissue damage. In extreme cases, high currents produced by the use of DC in iontophoresis can short through a patient's heart. The use of low-voltage AC signals (0.05-0.48 mA) in this ACEK-based device is a major difference which could significantly reduce these safety risks. A dental patch that can receive the required voltage signal wirelessly and activate ACEK effects from outside the mouth is an alternative solution to conventional devices.

The translation of this technology to clinical applications is significant to the dental community. By using ACEK to drive whitening agents into tooth enamel, unpleasant side-effects associated with conventional chairside bleaching treatments can be eliminated, including sore throat and gingival inflammation. Targeted peroxide delivery could eliminate unwanted swallowing of bleaching agents, while providing enhanced absorption and, in turn, better whitening. In addition to superior whitening, the benefits can include significantly reduced treatment time and controlled penetration to decrease the risks of reduction in enamel and dentin sublayer microhardness and to bond strength of resin-based materials bonded to dentin, resulting from home and in-office bleaching systems after multiple daily applications with significantly longer treatment times.

The study showed that an IDE assembly powered by inductive coupling could trap, manipulate, and translate carboxylate-modified microspheres, tetracycline, acetaminophen, benzocaine and lidocaine particles using single frequencies to induce ACEK effects wirelessly. The study also showed that the wireless patch could be effectively applied to a dental whitening application known to be enhanced by an analogous electrochemical delivery system powered by a function generator. After applying 35% carbamide peroxide to human teeth (n=15) under ACEK effects with an IDE powered by inductive coupling for 20 minutes, SCI and SCE whitening was increased by 215% and 194% respectively, compared to topical application. By manipulating drug particles with ACEK effects, the study suggests that an IDE assembly powered by inductive coupling may potentially enhance delivery of drugs of varying molecular weight and structure in other dental applications. ACEK may potentially advance drug delivery in dentistry by: extending transport of antibiotics, analgesics and anesthetics, to specific intraoral targets; bypassing first-pass metabolism and improving the efficacy and safety of drug delivery.

Introduction—Lab on a Chip

During the past decades, lab-on-a-chip (LOC) technology, which mostly deals with precise manipulation of micro/nano-scale liquid and/or biological particles, has made considerable progress in the development of micro/nano-systems for chemical, biological, and medical applications. Among various LOC devices, many are based on electrical methods, including electrophoresis (EP), electrowetting on dielectric (EWOD), and electrokinetics effects (including dielectrophoresis (DEP), AC electroosmosis (ACEO), and electrothermal effect). These electrical LOCs have found numerous applications in processes such as drug delivery, cell analysis, analytical assay, and clinical diagnostics.

In spite of their excellent functionality, their usability needs to be simplified in order to increase the acceptance of the technology for clinical and point-of-care applications. One of those hurdles to be addressed is that they usually require many wired connections to electronic instruments such as power supplies, amplifiers, function generators, etc. Moreover, in some applications where the LOC devices are needed to be implanted inside the body or for the devices working at hard-to-reach areas, it is highly desirable that the power for device operation and data communication with the outside world be done by wireless data and power transmission.

Inductive coupling has been extensively used for wireless powering of biomedical devices and their data communication with the external world. Usually, high frequency signal transmission is adopted, which is then used directly or converted to DC power on a chip. The required power of the device is inductively coupled to a RF identification reader (RF ID) and converted into a 10 V direct-current (DC) voltage. However, electrical LOCs often have specific requirements for signal waveform and AC frequency, and on-chip regeneration of low frequency signals is challenging.

The presently disclosed subject matter provides in some embodiments a compact, flexible, low voltage, and disposable wireless lab-on-a-film (LOF) device for particle assembly, fluid mixing and pumping. The LOF device, which in some embodiments is fabricated on both sides of a flexible plastic layer with overall dimension of 10×20 mm$^2$, comprises a receiving coil (for wirelessly receiving AM signal through inductive coupling), surface mount capacitor and diode (for demodulation of AM signal and recovering low frequency AC signal) and an interdigitated electrode (IDE) array (for excitation of ACEO effect inside of the solution over IDE). The device uses inductive coupling and AM scheme to receive the required low frequency AC signal for excitation of the ACEO effect at the IDE to achieve the abovementioned functions. The IDE works with very low voltage ranges (less than 5 V) that can be wirelessly controlled.

After characterizing the electrical components (receiving coil, IDE, and resonance response of the LOF circuit model), the capability of the LOF system is studied in recovering low frequency AC signals for a range of frequencies and waveforms from the AM signal. Moreover, the frequency and waveform of modulating signals are studied for efficient operation of the device. In order to validate the functionality of the LOF, FluoSpheres™ particles diluted in DI water are loaded into a chamber over the IDE. By transmitting an appropriate AM signal to the LOF and controlling the voltage level over the IDE, different microfluidic effects of particle assembling, fluid mixing and fluid pumping are observed.

Example Design and Operation

Figure 10A:
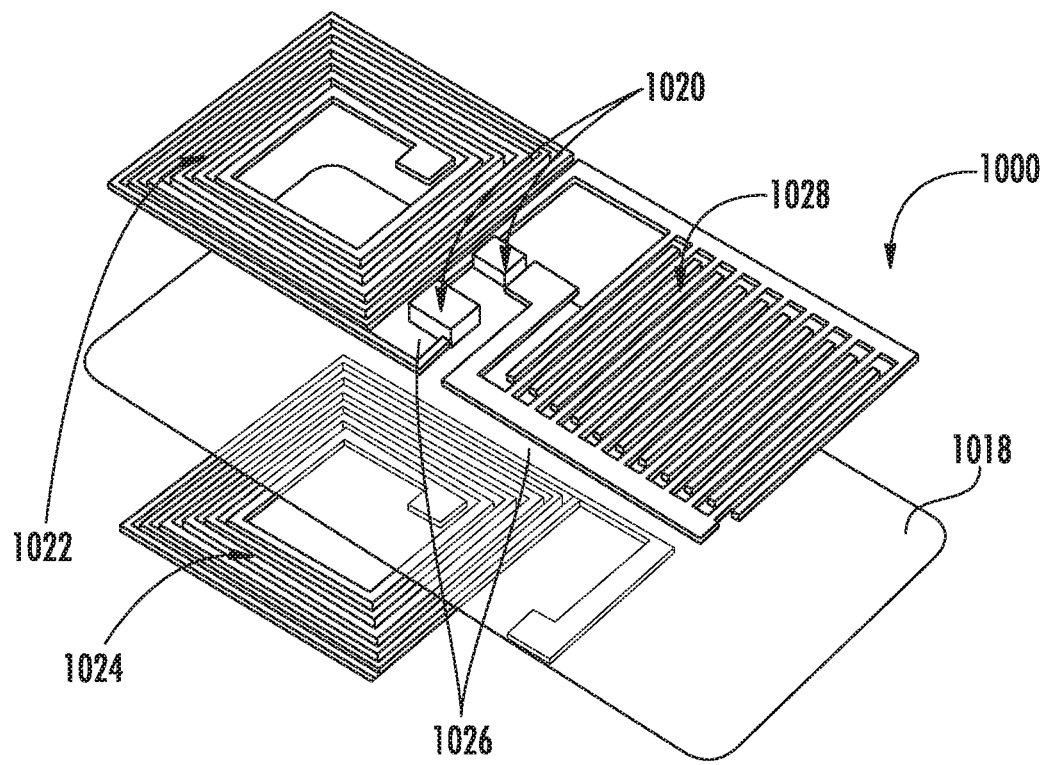
FIGS. 10A-10G illustrate an example lab-on-film (LOF) device 1000.
Figure 10B:
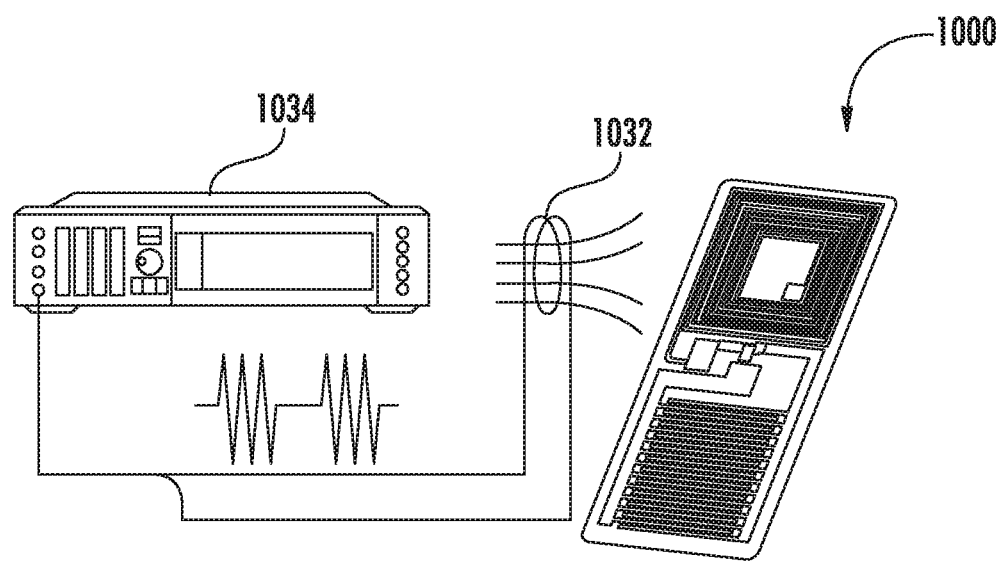
Figure 10C:
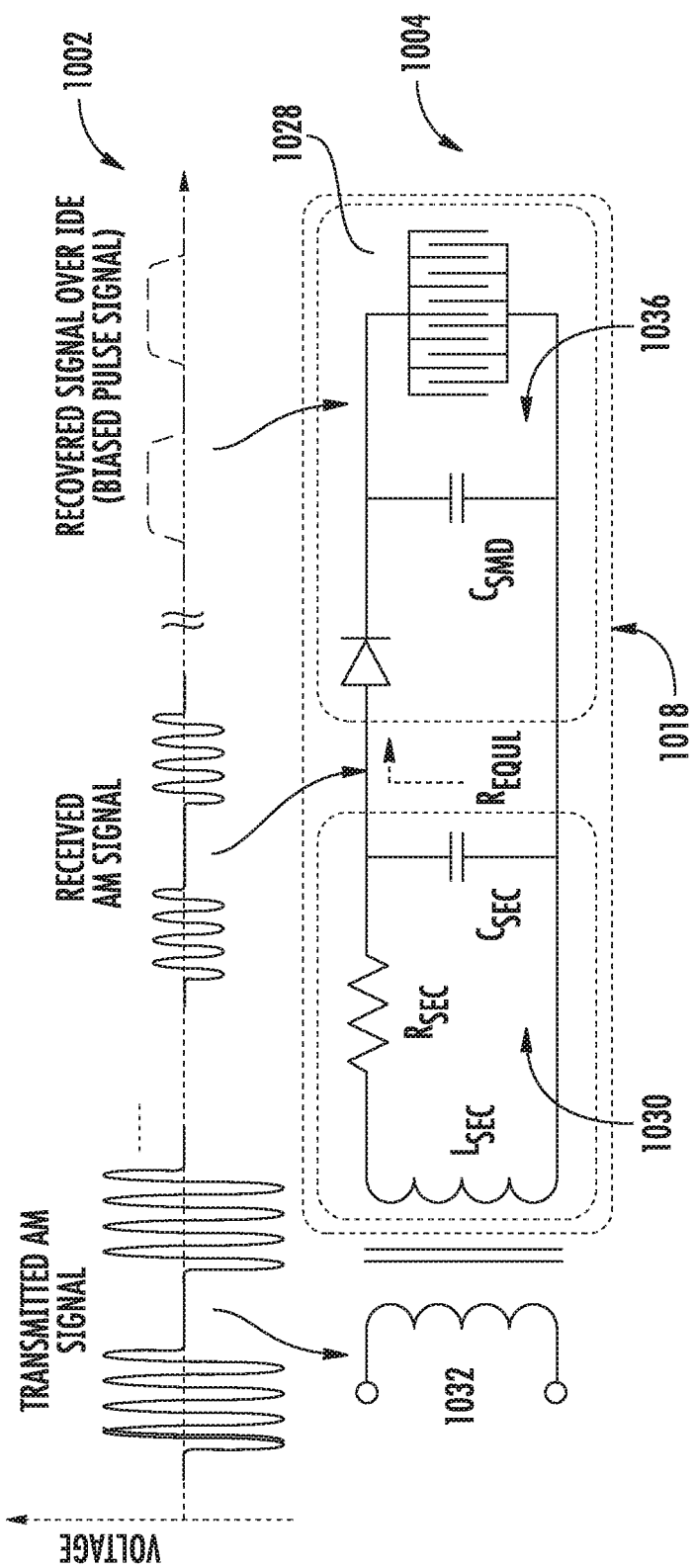

FIGS. 10A-10G illustrate an example lab-on-film (LOF) device 1000. FIG. 10C shows a signal graph 1002 and an equivalent circuit diagram 1004. A schematic view of the wireless ACEO LOF is shown in FIG. 10A. The LOF device has a compact structure and is built on a double-sided flexible printed-circuit-board (PCB) substrate 1018. As can be seen, in some embodiments the wireless ACEO LOF pad comprises three layers; 1) metal traces and surface mount devices 1020 for creation of the front-side coil 1022, IDE and demodulation circuitry (front-side), 2) metal traces for the creation of the back-side coil (back-side) 1024, and 3) a flexible support layer 1018 which is sandwiched between the front and back side metallization.

The front and back side coils 1022, 1024 are connected in series through a via hole 1026 in the center of the coils 1022, 1024, and together form the receiving coil 1030. The outer end of the front coil 1022 is connected to the anode of the SMD schottky diode (see circuit diagram 1004). The cathode of the diode is connected to the SMD capacitor and one end of IDE 1028. The outer end of back coil 1024 is connected to the other end of IDE 1028 and the SMD capacitor on the front side through another via hole 1026 in the flexible layer 1018. The SMD devices 1020 can be located either on the front or on the back side. Here they are put on the front side for the convenience of observing microfluidic effects on the IDE 1028.

Figure 10D:
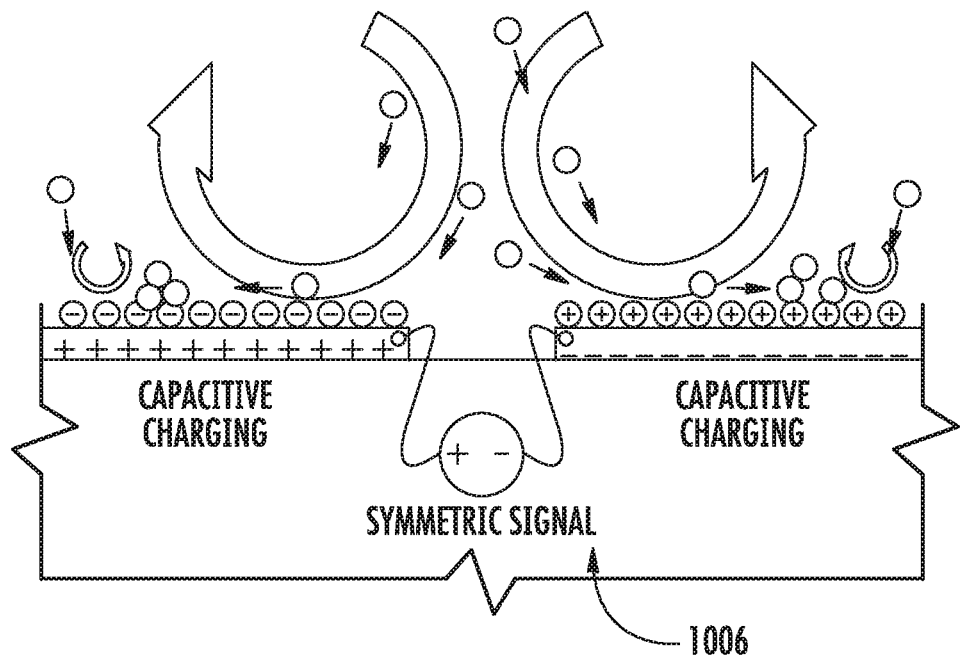
Figure 10E:
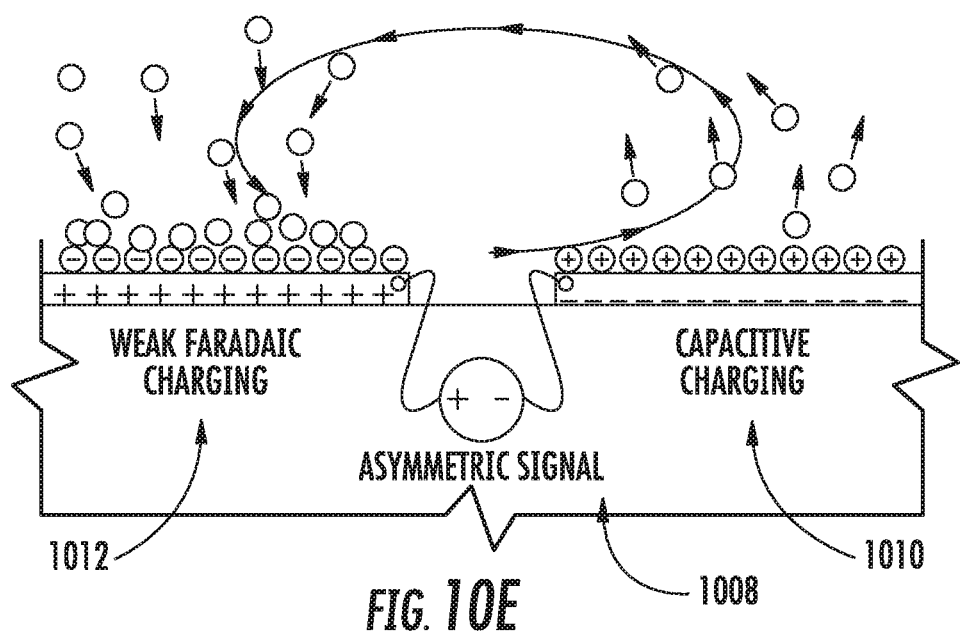
Figure 10F:
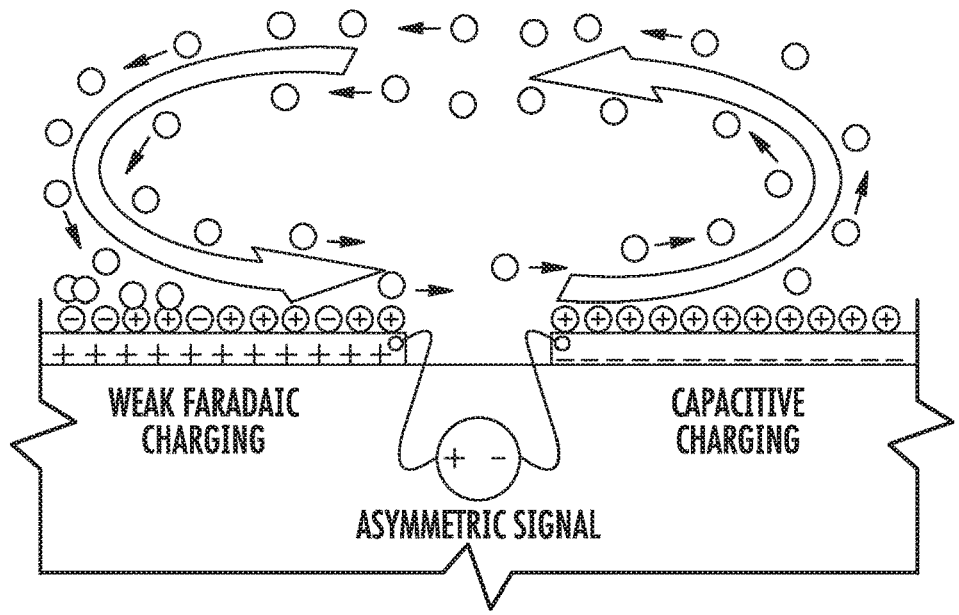
Figure 10G:
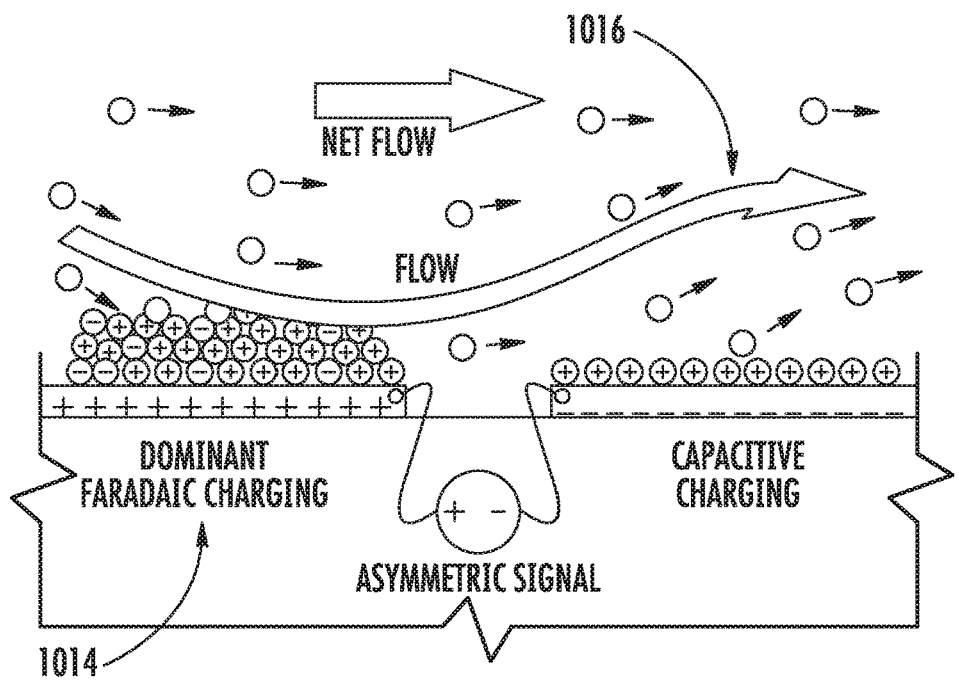

A low frequency AC signal, which is used to provide excitation of ACEO effects, is wirelessly transmitted to the disposable LOF pad 1018 through the amplitude modulation (AM) scheme. As shown in FIG. 10B, an appropriate AM signal is generated by a signal generator 1034 and is applied to a transmitter coil 1032, which acts like an antenna to wirelessly transmit AM signal onto the ACEO LOF pad. The receiving coil 1030 intercepts the AM signal and delivers it to an envelope detector circuit 1036 that is located immediately after the receiving coil 1030 (FIG. 10C). In some embodiments, the envelope detector comprises a SMD diode, a SMD capacitor and the IDE 1028. The envelope detector demodulates the received AM signal by removing high frequency carrier and recovers the low frequency modulating AC signal. Therefore, the low frequency AC signal is passed onto the IDE 1028, which as a biased pulse signal is used to induce biased the ACEO effect (FIG. 10E-10G). Although the presentation here uses one envelope circuit to receive one signal, it can be configured such that more than one envelope circuit can be embedded in the electrode PCB substrate to allow reception and manipulation of more than one signal to cause more than one AC electrokinetic phenomenon at various times.

An AM signal is defined by its carrier and modulating signals. Here, the resonance of the coil inductance and IDE capacitance is utilized to increase the transmitted voltage level on the LOF pad 1018 and consequently the strength of electric field induced by the IDE 1028. Therefore, the carrier frequency is carefully chosen to take advantage of the circuit resonance. The modulating signal will be the signal applied over the IDE 1028 to induce ACEO flow, and ACEO effect is known to be frequency-dependent. Hence, in order to achieve optimum operation for the LOF 1000, both carrier and modulating signal frequencies are optimized.

Alternating current electroosmosis (ACEO) refers to fluid motions induced by movement of surface charges at the solid-liquid interface (electrical double layer) when an AC signal is exerted on a pair of neighboring electrodes. When a low voltage symmetric AC signal is applied to the electrode, the charges/ions in the double layer are induced by a capacitive charging mechanism. The electric fields created by two symmetric electrodes exhibit mirror symmetry. Moreover, the charges in the double layer and electric fields change signs simultaneously, which is why ACEO produces two steady, counter-rotating vortices above each electrode. A schematic view of induced microflows at the electrode surface by a symmetric AC signal 1006 is shown in FIG. 10D. These vortices are stable as long as the amplitude of the symmetric AC signal is not too high.

When electrodes are activated by a biased AC signal (asymmetric AC signal 1008), co-ions instead of counter ions will be appear on electrodes with positive potential due to electrochemical reaction. This process of electrode charging is known as Faradaic charging. There are some important differences between Faradaic and capacitive charging which are the basis for the generation of different microfluidic flows. 1) Faradaic charging can produce charge densities orders of magnitude higher than capacitive charging. That is why the microfluidic flows generated by Faradaic charging are much stronger than capacitive charging. 2) The microfluidic flow velocity as the result of Faradaic and capacitive charging can be estimated by $S\sigma \sim \exp(V)$ and $\sigma \sim V^2$, respectively. Based on these equations, as the voltage increases, the flow velocity as a result of Faradaic charging is much higher than that by capacitive charging.

If a biased signal is used for the excitation of an ACEO effect (known as biased ACEO), the positive electrode (the electrode which is connected to the positive polarity of the signal source) experiences both capacitive and Faradaic charging while the negative electrode (the electrode which is connected to the negative polarity of the signal source) always experiences capacitive charging. There is a threshold voltage for positive electrode to undergo Faradaic charging. In biased ACEO, when the voltage level is lower than the threshold voltage, both positive and negative electrodes are subject to a capacitive charging mechanism. Hence, the microflows as shown in FIG. 10D are induced.

When the voltage level is slightly higher than the threshold voltage, the positive electrode will experience both capacitive 1010 and a weak Faradaic charging 1012. As a result, the symmetry of induced charges over the electrodes is broken which leads to creation of larger vortices covering both positive and negative electrodes as shown in FIG. 10E. However, because the voltage level is low, the microflows are not observable and the only visual effect is that the particles suspended in the solution slowly move away from the negative electrode toward the positive electrode. By increasing the voltage level, Faradaic charging becomes more intense leading to stronger and larger vortices into the solution shown in FIG. 10F. As the voltage increases further, the Faradaic charging becomes dominant 1014, and the vortices between pairs become connected and unidirectional fluid flow 1016 begins to appear as in FIG. 10G.

An advantage of biased ACEO flow over traditional ACEO is the tunability of the microflow's direction and velocity by controlling the biased signal's amplitude. Thus far, the biased ACEO technique has been successfully used for development of LOCs for efficient fluid mixing, pumping, and particle trapping/manipulating. Moreover, flow velocity by biased ACEO is potentially higher than ACEO pumps. Hence, biased ACEO technique is a promising technique for implementation of microfluidic devices for multifunctional operations.

For the example LOF devices described in accordance with the presently disclosed subject matter, the recovered low frequency signal over the IDE is a single sided pulse signal, as shown in FIG. 10C. This signal can be considered as a DC-biased pulse signal. Hence, the LOF will be able to generate various biased ACEO microfluidic effects based on the recovered single-sided signal's level.

Example Methods and Materials

FIGS. 11A-11F show the layout used for LOF device fabrication, example photographs, a demonstration of the device's flexibility, a zoomed-in view of metal traces, example design dimensions, and a schematic cross-sectional view of the device.

Figure 11A:
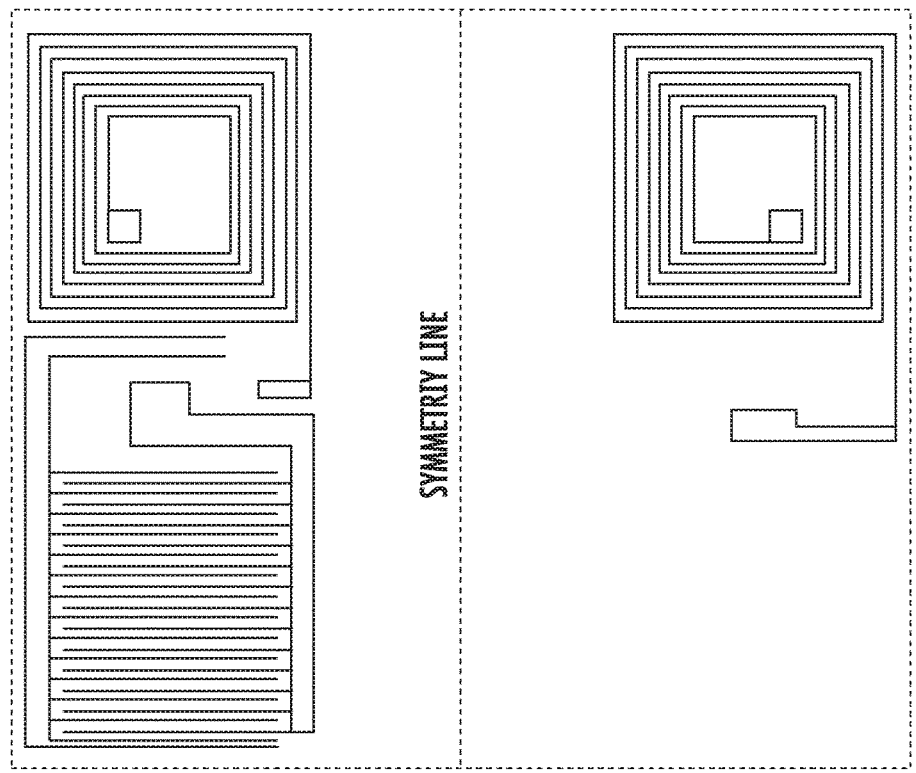
FIGS. 11A-11F show the layout used for LOF device fabrication, example photographs, a demonstration of the device's flexibility, a zoomed-in view of metal traces, example design dimensions, and a schematic cross-sectional view of the device.

Pyralux 8525R (DuPont, USA), a double-sided flexible copper cladded polyimide film, is used for the device prototyping and patterned by a printed circuit board (PCB) technique. The fabrication process is simple, rapid, low cost and can be performed by benchtop equipment without the need for cleanroom facilities. Representative fabrication steps are as follows: 1) The layout of the device is drawn in Microsoft Visio software on a computer and then printed by a regular laser printer onto a Toner Transfer Paper (Pulsar-ProFX, Colorado Springs, Colo., United States of America). The layout of the device is shown in FIG. 11A. The symmetry line is used to precisely align the front and back side coils when transferring the pattern onto the copper film. 2) In order to transfer the pattern of the printed pattern onto the double-sided copper film, the printed toner transfer paper is folded along the symmetry line over a piece of double-sided copper film (Pyralux 8525R). The folded paper along with the copper film is then rolled through a laminator (Apache model AL13P, Humacao, Puerto Rico) at a temperature of 370° F. for approximately 30 seconds.

Figure 11B:
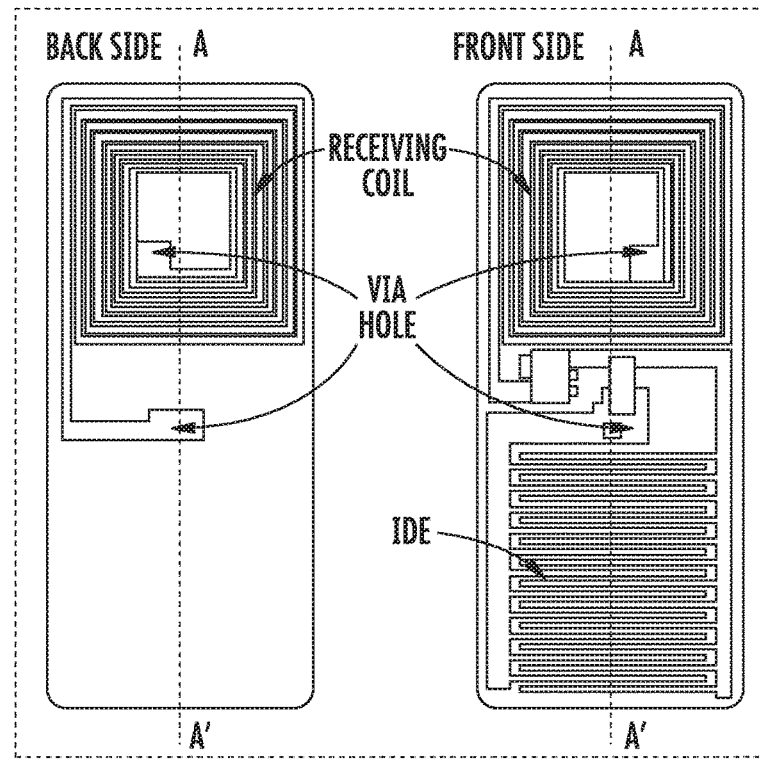
Figure 11C:
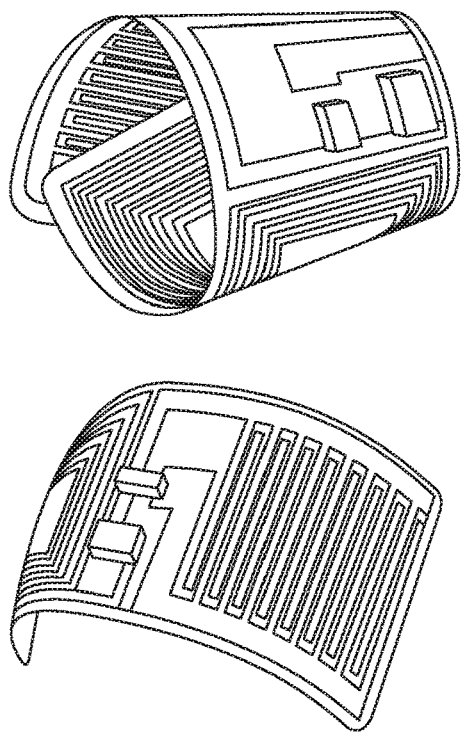
Figure 11D:
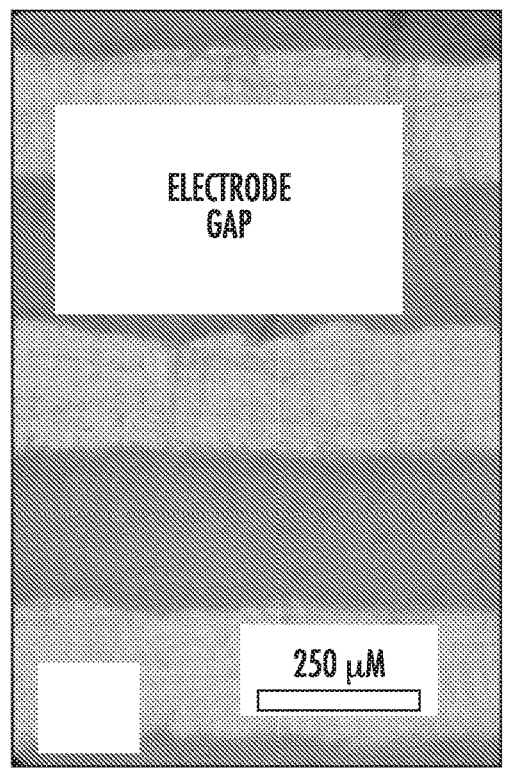
Figure 11E:
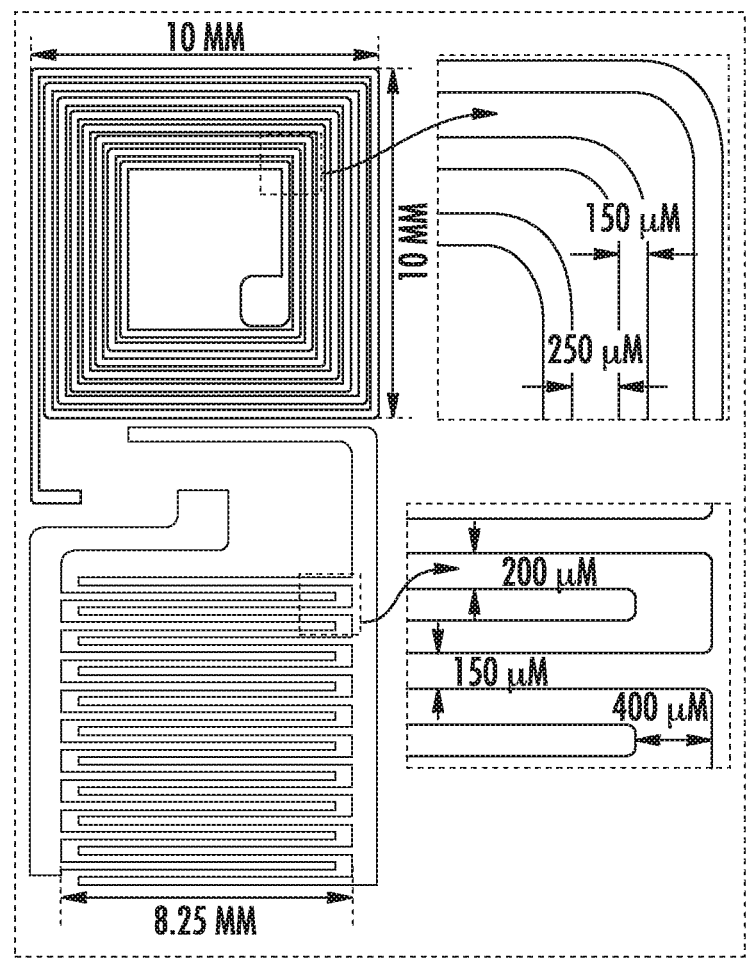
Figure 11F:
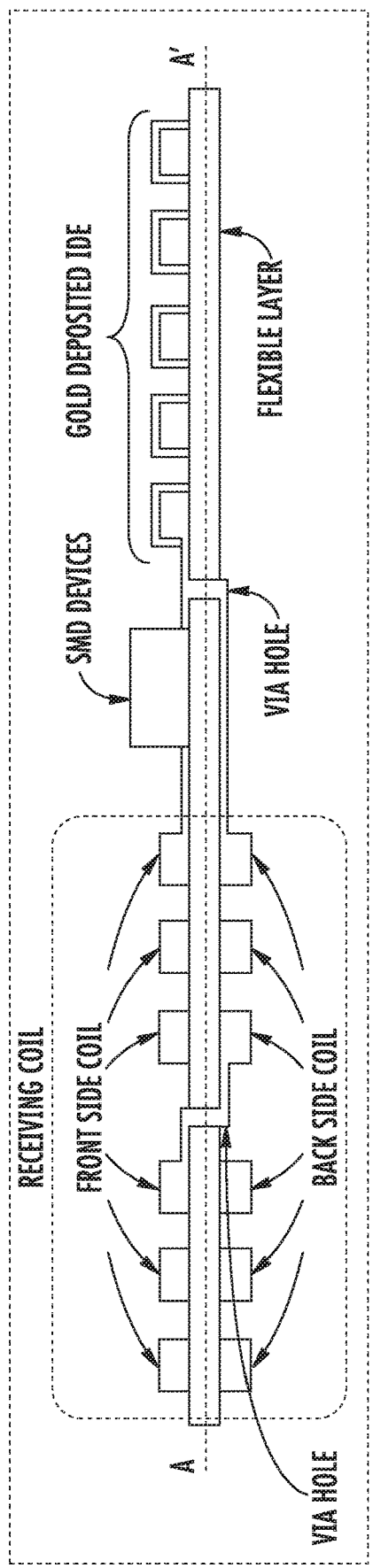

3) A very thin layer of copper etch-resist film (Green TRF Foil, PulsarProFX) is then folded over the copper film and laminated for 30 seconds. 4) After the second lamination, the etch-resist film is then peeled off from the copper film. Only the previously patterned areas are covered by a very thin layer of etch-resist film. 5) The copper film is then chemically etched in a ferric chloride solution (MG Chemicals, Surrey, British Columbia, Canada) for approximately 25 minutes to yield the desired pattern, then rinsed thoroughly under running de-ionized (DI) water for 5 minutes. 6) Subsequently, gold electroplating is conducted in order to coat the IDE surface with a very thin layer of gold. 6) Through holes are drilled and electroplated to make connections between the back and front side coils and between the back coil and IDE across the polyimide support layer. 7) The device is sequentially cleaned in acetone, isopropanol alcohol (IPA) and de-ionized (DI) water with ultrasound for 5 minutes each, respectively. The electrode is cleaned in RIE plasma cleaner to remove any organic residues. 8) External electronic components (e.g. SMD diode and capacitor) are soldered on. The front and back side of the fabricated device is shown in FIG. 11B and its schematic cross-sectional view from AA' cut is shown in FIG. 11C. As apparent from FIG. 11C, the back and front side coils are connected in series in the middle through a via hole to construct the receiving coil. These two coils are precisely aligned with each other across the flexible layer to maximize their mutual inductance to increase the inductance of the receiving coil. The design dimensions of the device are shown in FIG. 11D. FIG. 11E demonstrates the flexibility of the final LOF device and FIG. 11F shows a closed-up view of the metal traces. The metal traces in FIG. 11F have rough edges due to the limited precision of the PCB fabrication process. This roughness has no negative effect on excitation of the biased-ACEO effect in some examples.

Figure 12:
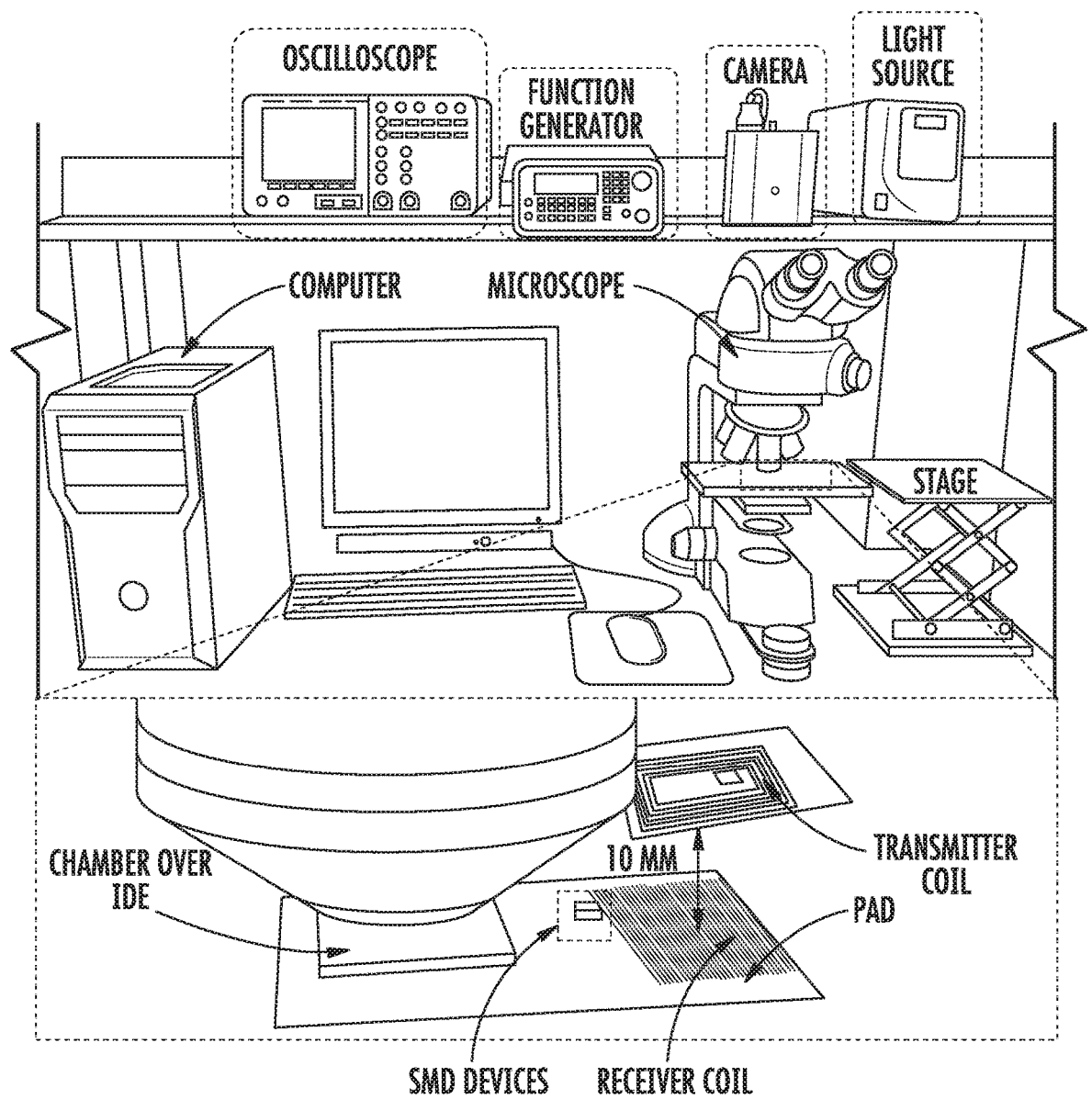
FIG. 12 shows an example experimental setup for testing the LOF operation.

FIG. 12 shows an example experimental setup for testing the LOF operation. The experimental setup comprises a wireless biased ACEO LOF under test, an optical microscope for characterization of biased ACEO microflows, a transmitter coil and its holder, AC signal generators, digital oscilloscope, a precision impedance analyzer, and some probe connectors, for signal transmission experiments.

For low frequency signal transmission experiments, an AM signal was generated by two Agilent arbitrary waveform generators (model 33220A) and applied to the transmitter coil. An Agilent mixed signal oscilloscope (model MSO6012A) was used to view and record the demodulated signals. An Agilent impedance analyzer (model 4294A) was also used to acquire coil and IDE impedance data, and subsequently, the data were recorded through its LAN port onto a computer using software Data Transfer V3.0 (SEKONIC).

In order to visualize the biased ACEO effect by the IDE, a chamber was used to hold the solution over the IDE. Carboxylate-modified microspheres with a diameter of 1 μm (flouSpheres, Molecular Probes) were suspended in DI water as a tracer, which was used as the test solution in the experiments. The movement of particles was observed by an optical microscope NIKON ECLIPSE LV100 and the images from the microscope were acquired by a digital camera (Roper Scientific) and subsequently transferred to the computer. For fluid velocity measurement, five particles located in the gap between two electrodes near the negatively biased electrode were traced and their velocities averaged.

Results and Discussion

Figure 13A:
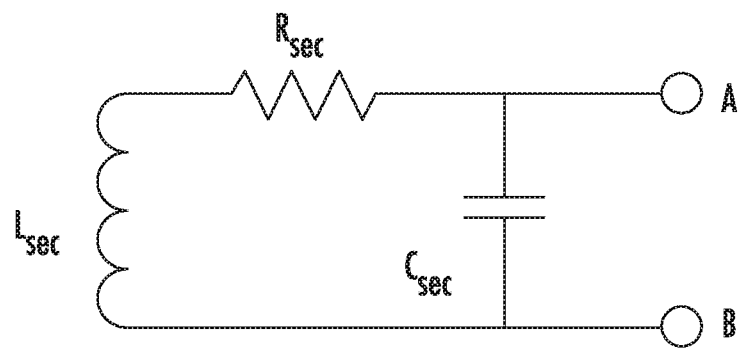
FIGS. 13A-13B show a lumped equivalent circuit model of the double-sided coil and an extend equivalent circuit model of the receiving coil by considering mutual inductance between the front and back side coils.
Figure 13B:
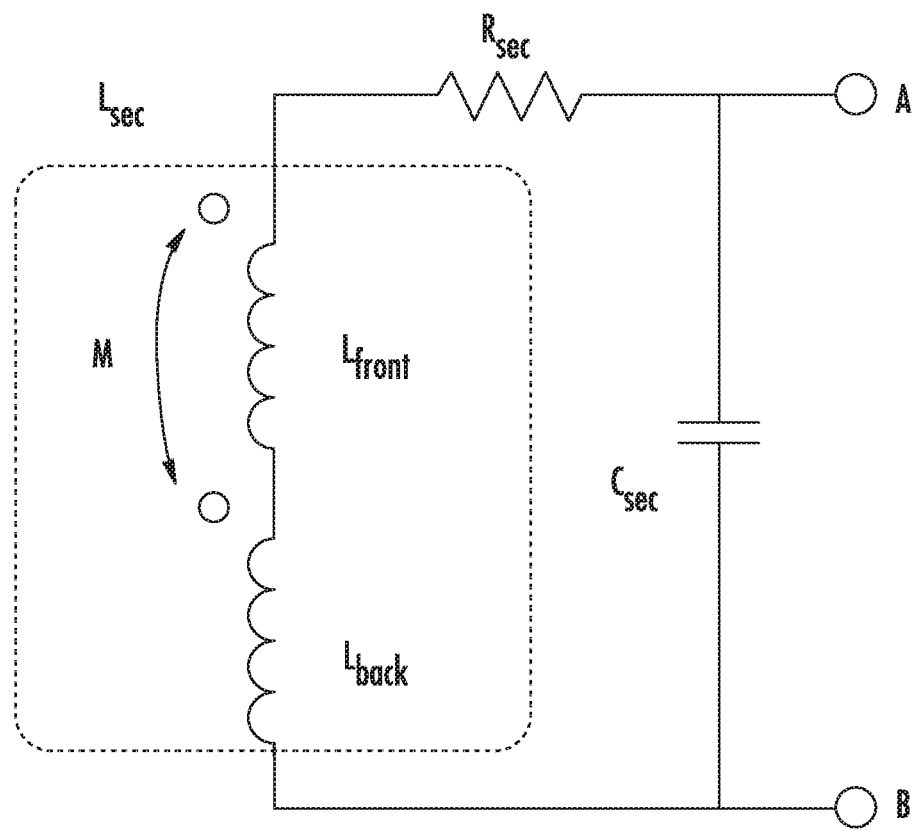

FIGS. 13A-13B show a lumped equivalent circuit model of the double-sided coil and an extend equivalent circuit model of the receiving coil by considering mutual inductance between the front and back side coils.

Miniature planar coils are known to have non-negligible parasitics, including serial resistance and shunting capacitance. A lumped equivalent circuit model for the fabricated coil is shown in FIG. 13A. In FIG. 13B, a more elaborated equivalent circuit model shows the mutual inductance between the front and back side coils and its effect on increasing total coil inductance Lsec in FIG. 13A. The coil self-inductance (Lsec) and DC resistance (Rsec) are in series, and a shunting capacitance (Csec) accounts for inter-winding capacitance coupling between the copper lines through air and the flexible layer ($\varepsilon_{air}=1$, $\varepsilon_{flex}=3.4$). The reason for designing a double-sided coil is to greatly increase the inductance of the receiving coil without increasing the LOF dimension. The benefits of increasing receiving coil inductance are two fold; 1) increasing the inductance leads to increased power efficiency of the receiving coil and 2) from the circuit point of view, by increasing the inductance, the inductive link and demodulation circuit work at lower resonant frequencies (lower than 10 MHz), which lower the complexity and cost of signal generation.

The inductance of front or back side coils can be calculated as:

$$L_{Front} = L_{Back} = 10^{-7} \times \frac{(OD+ID) \times (OD-ID)^2}{p^2} \times \left( \ln \frac{OD+ID}{OD-ID} + 0.2235 \frac{OD-ID}{OD+ID} + 0.726 \right)$$

Where $L_{Front}$ and $L_{Back}$ are the front and back-side coil inductances in Henries, respectively. p is the coil pitch in meter, OD and ID are the outer and inner diameters of the coil in meters, respectively. In this design, $L_{Front}$ and $L_{Back}$ have the same shape and dimension, and all the parameters in (1) are identical for both coils. With p=400 μm, OD=9.8 mm and ID=4.1 mm, $L_{Front}=L_{Back}$ is calculated as 0.48 pH for 8 turns. The equivalent inductance of the LOF coil ($L_{sec}$) can be calculated by the following formula, $L_{sec}=L_{Front}+L_{Back}+2M$, where M is the mutual inductance of the front and back coils and is measured to be 0.51 pH. Using above mentioned formula and parameters, $L_{sec}$ is calculated as 1.98 pH. The coil resistance is $R=\rho \times (l/A)$, where $\rho$ is copper resistivity, 17.1 n$\Omega$ m; and l and A are length and cross-sectional area of the metal line, respectively. With an average length of 52.8 cm (26.4 cm for each coil) and a cross-sectional area of 150 μm×18 μm, the resistance is calculated to be $R_{sec}$=3.34$\Omega$. The parasitic capacitance comes mostly from the outer loops. The voltage drop between the outer loops on both sides is the highest, so they contribute to the parasitic capacitance the most. The parasitic capacitance can be estimated using $C_{parasitic}=\varepsilon_0\varepsilon_r(A/d)$, Where, $\varepsilon_0\approx 8.854\times 10^{-12}$ (F·m$^{-1}$), $\varepsilon_r$=3.4, A is the overlap area of outer loop and d is the thickness of flexible layer. The parasitic capacitance is estimated to be around 8.21 pF.

The values for the elements in the coil equivalent circuit were also extracted through curve fitting of the measured impedance data with FIG. 13A. The equivalent circuit model elements (FIG. 13A) were extracted by curve fitting as $L_{sec}$=2.3 pH, $R_{sec}$=3.4$\Omega$, and $C_{sec}$=7.67 pF. The calculated values for $L_{sec}$, $R_{sec}$, and $C_{sec}$ agree with the fitted data.

Figure 14A:
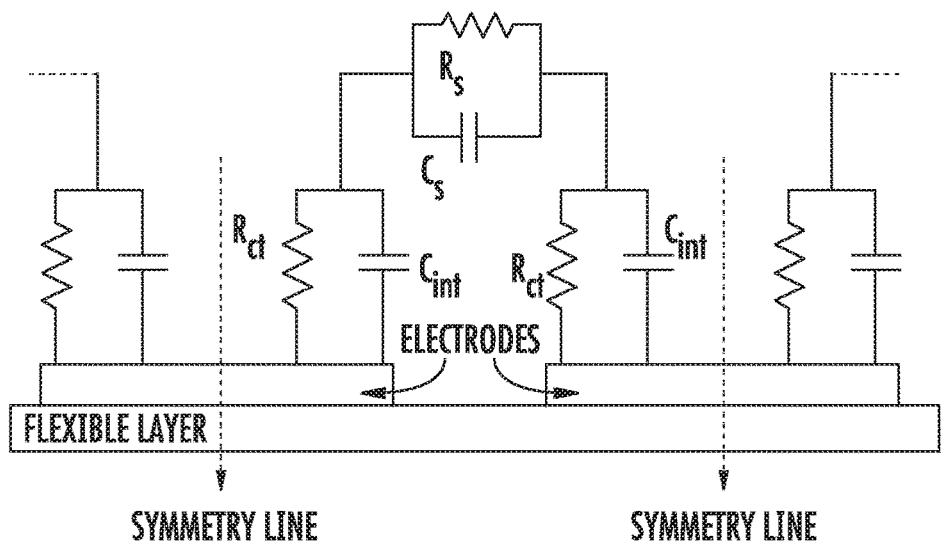
FIGS. 14A-14B show an equivalent circuit model extraction for the IDE.
Figure 14B:
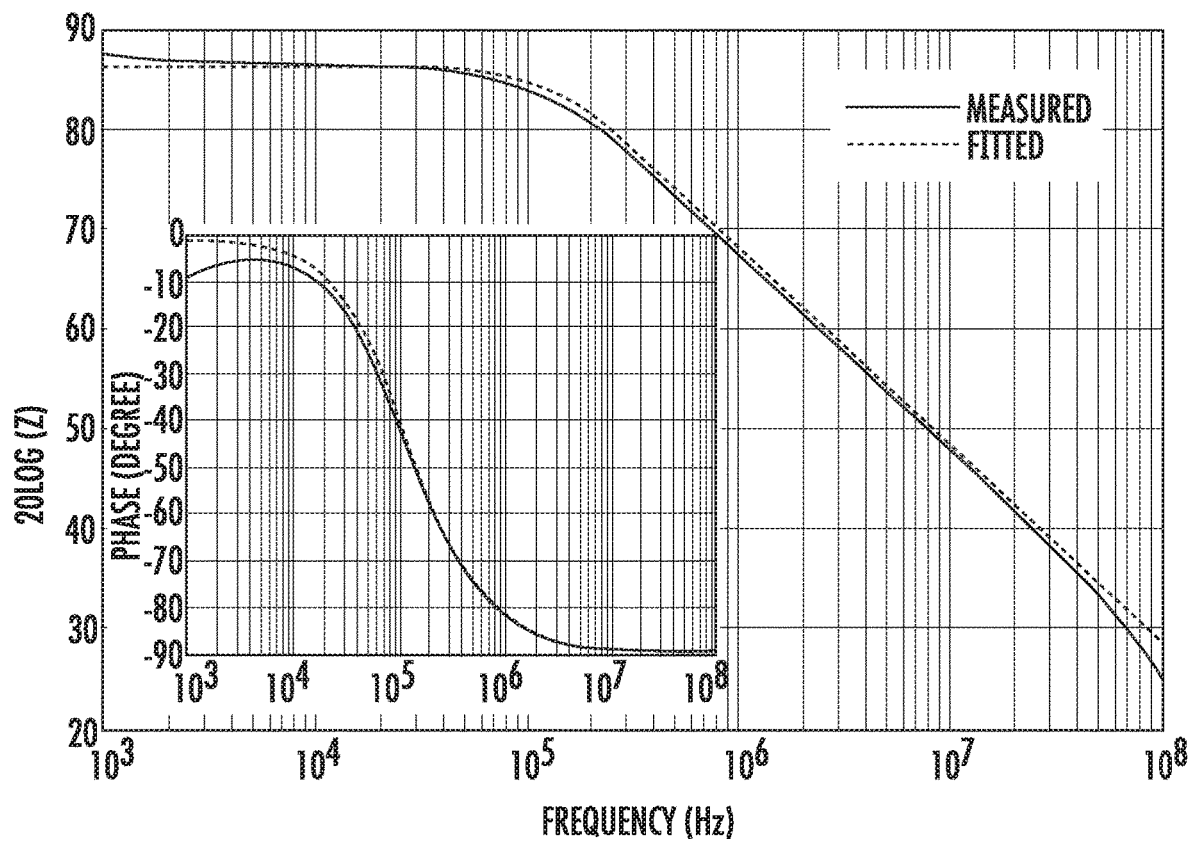

FIGS. 14A-14B show an equivalent circuit model extraction for the IDE. FIG. 14A shows an impedance network between two nearby fingers when the IDE is immersed in solution, and FIG. 14B shows a comparison of fitted and measured impedance spectra of the IDE from 10 kHz to 100 MHz. The inset is the phase angle.

Characterization of the IDE is performed with the IDE immersed in working fluid. When the IDE is immersed in a solution, the impedance between two nearby fingers can be approximated by a network of an interfacial capacitor and charge transfer resistor at the electrode/electrolyte boundary and resistance and capacitance in the solution bulk.

An equivalent circuit for two neighboring fingers of IDE is shown in FIG. 14A, in which $C_{int}$ is interfacial capacitance, $R_{ct}$ is charge transfer resistance, $R_s$ is electrolyte resistance, and $C_s$ is electrolyte capacitance. The interfacial capacitor is caused by electric double layer (EDL). When a solid material is immersed in solution, the surface of the solid material will acquire surface charges. To maintain charge neutrality, counter ions are induced within a very thin layer at the solid/liquid boundary to counter the surface charges at the solid surface, which is commonly known as the EDL. By considering the layers of counter ions as one plate and the electrode surface as the other plate, the EDL can be modeled as a capacitor, and the separation distance between two plates is the Debye length of EDL.

By the use of the impedance network in FIG. 14A and measured impedance spectra of the IDE when loaded with DI water, the curve fitting was done and the circuit parameters were extracted as follow; $C_{int}$=1.2 μF, $R_{ct}$=10 K$\Omega$, $C_s$=60 pF, and $R_s$=20.6 K$\Omega$. The measured impedance spectra and curve fitting data were plotted in FIG. 14B. The agreement between the measured and fitted data supports the model and the extracted parameters.

Figure 15:
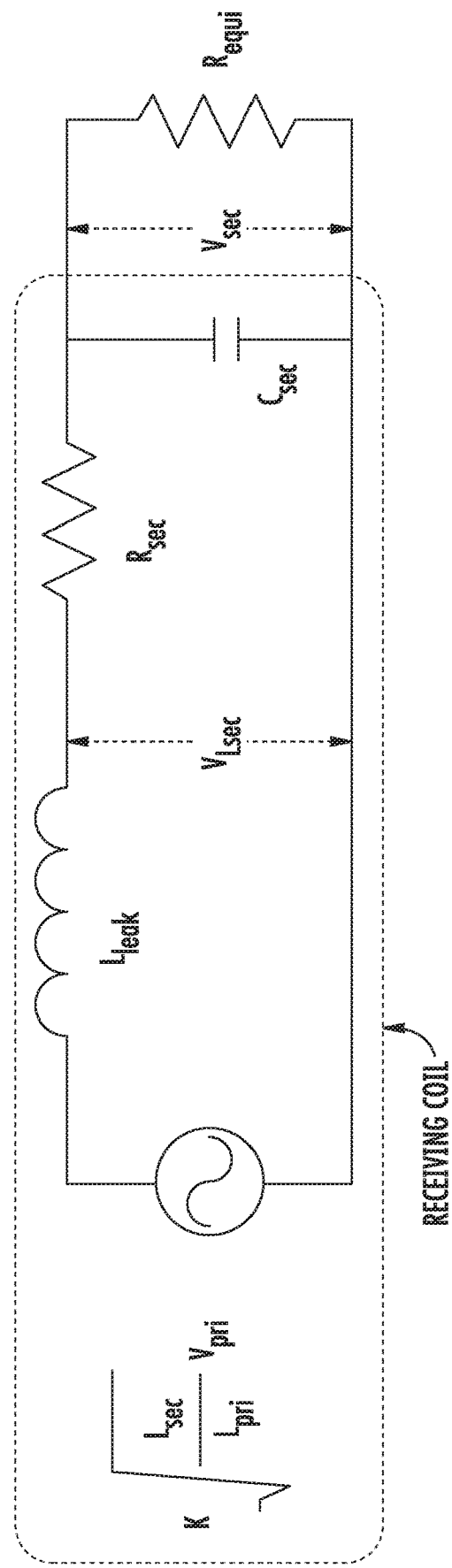
FIG. 15 illustrates an equivalent circuit for the inductive link by considering the secondary side as the reference.

FIG. 15 illustrates an equivalent circuit for the inductive link by considering the secondary side as the reference. FIG. 10C shows an equivalent circuit for wireless transmission and demodulation of an AM signal. Using the receiver side as the reference, the signal source and transmitting coil can be reflected onto the receiver side. The AM transmission circuit can be simplified as FIG. 15.

In the simplified circuit, the output from the secondary coil is treated as the voltage source with the amplitude of k $\sqrt{L_{sec}/L_{pri}}V_{pri}$ being attenuated by the leakage inductance of $L_{leak}=(1-k^2)L_{sec}$, where $V_{pri}$ is the voltage at the transmitter coil. The $R_{sec}$ and $C_{sec}$ are resistance and parasitic capacitance of secondary coil, respectively. For loosely coupled inductive links, the term $1-k^2$ in the $L_{leak}$ equation can be approximated as 1. Hence, for the circuit model shown in FIG. 15, the $L_{leak}$ is approximately $L_{sec}$. As a common practice in power electronics, the envelop detector consisting of SMD diode, SMD capacitor and IDE (FIG. 10C) is simplified to an AC equivalent resistance $R_{equi}$, which varies with current (known as rectifier regulation).

Due to leakage inductance, the receiving coil parasitic capacitance, and envelop detector, the circuit in FIG. 15 has a resonance response. The resonance frequency of the link is determined as:

$$\omega_r = \sqrt{\frac{1}{L_{leak}C_{sec}} - \frac{1}{2R_{equi}^2 C_{sec}^2} - \frac{R_{sec}^2}{2L_{leak}^2}}$$

From this equation, it can be seen that the resonance frequency is determined by the characteristics of the secondary coil and passive envelop detector circuit including the IDE circuit model. If the carrier signal frequency of AM signal is set to the resonance frequency of the link calculated in the equation, the maximum output voltage can be obtained at the secondary coil.

Figure 16:
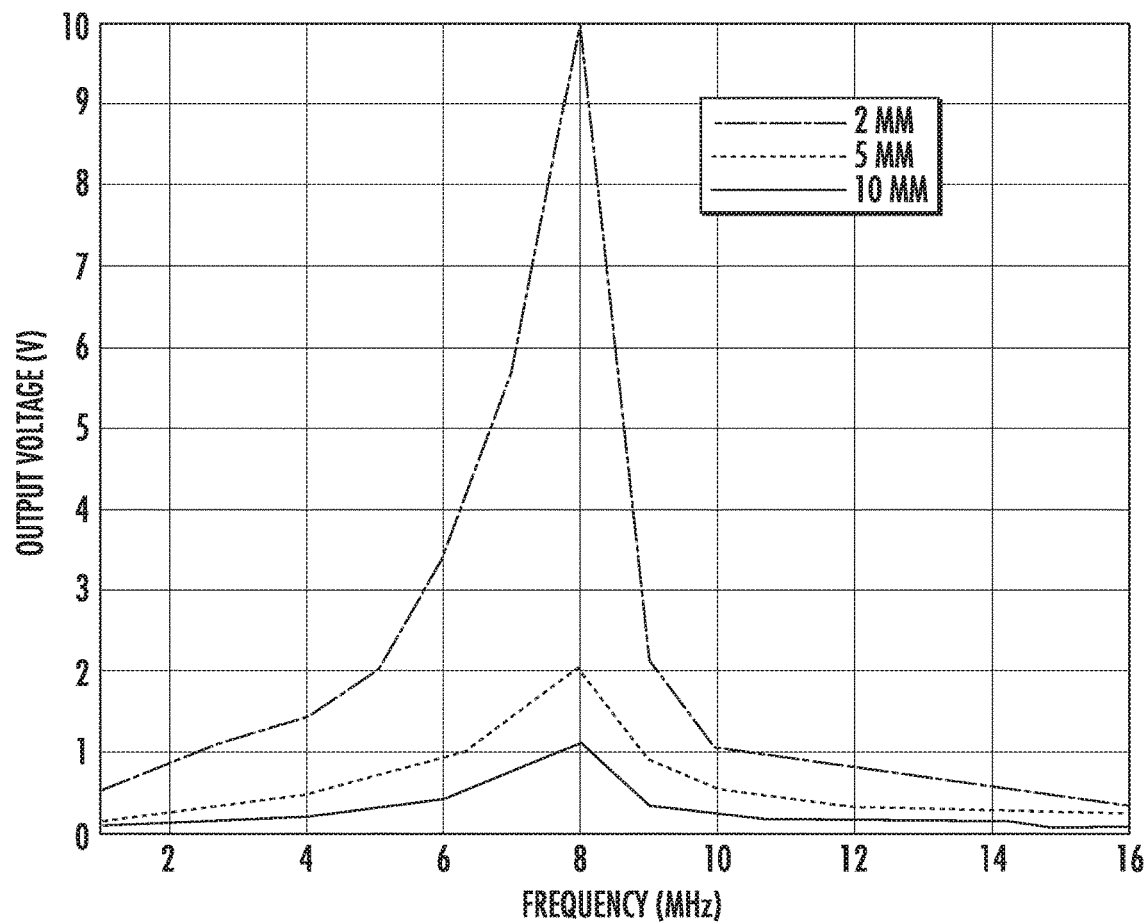
FIG. 16 shows the measured resonance response of the circuit on the LOF for different frequencies of the carrier signal.

FIG. 16 shows the measured resonance response of the circuit on the LOF for different frequencies of the carrier signal. Since resonance is utilized here to boost the output voltage, the main concern is whether a change in the relative position of the LOF will affect the resonant frequency. The resonance response of the system for a range of frequencies at different coil separations was measured and shown in FIG. 16. From FIG. 16, it appears that the change of k has little effect on the resonant frequency, with k affecting only the magnitude of the output voltage. In order to have maximum output over the IDE, the carrier signal's frequency must be tuned to 8 MHz.

As a side note, the measured k at separations of 2, 5 and 10 mm is 0.35, 0.13 and 0.05, respectively. Therefore, setting the resonant frequency at 8 MHz will work for k lower than 0.35. Maximal coupling is achieved when the transmitter and receiver coils are radially aligned. In a practical operation, some degree of misalignment is expected. The measured k for different separations between the primary and secondary coils and also k as a function of lateral deviation from the co-axial is measured for a 5 mm separation and the plot is provided in ESI. There was no effect on the resonant frequency.

AM Signal Transmission and Demodulation

This section illustrates the LOF's capability in recovering a low frequency AC signal from an AM signal, with different waveforms and frequencies for both carrier and modulating signals. This section also illustrates the effect of the modulating signal's waveform and frequency on excitation of biased-ACEO effects within the solution in terms of induced ACEO flow velocity. Then, the optimal signal waveform and frequency for the modulating signal will be determined.

Figure 17A:
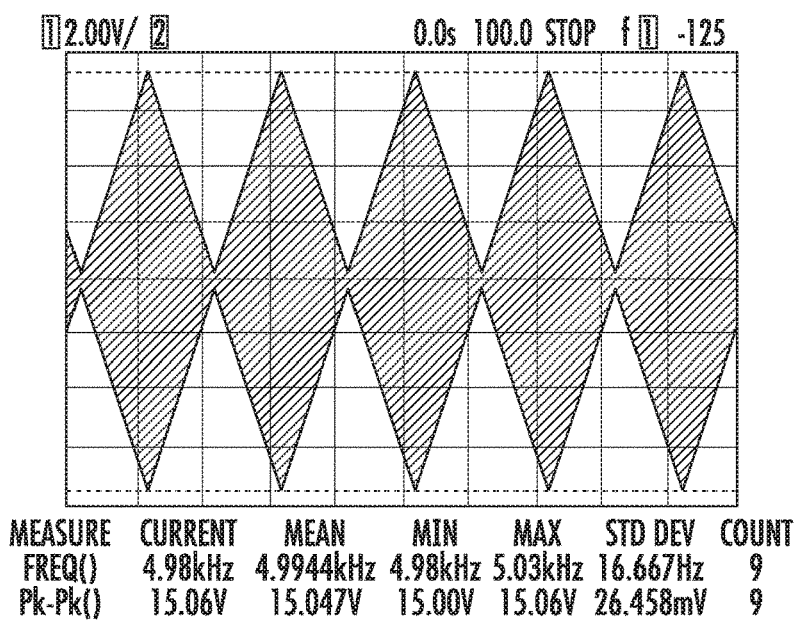
FIGS. 17A-17H illustrate various aspects of an experiment using AM signals with triangular, sinusoidal, and square wave modulating signals.
Figure 17B:
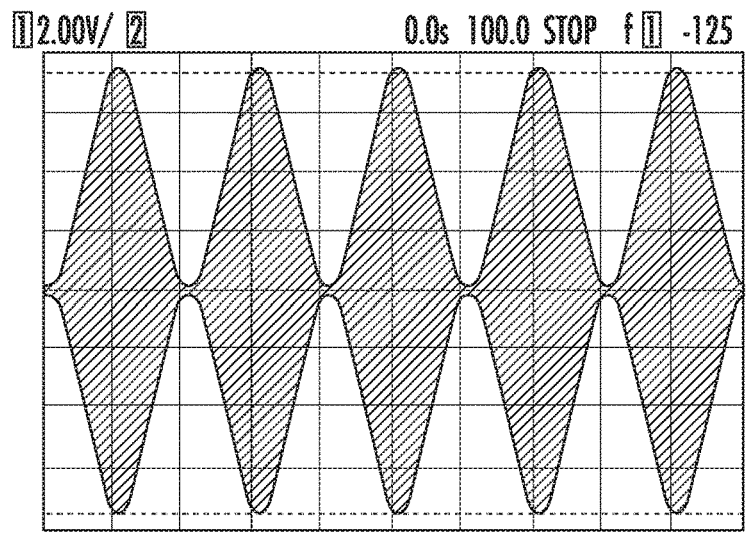
Figure 17C:
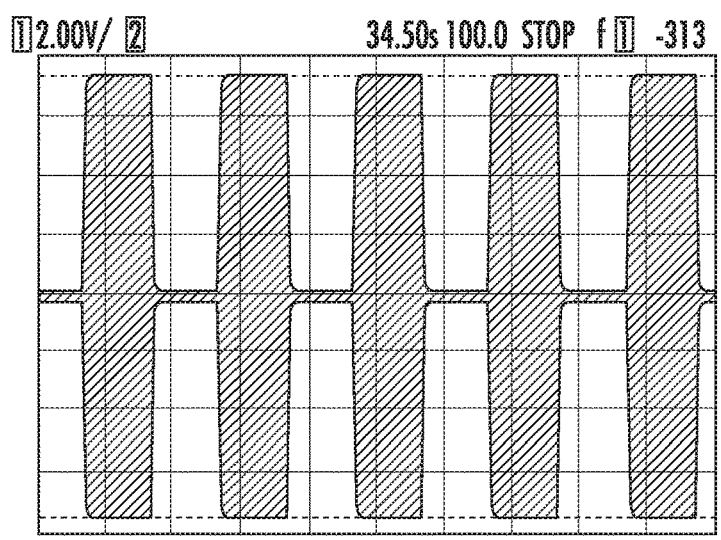

FIGS. 17A-17H illustrate various aspects of an experiment using AM signals with triangular, sinusoidal, and square wave modulating signals. In the first set of experiments, recovery of various low frequency waveforms was studied for AM signals with triangular, sinusoidal or square wave modulating signals, as shown in FIG. 17A-17C. The only difference among AM signals in FIGS. 17A-17C was the shape of the modulating signal and all other parameters including the frequency and amplitude of carrier and modulating signal, were exactly the same The amplitude and frequency of the carrier were 7.5 V and 8 MHz. The amplitude and frequency of the modulating signal were 1V and 5 kHz.

Figure 17E:
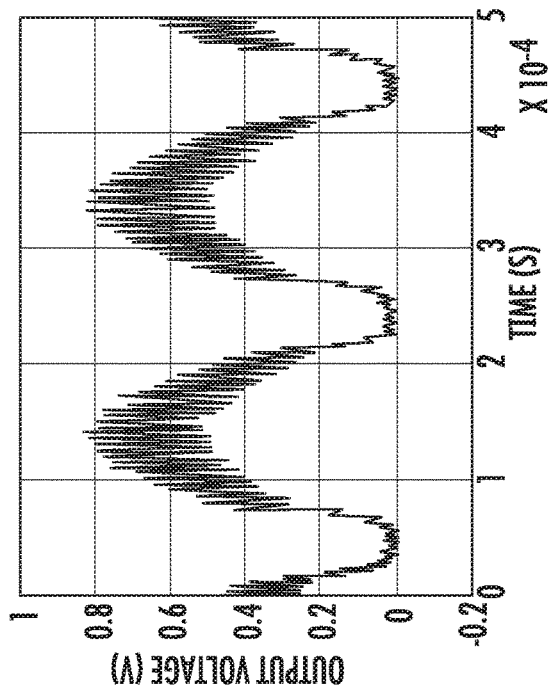
Figure 17F:
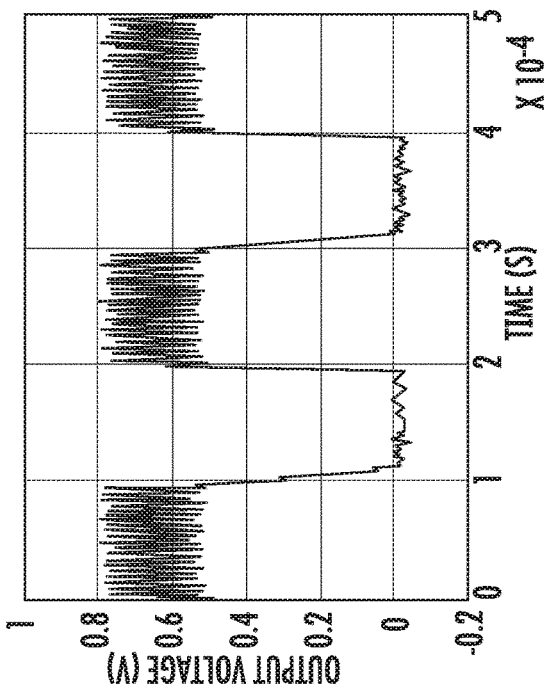
Figure 17D:
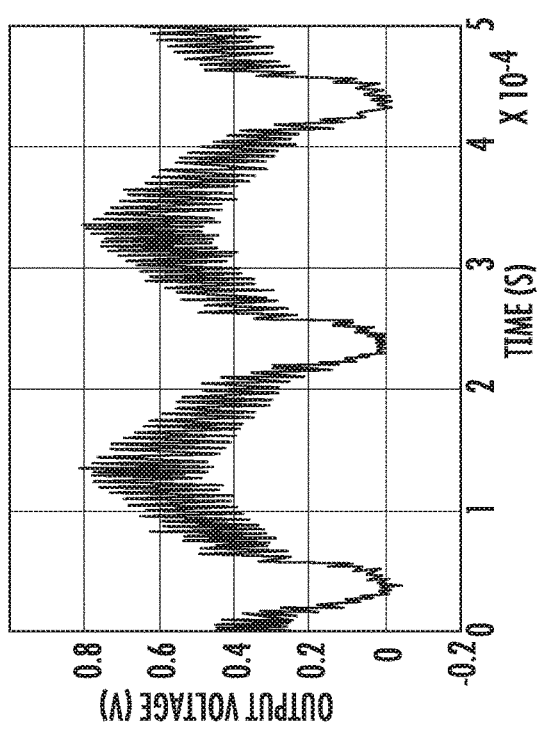

For this study, the frequency of the modulating signal was not the focus and was arbitrarily set at 5 kHz (In the next section we will optimize this frequency). The respective demodulated waveforms over the IDE are shown in FIGS. 17D-17F. As evident from these figures, the system can successfully recover low frequency AC signals with different waveforms from the AM signal. The recovered low frequency waveforms were used to induce ACEO effects on the IDEs, and the ACEO flow velocity were found by PIV of the FluoSpheres™ particles velocity suspended in the solution.

Figure 17G:
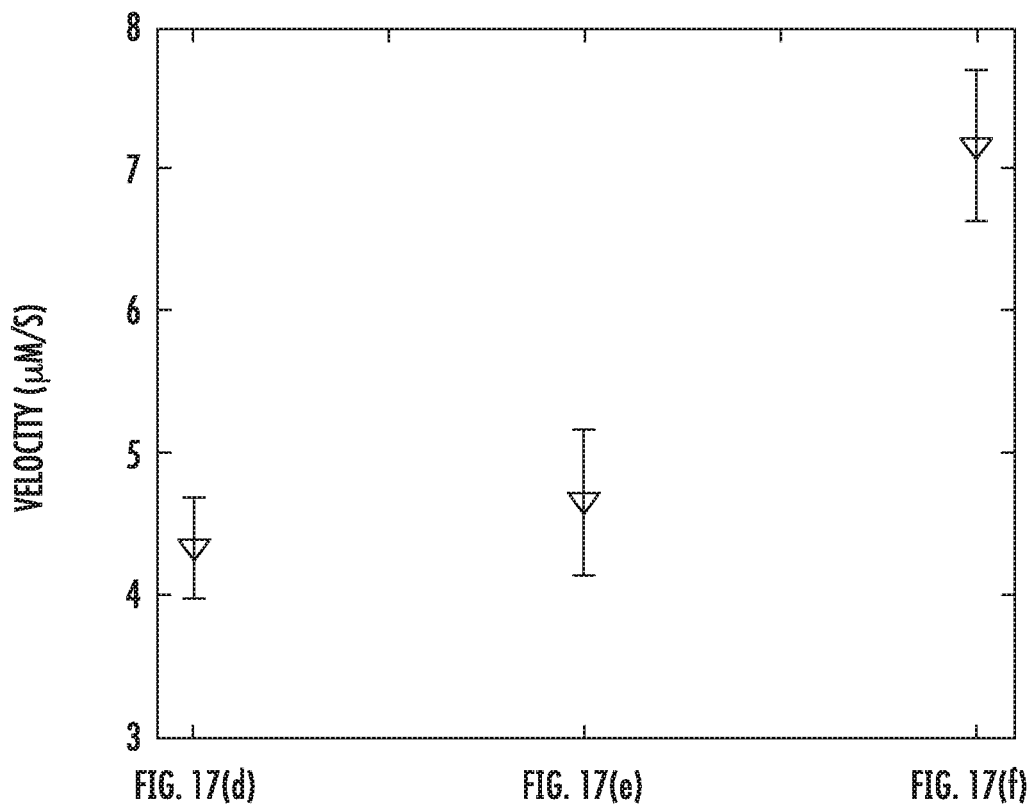
Figure 17H:
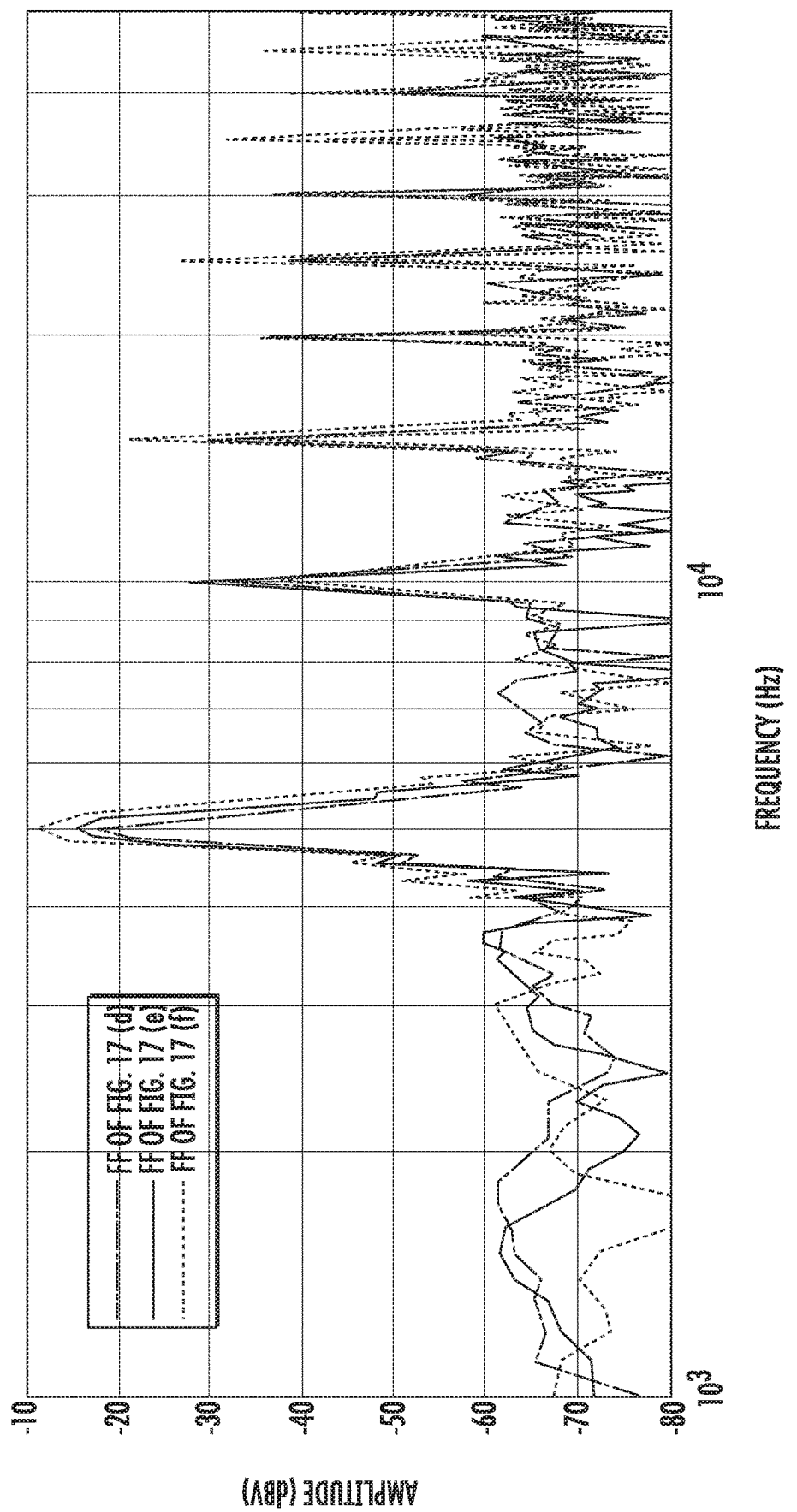

The average of the measured particles' velocity was plotted in FIG. 17G for the three waveforms as shown in FIGS. 17D-17F. It is obvious that the velocity of the particles was higher for the square wave signal shown in FIG. 17F. FIG. 17H shows the measured Fast Fourier Transform (FFT) of three different demodulated waveforms over the IDE. As apparent from the FFT plot, the fundamental harmony of all three signals was located at 5 kHz, and the FFT amplitude for the signal (shown in FIG. 17F) was higher than the other signals. This is the reason why the pulse signal induced ACEO flow velocity is higher than the other signals.

In the next step, recovering a square wave of a different frequency and the effect of signal frequency on excitation of biased-ACEO effect were studied. The circuit performance was studied for 3 different pulse signals with frequencies of 1, 10 and 20 kHz.

Figure 18C:
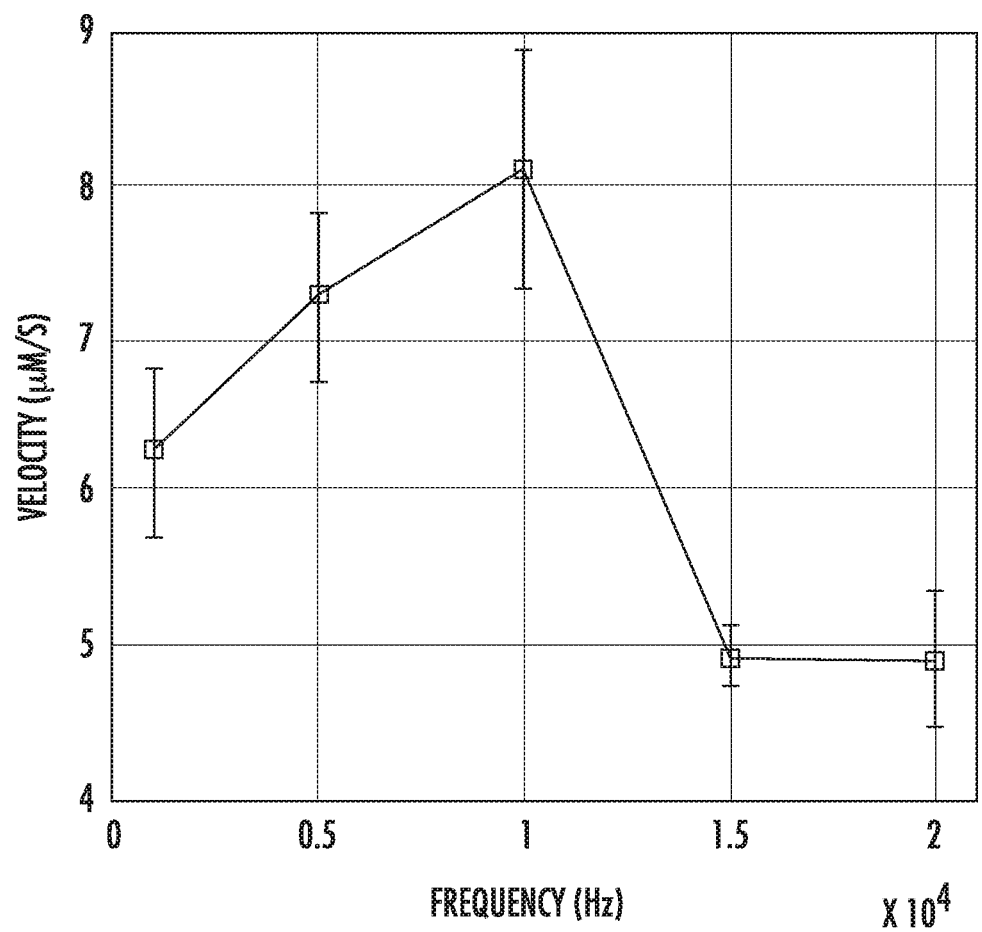

The applied AM signals to the primary coil and their respective demodulated pulse signals over the IDE are shown in FIGS. 18A1-18A3 and FIGS. 18B1-18B3 and FIG. 18C. FIGS. 18A1-A3 show the AM modulated signal over the transmitting coil with a sinusoidal carrier of 7.5 V at 8 MHz. The modulating signals are a pulse signal of 1 V at a frequency of (18A1) 1 kHz, (18A2) 10 kHz and (18A3) 20 kHz, respectively. FIGS. 18B1-18B3 show the recovered low frequency pulse signal over the IDE when the AM signal over the primary coil is as FIG. 18A1, 18A2, or 18A3, respectively. FIG. 18C shows particle velocity in the solution for a pulse signal of different frequencies. Error bar shows standard deviation.

The system could successfully recover low frequency pulse signals with different frequencies from the AM signal. In order to find an optimum frequency for biased-ACEO, particle velocity was studied at different frequencies of the pulse signal. The averages of tracer particle velocity at different frequencies were plotted in FIG. 18C. Based on this figure, particles velocity was maximum around 10 kHz.

According to the study carried out in this section, for excitation of the biased-ACEO effect in the LOF device, it is most efficient to use a pulse signal at 10 kHz as the modulating signal of the AM signal, which was, in turn, adopted for the remainder of the experiments.

FIG. 12 shows the experimental setup for testing the biased-ACEO effect. The separation between the primary and secondary coils is 10 mm. Based on the optimization in previous sections, the modulating signal is a square wave at 10 kHz with an amplitude of 1 V. The frequency of the carrier is set to 8 MHz to take advantage of circuit resonance.

Figure 19:
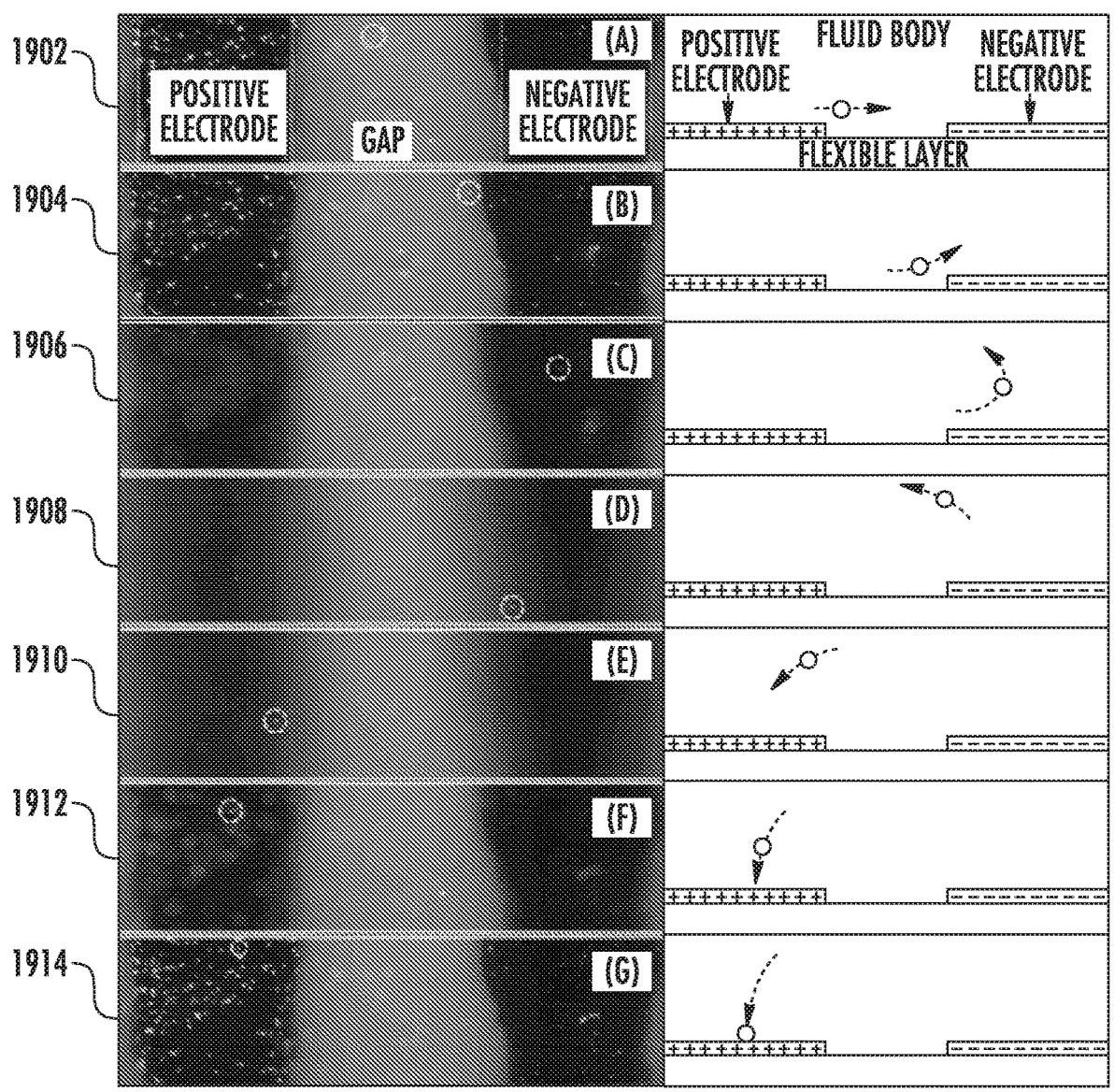
FIG. 19 shows the movement of a particle after applying an AM signal, due to the biased-ACEO effect.

FIG. 19 shows the movement of a particle after applying an AM signal, due to the biased-ACEO effect. In order to better illustrate particle movement, a schematic view of the particle assembly process between two neighboring electrodes is shown in FIG. 19. In this figure, the particle under inspection is located between two electrodes and moves towards the negatively biased electrode (1902 to 1904). When the particle goes over the negative electrode, it is carried upwards by microflows from the electrode surface (1906 to 1908). Then, the particle gradually levitates and moves toward the positive electrode (1910). When it is above the positive electrode, it starts to descend towards the electrode (1912) and finally settles on the positive electrode surface (1914). It can be seen from FIG. 19 that the height of particle changed during its travel, showing a looped path. This is indicative of biased ACEO flow. Electrophoresis or DEP will cause the particle to move straight towards electrodes, which could also be used with this device, either alone or in combination with other induced ACEO effects for a variety of purposes which include salivary diagnostics and drug delivery.

For example, the system can be used as a biosensor, e.g., for rapid, chairside oral fluid diagnostic tests to evaluate oral fluids for disease detection, which, in turn, could facilitate improved access and health care outcomes for patients. In this regard, the system (outside the mouth) is also a tool for rapid, point-of-care tests to provide accurate measurements of clinically validated biomarkers in saliva for screening symptomatic or asymptomatic patients.

The system can be configured for using AC electrokinetic phenomena for sorting and separating out a certain species from a heterogeneous mixture in a colloidal suspension, e.g., by reversing the method used for drug delivery to cause target particles to move away from a source and towards an electrode. In this manner, saliva can be sorted and separated using inductive coupling for salivary diagnostics.

Saliva is regarded as a "mirror of the body" that generally reflects the state of a patient's overall health. A wide range of systemic diseases, such as diabetes and Sjögren's syndrome, have oral manifestations that dentists are ideally situated to monitor and treat. For biosensor applications of the systems and methods described in this specification, oral fluid provides a diagnostic medium for rapid, point-of-care testing by virtue of the response of the biomarker to a non-uniform electrical field at a particular frequency.

Some advantages of using saliva for disease diagnostics includes ease of access, noninvasive sample collection, increased acceptance by patients, and reduced risks of infectious disease transmission. Oral samples are readily accessible as whole saliva or by sampling secretions from specific glands, mucosal transudate, or gingival crevicular fluid. Sampling oral fluids, instead of blood or urine, therefore, provides a medium for detecting a range of candidate biomarkers, such as proteins, electrolytes, hormones, antibodies and DNA/RNA, as well as other substances. Ready access to oral biofluids is helpful for one-time sample collection, and when multiple or serial sampling is required for ongoing, real-time assessment of health and disease status and physiologic markers. Analytes, such as protein and nucleic acid components, which are usually present in lower concentrations in oral fluids than in blood can be monitored with this technology by identifying candidate biomarkers at the molecular level.

Analysing oral fluid using inductive coupling can be useful, for example, in locations where medical equipment may not be available. For instance, consider an army doctor on a battle field performing a rapid diagnostic test. The doctor may not have any electrical power available or electrical function generator equipment. The can use the systems and methods described above to analyse oral fluid using a disposable electrode that does not require electrical wires and connections.

For a biased-ACEO IDE device, its two electrodes have different electrode charging processes, namely capacitive charging for the negatively biased electrode and Faradaic charging for the positively biased electrode. By controlling the voltage level of the demodulated signal over the IDE, vortexes and surface flows with varying strengths can be generated to create different microfluidic phenomena. The wireless biased-ACEO LOF described in this specification is capable of producing various microfluidic phenomena based on the voltage levels at the IDE.

An application of this device is to concentrate particles over designated electrodes. This application becomes very useful for real-time detection of low abundance bioparticles. This application has also proven quite effective in the separation of active drug particles from excepients in various drug formulations used in dentistry, which in combination with other AC electrokinetic effects such as ACEO, has been shown to deliver drug particles to various target sites more effectively than diffusion. When the voltage level over the IDE exceeds the threshold voltage for Faradaic charging, co-ions are generated over the positive electrodes. At lower voltages, Faradaic charging is partially compensated by capacitive charging over the positive electrode.

Consequently, the vortexes within the solution are very weak and the particles slowly move away from the negative electrode onto the positive electrode. A conceptional view of this phenomenon is shown in FIG. 10E and FIG. 19. For a wireless biased-ACEO device, the threshold voltage for the Faradaic reaction was found to be around 0.4 V. Hence, particles assembly occurs when the demodulated voltage level over the IDE is higher than 0.4 V.

Figure 20A:
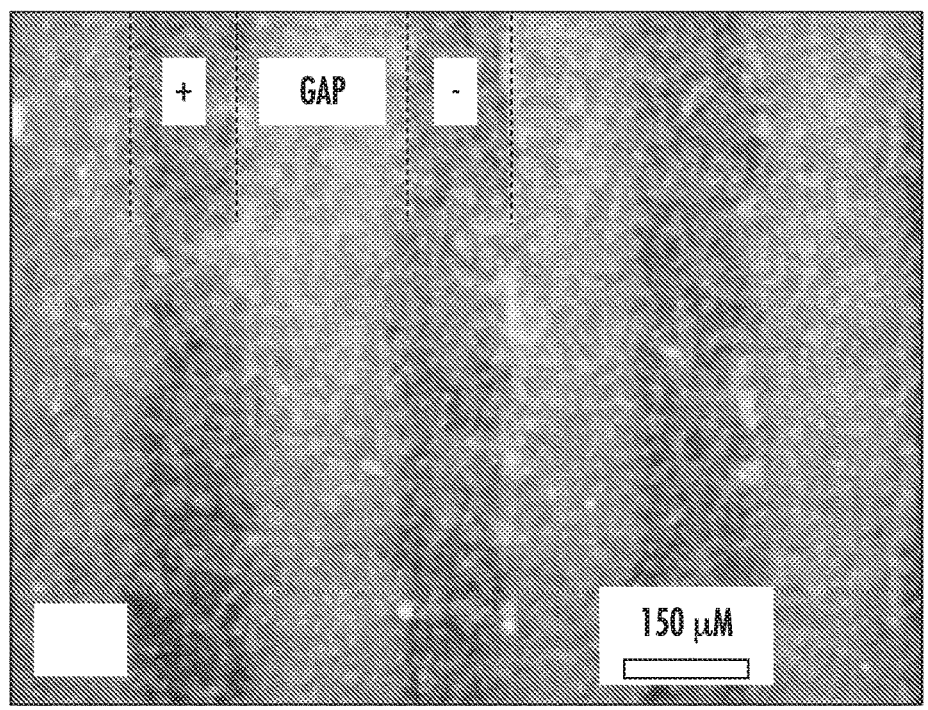
FIGS. 20A-20D illustrate particle and fluid manipulation by wireless biased-ACEO device.
Figure 20B:
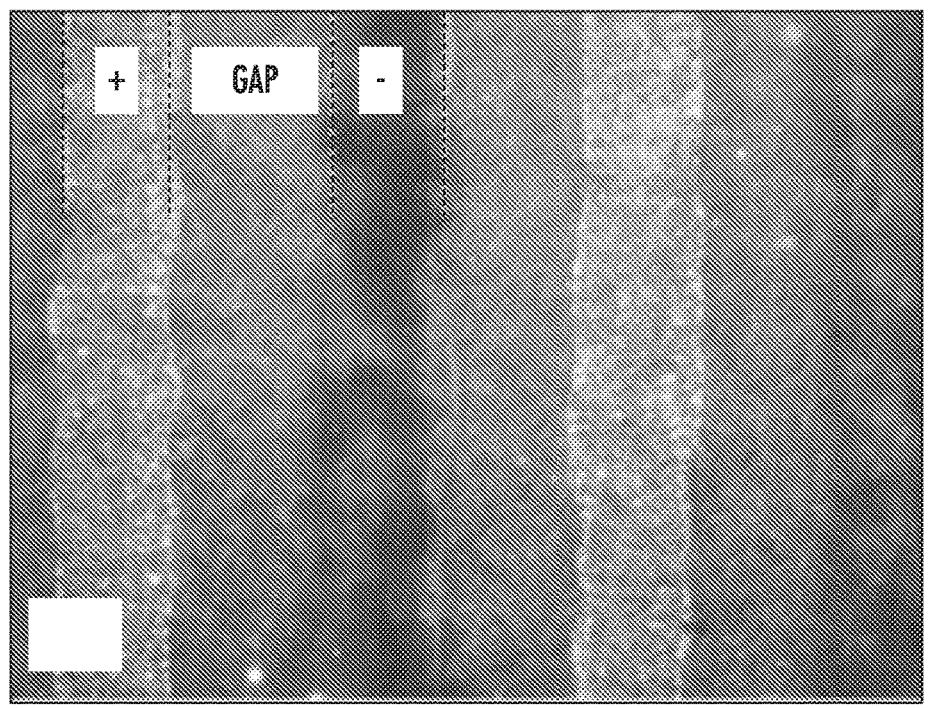
Figure 20C:
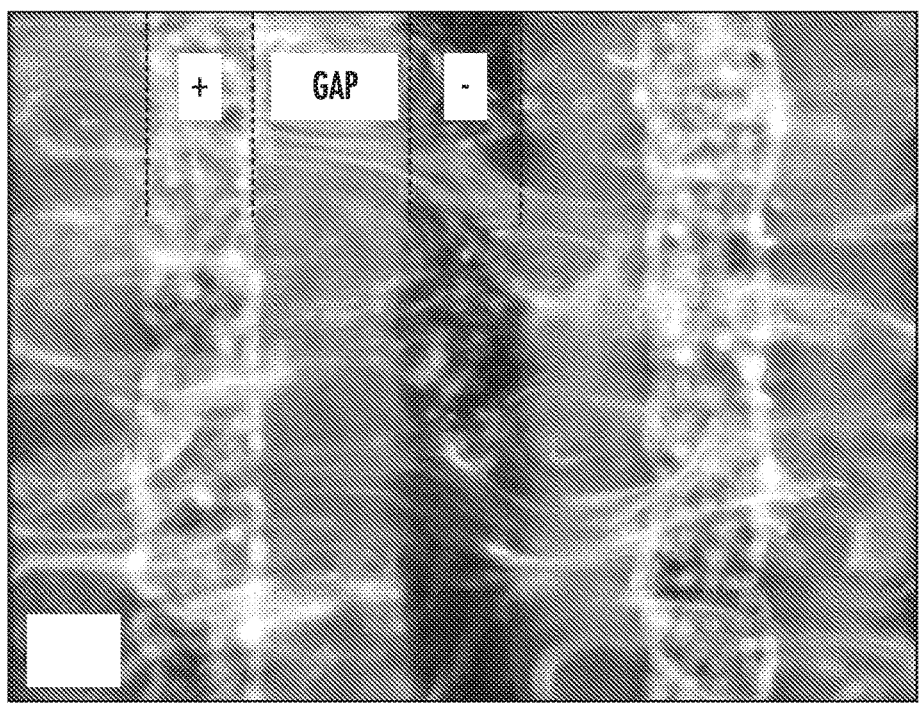
Figure 20D:
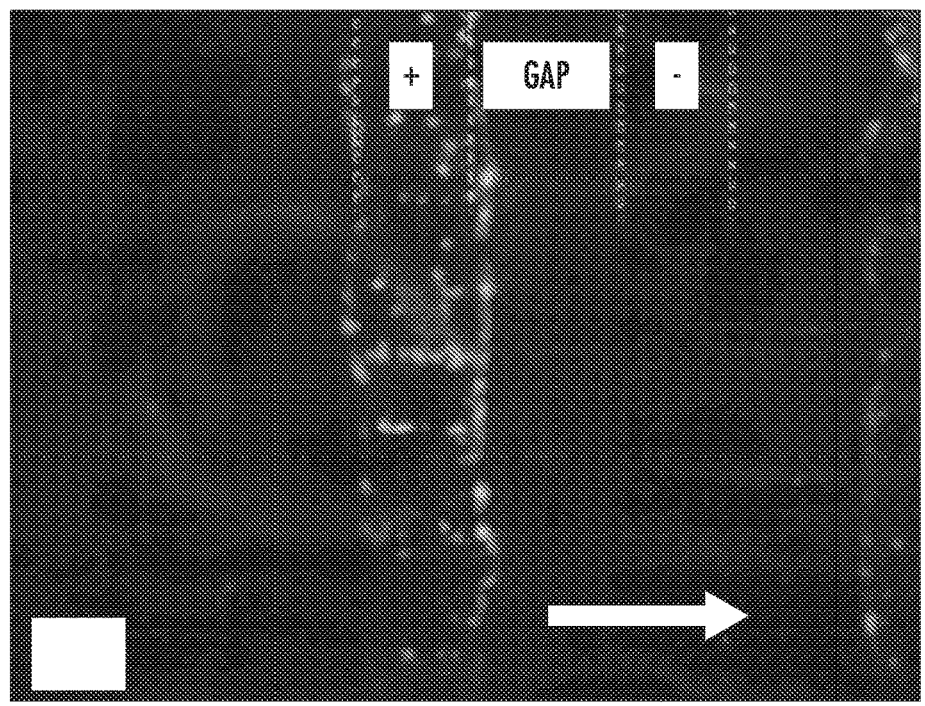

FIGS. 20A-20D illustrate particle and fluid manipulation by wireless biased-ACEO device. FIG. 20A shows a particle distribution inside of the solution loaded over IDE before applying voltage. FIG. 20B shows particle concentration over positively biased electrodes when the demodulated signal's voltage over IDE is around 0.7 V. FIG. 20C shows generation of vortexes and random fluids inside of the solution when demodulated signal's voltage over IDE is around 2 V. FIG. 20D shows fluid flow inside of the solution when demodulated signal's voltage over IDE is around 3 V (the arrow shows fluid flow direction). The positive and negative electrodes are denoted as + and − signs in the figures.

FIG. 20B shows the assembly of particles over the positive electrodes after 20 seconds upon applying the demodulated signal over the IDE. In this figure, the demodulated signal over the IDE was a pulse signal of 0.7 V at 10 kHz. When the demodulated voltage level further increased beyond the threshold voltage, vortices became more pronounced between two neighboring positive and negative electrodes. These vortexes stir the fluid and can be used for mixing of fluids. FIG. 20C shows the stirring fluid flows inside the solution for a 2 V demodulated pulse signal over the IDE. It is apparent that the wireless biased-ACEO device can act as an active mixer.

When the voltage over the IDE goes even higher (higher than 2.5 V), Faradaic charging becomes dominant at the positively biased electrode (FIG. 10G). Due to exponential growth of co-ion concentration with voltage, Faradaic charging can produce co-ions orders of magnitude higher than that produced by capacitive charging. Consequently, ACEO velocity by Faradaic charging is much higher than that by capacitive charging at higher voltages. As a result, at higher voltages, the flow by Faradaic charging dominates and a net flow (as shown in FIG. 10D) is generated toward the negative electrode. For the wireless biased-ACEO LOF, when the voltage exceeds 2.5 V, the vortexes between electrode pairs became connected and a unidirectional fluid flow began to appear. However, there are still some vortexes in the solution due to the jagged electrode edges from PCB fabrication. FIG. 20D shows the fluid flow when a demodulated pulse signal with the frequency of 10 kHz and amplitude of 3 V was applied over the IDE.

Figure 21A:
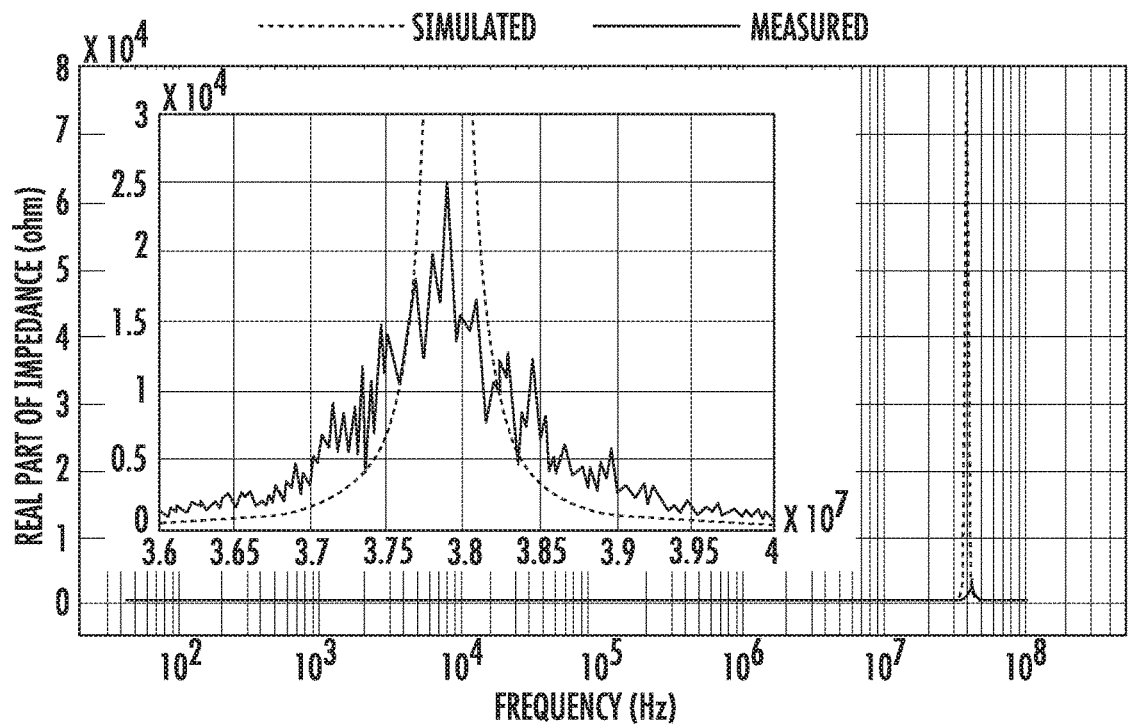
FIGS. 21A-21B, 22, and 23 show the measured impedance characteristics of the two-sided coil and fitted curves.
Figure 21B:
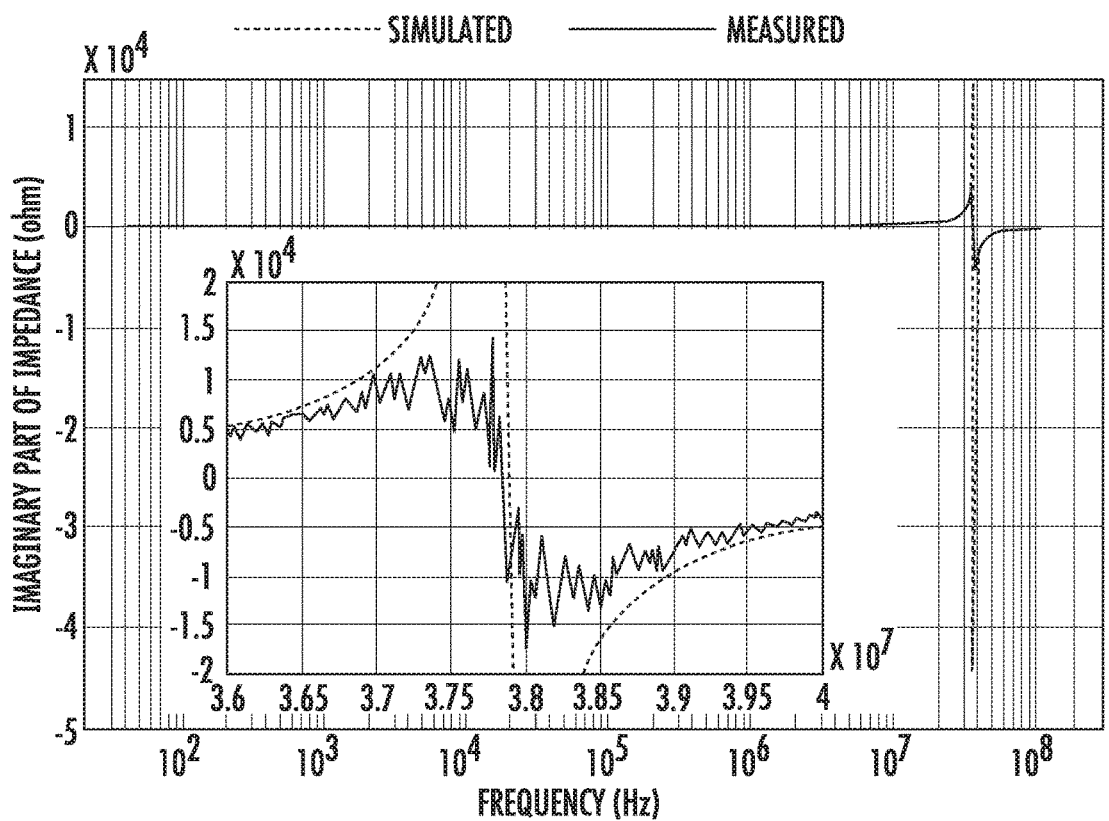
Figure 22:
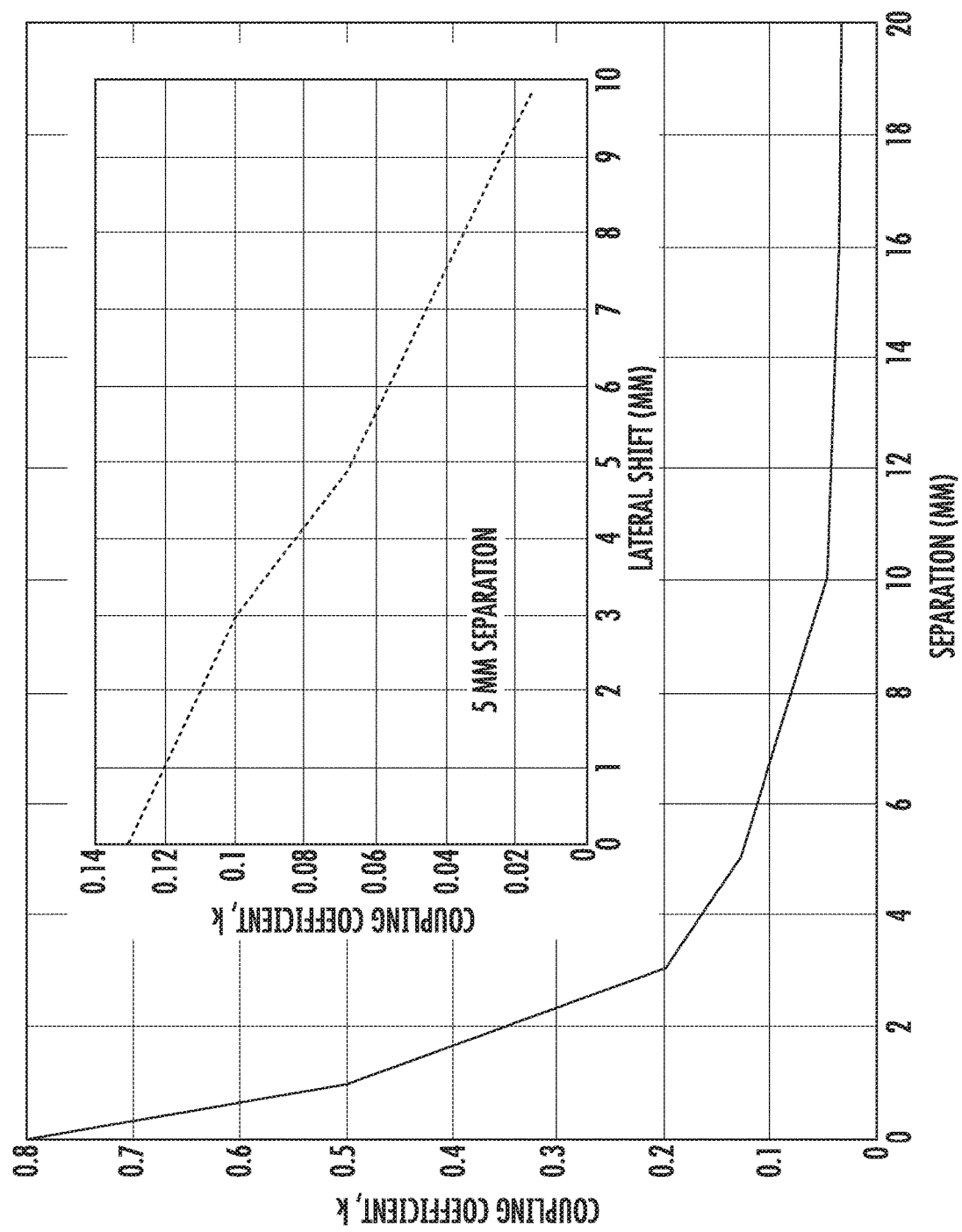

FIGS. 21A-21B, 22, and 23 show the measured impedance characteristics of the two-sided coil and fitted curves. FIG. 21A shows the real part of the impedance. The inset is a zoomed-in region of resonance frequency. FIG. 21B shows the imaginary part of the impedance. The inset is a zoomed-in region of zero-reactance frequency. FIG. 22 shows the coupling coefficient of the coils as a function of separation, and the inset shows the same as a function of lateral shift from alignment.

Figure 23:
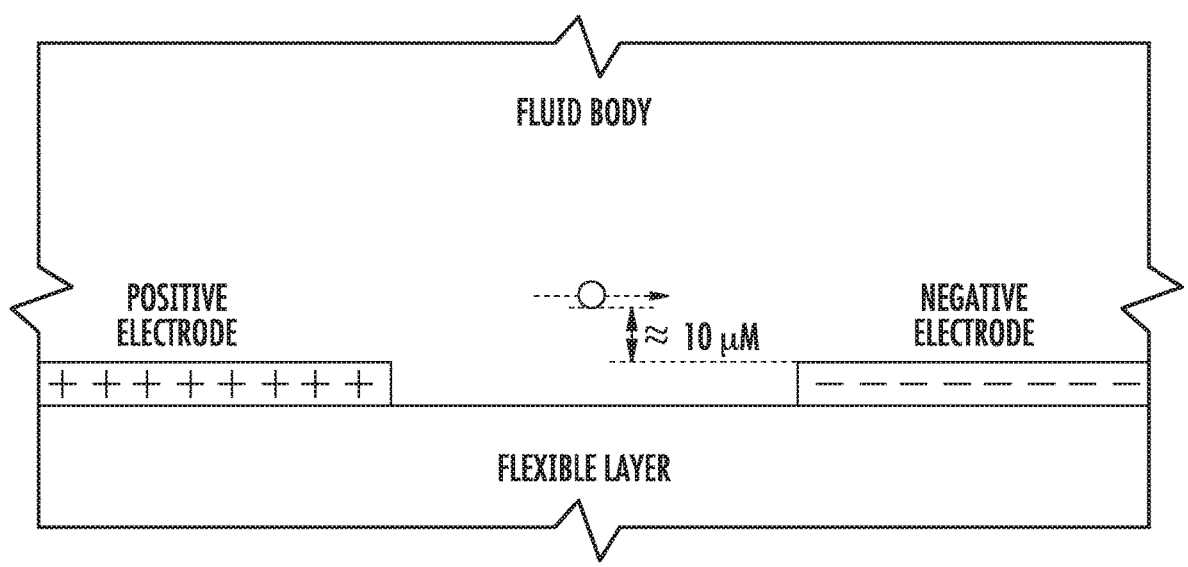

One common practice in measuring k is to measure the inductance of one coil when the other coil is first open-circuited ($L_1$) and then short-circuited ($L_{leak}$). The difference between two measurements is the coil magnetization inductance, which is related to the coupling coefficient as $L_{mag}=k^2 \times L_1$. Hence, coupling coefficient can be calculated by the following, $k\sqrt{L_{mag}/L_1}=\sqrt{(L_1-L_{leak})/L_1}$. The software used for tracking and measuring particles velocity is Image-Pro 3D Suite version 6.0 (MediaCybemetic, Rockville, Md., United States of America), which is a well-known software for microPIV applications. Because ACEK flows have non-uniform streamline, the velocity of a tracer particle is highly dependent on its position relative to the electrodes. Therefore it is desirable to note the location of tracer particles when measuring ACEK flow velocity. FIG. 23 schematically shows the location of the tracked particles.

The space between two electrodes was an optimum location for measuring particle velocity, since the particles had almost constant velocity there. When the particles reached the edge of the electrode their velocity was increasing, which made it very difficult to accurately measure their velocity. Also, when the particles were over electrodes, they had vertical movement. It is difficult to accurately measure their velocity.

The velocity data presented in FIGS. 17 and 18, showing the effect of modulating signal's frequency on biased-ACEO velocity, were measured by the above method. The vertical movement of the particle can be derived by noticing the relative position of the focal plane and the electrodes in FIG. 19. In this study, particle movement was observed by changing the focal point of microscope as the particle moves horizontally and vertically. For example, in FIGS. 19A-19B, the vertical distance of the particle and electrode is very close because the focal point of microscope is set on the particle, however the particles on the surface of the positive and negative electrodes can be obviously seen. When the particle moves vertically in FIGS. 19D-19F the focal point is again set on the particle but because the particle is going away from the electrode surface, the resolution of the electrode surface is very low and the electrode surface and particles over them cannot be seen. However, in FIG. 19F, when the particle moves toward positive electrode, the resolution of electrode surface increases. Finally, in FIG. 19G, when the particle reaches the positive electrode surface, the electrode and all particles over it are obviously seen.

CONCLUSION—LOF DEVICE

The presently disclosed subject matter provides a wireless biased-ACEO lab-on-a-film device that has been designed and characterized for different microfluidic applications. The required low frequency AC signal for generation of biased-ACEO effect was wirelessly transmitted through an AM technique. Unlike many wireless microfluidic systems, this system works with low voltage to generate microfluidic functions, despite the inductive link being very leaky (less than 60 V). Low voltage operation is attributed to two design considerations. One is that the circuit design on the LOF produces a resonance at the output of the receiving coil for usable voltage to be extracted, and the other is the use of the ACEO effect, which typically produces strong microfluidic movement at low voltage.

It will be understood that various details of the subject matter described herein may be changed without departing from the scope of the subject matter described herein. Furthermore, the foregoing description is for the purpose of illustration only, and not for the purpose of limitation, as the subject matter described herein is defined by the claims as set forth hereinafter.

What is claimed is:

1. A system comprising:
    a drug delivery patch comprising:
       a substrate;
       an electrode integrated with the substrate, wherein the electrode comprises an interdigitated array electrode (IDE) or a portion of an IDE;
       a plurality of receiving coils;
       a plurality of envelope detectors coupled to the receiving coils and configured to demodulate an output from the receiving coils to supply a plurality of waveforms to the electrode; and
       a fluid in the substrate having drug particles suspended in the fluid; and
    a remote power unit for the drug delivery patch, the remote power unit comprising:
       an antenna; and
       a circuit configured to drive the antenna to emit a wireless signal comprising a plurality of amplitude modulated carrier signals to the drug delivery patch to power the drug delivery patch by inductive coupling, thereby causing the receiving coils and the envelope detectors to supply a demodulated signal to the electrode in the drug delivery patch to motivate the drug particles towards a target site of the drug delivery patch;
    wherein the drug delivery patch is a passive electrical device powered by the remote power unit and the electrode of the drug delivery patch is configured to passively generate, from the wireless signal, an electrical field that motivates the drug particles towards the target via alternating current electroosmosis (ACEO) induced by biased alternating current electrokinetics (ACEK) signals recovered from the wireless signal, and wherein the ACEO induced by the biased ACEK signals causes two counter-rotating vortices above the electrode to motivate the drug particles.

2. The system of claim 1, wherein the antenna of the remote power unit comprises a transmitting coil.

3. The system of claim 1, wherein the envelope detectors comprise resistor-capacitor (RC) envelope detectors.

4. The system of claim 3, wherein the waveforms are biphasic waveforms for charge balance.

5. The system of claim 3, wherein the receiving coils and the RC envelope detectors are monolithically integrated.

6. The system of claim 1, wherein the circuit comprises a pair of modulated voltage sources to generate the amplitude modulated carrier signals.

7. The system of claim 1, wherein the circuit and the receiving coils are configured so that the carrier signals undergo resonance at the receiving coils.

8. The system of claim 1, wherein the drug particles comprise antibiotics, anesthetics, analgesics and/or anti-inflammatory drug particles.

* * * * *